(12) United States Patent
Cui et al.

(10) Patent No.: US 9,540,656 B2
(45) Date of Patent: Jan. 10, 2017

(54) STACKED HERBICIDE TOLERANCE EVENT 8291.45.36.2, RELATED TRANSGENIC SOYBEAN LINES, AND DETECTION THEREOF

(75) Inventors: Yunxing Cory Cui, Carmel, IN (US); Thomas Hoffman, Zionsville, IN (US); Ning Zhou, Zionsville, IN (US); Stephen Novak, Westfield, IN (US); Julissa Colon, West Lafayette, IN (US); Dawn M. Parkhurst, Avon, IN (US); Sandra Grace Toledo, West Lafayette, IN (US); Terry R. Wright, Carmel, IN (US); Sean Michael Russell, Carmel, IN (US); Bruce Held, Ames, IA (US); Vaithilingam Sekar, Ames, IA (US)

(73) Assignee: Dow AgroSciences LLC, Indianapolis, IN (US)

( * ) Notice: Subject to any disclaimer, the term of this patent is extended or adjusted under 35 U.S.C. 154(b) by 179 days.

(21) Appl. No.: 13/991,309

(22) PCT Filed: Dec. 2, 2011

(86) PCT No.: PCT/US2011/063133
§ 371 (c)(1),
(2), (4) Date: Sep. 3, 2013

(87) PCT Pub. No.: WO2012/075429
PCT Pub. Date: Jun. 7, 2012

(65) Prior Publication Data
US 2013/0338006 A1    Dec. 19, 2013

Related U.S. Application Data

(60) Provisional application No. 61/419,709, filed on Dec. 3, 2010, provisional application No. 61/471,845, filed on Apr. 5, 2011, provisional application No. 61/511,664, filed on Jul. 26, 2011, provisional application No. 61/521,798, filed on Aug. 10, 2011.

(51) Int. Cl.

| | |
|---|---|
| *C12N 15/82* | (2006.01) |
| *A01H 5/10* | (2006.01) |
| *A01H 5/00* | (2006.01) |
| *C12N 9/02* | (2006.01) |
| *C12N 9/10* | (2006.01) |

(52) U.S. Cl.
CPC ............ *C12N 15/8275* (2013.01); *A01H 5/10* (2013.01); *C12N 9/0069* (2013.01); *C12N 9/0071* (2013.01); *C12N 9/1029* (2013.01); *C12N 9/1092* (2013.01); *C12N 15/82* (2013.01); *C12N 15/8274* (2013.01); *C12Y 114/11017* (2013.01); *C12Y 203/01183* (2013.01); *C12Y 205/01019* (2013.01)

(58) Field of Classification Search
CPC .................................. A01H 5/00; C12N 15/82
See application file for complete search history.

(56) References Cited

U.S. PATENT DOCUMENTS

| 7,626,077 B2 | 12/2009 | Held et al. |
|---|---|---|
| 7,695,914 B2 | 4/2010 | Bing et al. |
| 7,696,341 B2 | 4/2010 | Bing et al. |
| 7,723,575 B2 | 5/2010 | Alibhai et al. |
| 7,750,207 B2 | 7/2010 | Wu et al. |
| 7,786,353 B2 | 8/2010 | Fernandes |
| 7,807,791 B2 | 10/2010 | Sekar et al. |
| 7,834,146 B2 | 11/2010 | Kovalic et al. |
| 7,883,850 B2 | 2/2011 | Song et al. |
| 8,916,752 B2 | 12/2014 | Wright et al. |
| 2002/0013958 A1 | 1/2002 | Lalgudi et al. |
| 2004/0031072 A1 | 2/2004 | La Rosa et al. |
| 2005/0216969 A1 | 9/2005 | Song |

(Continued)

FOREIGN PATENT DOCUMENTS

| CN | 1561168 | 1/2005 |
|---|---|---|
| CN | 101020905 | 8/2007 |

(Continued)

OTHER PUBLICATIONS

Shaner, D. L. "Role of translocation as a mechanism of resistance to glyphosate." Weed Science 57.1 (2009): 118-123.*
Schmutz, J., et al. "Genome sequence of the palaeopolyploid soybean." nature 463(7278): 178-183, Jan. 14, 2010.*
Ron Brunoehler, Going public cuts soybean seed costs, corn and soybean digest, Feb. 2000.*
EMBL Accession No. HN002532, GSS_Ba205J12.R GSS_Ba Glycine soja genomic 3', genomic survey sequence, May 9, 2010.
XP-002732015, AAD-12, 2mepsps, pat. Glycine max (L.) Merr. (DAS44406 OECD UI DAS-44406-6 AFFRC Feb. 7, 2011.

(Continued)

*Primary Examiner* — Lee A Visone
*Assistant Examiner* — Fan Weihua
(74) *Attorney, Agent, or Firm* — James Daly, IV; Barnes & Thornburg LLP

(57) ABSTRACT

This invention relates to soybean event pDAB8291.45.36.2, which includes a novel expression cassette comprising multiple traits conferring resistance to glyphosate, aryloxyalkanoate, and glufosinate herbicides. This invention also relates in part to methods of controlling resistant weeds, plant breeding, and herbicide tolerant plants. In some embodiments, the event sequence can be "stacked" with other traits, including, for example, other herbicide tolerance gene(s) and/or insect-inhibitory proteins. This invention further relates in part to detection methods, including endpoint TaqMan PCR assays, for the detection of Event pDAB8291.45.36.2 in soybeans and related plant material. Some embodiments can perform high throughput zygosity analysis of plant material and other embodiments can be used to uniquely identify the zygosity of and breed soybean lines comprising the event of the subject invention. Kits and conditions useful in conducting these assays are also provided.

14 Claims, 4 Drawing Sheets

(56) References Cited

U.S. PATENT DOCUMENTS

| | | |
|---|---|---|
| 2006/0282915 A1 | 12/2006 | Malven |
| 2007/0083945 A1 | 4/2007 | Byrum |
| 2007/0143873 A1 | 6/2007 | Pratelli et al. |
| 2007/0143876 A1 | 6/2007 | Song et al. |
| 2008/0051288 A1 | 2/2008 | Cressman et al. |
| 2009/0093366 A1* | 4/2009 | Wright et al. ............... 504/142 |
| 2009/0104700 A1 | 4/2009 | Samuel et al. |
| 2010/0197503 A1 | 8/2010 | Hawkes et al. |
| 2010/0251432 A1 | 9/2010 | Lira et al. |
| 2013/0055453 A1 | 2/2013 | Hoffman et al. |
| 2015/0080218 A1 | 3/2015 | Wright et al. |

FOREIGN PATENT DOCUMENTS

| | | | |
|---|---|---|---|
| EP | 2309843 | 4/2011 | |
| JP | A-2004-27091 | 1/2004 | |
| UA | A200714839 | 4/2008 | |
| WO | WO 2004/011601 | 2/2004 | |
| WO | WO 2004/074443 | 9/2004 | |
| WO | WO 2006/045633 | 5/2006 | |
| WO | WO2006130436 | 12/2006 | |
| WO | WO 2007/053482 | 5/2007 | |
| WO | WO2007053482 | * 5/2007 | ............... A01H 5/00 |
| WO | WO 2009/037329 | 3/2009 | |
| WO | WO 2009/152359 | 12/2009 | |
| WO | WO 2010/002984 | 1/2010 | |
| WO | WO 2010/008760 | 1/2010 | |
| WO | WO 2010/015627 | 2/2010 | |
| WO | WO 2010/079032 | 7/2010 | |
| WO | WO2011063413 | * 5/2011 | ............... A01H 5/00 |
| WO | WO 2011/066360 | 6/2011 | |
| WO | WO 2011/066382 | 6/2011 | |
| WO | WO 2011/066384 | 6/2011 | |
| WO | WO 2012/075426 | 6/2012 | |

OTHER PUBLICATIONS

Lam, Hon-Ming, et al. "Resequencing of 31 wild and cultivated soybean genomes identifies patterns of genetic diversity and selection," 2010, Nature genetics 42, 1053-1059.

Schmutz, J., et al. "Genome sequence of the palaeopolyploid soybean," 2010, Nature, 463, 178-183.

Zhong, Gan-Yuan, "Genetic issues and pitfalls in transgenic plant breeding," 2001, Euphytica 118, 137-144.

Database Geneseq [Online] Jul. 24, 2008 (Jul. 24, 2008), "B. napas PCR primer RflRV."

GenBank accession: HQ403648—Eleusine indica 5-enolpyruvylshikimate-3-phosphate synthase (epsps-R) mRNA, complete cds; plastid—May 27, 2011.

GenBank accession: HQ403647—Eleusine indica 5-enolpyruvylshikimate-3-phosphate synthase (EPSPS-S) mRNA, complete cds; plasmid—May 27, 2011.

GenBank accession: GU256772—Mutant Zoysia japonica 5-enolpyruvyl shikimate 3-phosphate synthase (EPSPS) mRNA, complete cds—Jan. 27, 2010.

GenBank accession: GU256771—Zoysia japonica 5-enolpyruvyl shikimate 3-phosphate synthase (EPSPS) mRNA, complete cds.—Jan. 27, 2010.

http://www.bch.biodic.go.jp/download/en_lmo/H23_9_6_DAS44406.pdf—aad-12, 2mepsps, pat, Glycine max (L.) Merr. (OAS44406, OECO UI: OAS-44406-6)—Feb. 7, 2011.

GenBank accession: XM_002436379—Sorghum bicolor hypothetical protein, mRNA—Jul. 13, 2009.

GenBank accession: GX744067—Sequence 12246 from U.S. Pat. No. 7,834,146—Dec. 13, 2010.

GenBank accession: GX619320—Sequence 5 from U.S. Pat. No. 7,807,791—Dec. 13, 2010.

GenBank accession: GX315220—Sequence 9295 from U.S. Pat. No. 7,750,207—Dec. 12, 2010.

GenBank accession: GX270866—Sequence 47 from U.S. Pat. No. 7,723,575—Aug. 13, 2010.

GenBank accession: GY007493—Sequence 3 from U.S. Pat. No. 7,883,850—Apr. 30, 2011.

GenBank accession: JA216562—Sequence 39 from patent EP2309843—Apr. 26, 2011.

GenBank accession: FW377938—Transgenic plant event detection—Sep. 30, 2010.

GenBank accession: GX006377—Sequence 27 from U.S. Pat. No. 7,696,341—Aug. 13, 2010.

GenBank accession: GX006374—Sequence 24 from U.S. Pat. No. 7,696,341—Aug. 13, 2010.

GenBank accession: GX003492—Sequence 27 from U.S. Pat. No. 7,695,914—Aug. 13, 2010.

GenBank accession: GX003489—Sequence 24 from U.S. Pat. No. 7,695,914—Aug. 13, 2010.

GenBank accession: HD115809—Sequence 29 from Patent WO2010079032—Aug. 11, 2010.

GenBank accession: GQ497217—Glycine max transgenic GMO cassette genomic sequence—Sep. 28, 2009.

GenBank accession: FJ410919—Binary vector pWY109, complete sequence—Jan. 12, 2009.

GenBank accession: EU554319—Yeast selection vector pIS421, complete sequence—Sep. 23, 2008.

GenBank accession: DQ15655—Zea mays transgenic phosphinothricin acetyltransferase gene, partial cds; and beta lactamase and phosphinothricin acetyltransferase genes, complete cds—Mar. 1, 2006.

GenBank accession: AC217803—Canis familiaris chromosome 21, clone WORK_REGION, complete sequence—Feb. 28, 2008.

GenBank accession: AC187003—Canis Familiaris chromosome 21, clone XX-427H12, complete sequence—Jul. 29, 2006.

GenBank accession: AK157167—Mus musculus activated spleen cDNA, RIKEN full-length enriched library, clone: F830205P13 product: unclassifiable, full insert sequence—Oct. 16, 2010.

GenBank accession: AK081799—Mus musculus 16 days embryo head cDNA, RIKEN full-length enriched library, clone: C130078E19 product: unclassifiable, full insert sequence—Oct. 6, 2010.

GenBank accession: AB073156—Arabidopsis thaliana DNA, chromosome 4 centromere region, BAC clone: F13F19—Feb. 14, 2004.

GenBank accession: BT090294—Soybean clone JCVI-FLGm-4121 unknown mRNA—Aug. 6, 2009.

GenBank. Accesion AY395700—Eleusine indica 5-enolpyruvylshikimate-3-phosphate synthase (EPSPS-S) mRNA, partial cds—Oct. 29, 2006.

GenBank. Accesion AJ417034—Eleusine indica platid partial mRNA for 5-enolpyruvylshikimate-3-phosphate synthase (EPSPS-S gene)—Apr. 15, 2005.

GenBank. Accesion X63374—Z. mays mRNA for EPSP-synthase—May 18, 2005.

GenBank. Accesion AY106729—Zea mays PCO094563 mRNA sequence—Jun. 2, 2008.

GenBank. Accesion CQ868456—Sequence 3 from Patent WO2004074443—Sep. 13, 2004.

GenBank. Accession GP765237—Sequence 5 from U.S. Pat. No. 7,626,077—Dec. 14, 2009.

GenBank. Accession D1012786—Chimera gene with several herbicide resistant genes, plant cell and plant resistant to several herbicides—Feb. 21, 2008.

GenBank. Accession CS434496—Sequence 14 from Patent WO2006045633—Oct. 24, 2006.

GenBank. Accession EU090199—Brassica napus transgenic line Rf1 right border junction sequence of transgenic event genomic sequence—Nov. 7, 2007.

GenBank. Accession GU574780—MISSA recipient vector BIBAC-LTR, complete sequence—May 6, 2010.

GenBank. Accession GN123171—Sequence 6067 from Patent WO2009037329—Apr. 24, 2009.

GenBank. Accession GN123168—Sequence 6064 from Patent WO2009037329—Apr. 24, 2009.

GenBank. Accession GN123173—Sequence 6069 from Patent WO2009037329—Apr. 24, 2009.

GenBank. Accession XM_002980455—Selaginella moellendorffii hypothetical protein, mRNA—Aug. 13, 2010.

(56) References Cited

OTHER PUBLICATIONS

Database Geneseq [Online] Jul. 9, 2009 (Jul. 9, 2009), Soybean nucleic acid SEQ ID No. 133298>>, retrieved from EBI accession No. GSN:ARD51602 Database accession No. ARD51602.
ARD51602, Database GeneSeq[online], Apr. 12, 2007/.
A59344, Database DDBJ[online], Mar. 6, 1998, A59344.1, http://getentry.ddbi.nig.ac.ip/getentry/na/A59344/?filetype=html.
A02774, Database DDBJ[online], Mar. 25, 1993, A02774.1, http://getentrv.ddbi.nig.ac.ip/getentrv/na/A02774/?filetype=html.
AAN50226, Database GeneSeq[online], Oct. 24, 2003.
AB027254, Database DDBJfonline], Jan. 24, 2004.
BC100043, Database DDBJ[online], Aug. 15, 2005.
ARU42167, Database GeneSeqlonline], Aug. 21, 2008.
AQY41271, Database GeneSeq[online], Jul. 10, 2008.
Pakula, AA et al., "Genetic analysis of protein stability and function," 1989, Anna. Rev. Genet, 23, pp. 289-310. (abstract only).
Fraenkel, AE. et al., "Characterization of diphtheria fusion proteins targeted to the human interleukin-3 receptor," 2000, Protein Eng., vol. 13, No. 8, 575-581.
Database NCBI Reference Sequence: XM_002582376.1 from Sep. 16, 2009.
Database NCBI Reference Sequence: XM_002980455.1 from Aug. 13, 2010 (see sequence).
https://www.jpo.go.jp/shiryou/s_sonata/hyoujun_gijutsu/kakusan/001.html.
GenBank; AK286292.1. Glycine max cDNA, clone: GMFL01-25-J19 [online] Nov. 19, 2008 [retrieved on Mar. 14, 2012]. Available on the internet: <URL:http:www.ncbi.nlm.nih.gov/nuccore/AK286292.1>.
GenBank EU721743.1. Glycine max clone BAC 71B1. [online] Dec. 5, 2008 [retrieved Mar. 14, 2012]. Available on the internet: <URL:http://www.ncbi.nlm.nih.gov/nuccore/EU721743>.
Database Geneseq [Online] Jul. 9, 2009 (Jul. 9, 2009), "Soybean nucleic acid SEQ ID No. 133298.", XP002721468, retrieved from EBI accession No. GSN:ARD51602.
Database Geneseq [Online] Jul. 9, 2009 (Jul. 9, 2009), "Soybean nucleic acid SEQ ID No. 33302.", XP002721469, retrieved from EBI accession No. GSN:ARC51605.
Database EMBL [Online] Oct. 28, 2006 (Oct. 28, 2006), "GM_WBa0024I05.r GM_WBa Glycine max genomic clone GM_WBa0024I05 3', genomic survey sequence.", XP002721470, retrieved from EBI accession No. EM_GSS:ED626487.
Database EMBL [Online] May 9, 2010 (May 9, 2010), "GSS_Ba098E14. R GSS_Ba Glycine soja genomic 3 ', genomic survey sequence.", XP002721471, retrieved from EBI accession No. EM_GSS:HN019107.
Database EMBL [Online] Nov. 1, 2008 (Nov. 1, 2008), "Glycine max clone BAC 71B1, * Sequencing in Progress*, 3 unordered pieces.", XP002721472, retrieved from EBI accession No. EM HTG:EU721743.
Database EMBL [Online] Nov. 18, 2004 (Nov. 18, 2004), "Com seedling-derived polynucleotide (cpds), SEQ ID 5567.", XP002721473, retrieved from EBI accession No. GSN:ADS70551.
Database Geneseq [Online] Aug. 23, 2007 (Aug. 23, 2007), "Cry1F event 281-24-236 transgene, SEQ ID 1.", XP002721474, retrieved from EBI accession No. GSN:AGD74685.
Database Geneseq [Online] Jul. 24, 2008 (Jul. 24, 2008), "B. napas PCR primer Rf1RV.", XP002721475, retrieved from EBI accession No. GSN:ARW87360.
Database Geneseq [Online] Apr. 1, 2010 (Apr. 1, 2010), "miRNA targeted gene sequence SEQ ID N0:237.", XP002721475, retrieved from EBI accession No. GSN:AXU86864.
"Glycine max chromosome 15, whole genome shotgun sequence" [Jan. 11, 2010, online] retrieved from GenBank [retrieved on Jun. 23, 2016], accession No. CM000848 in http://www.ncbi.nlm.nih.gov/nuccore/283570559?sat=16&satkey=5691280.
GenBank: AK286292.1 Glycine max cDNA, clone: GMFLO1-25-J19 [online] p. 1.

* cited by examiner

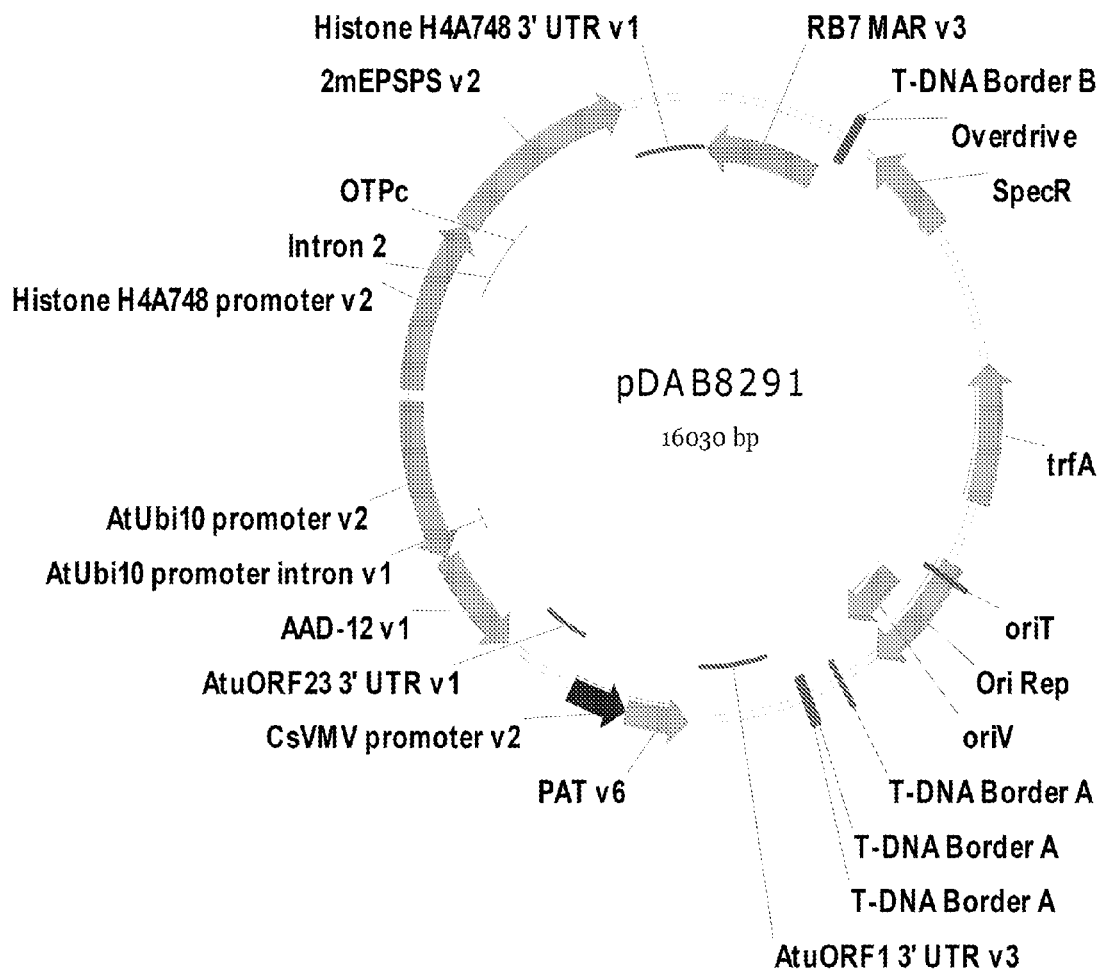
Figure 1. Plasmid Map of pDAB8291 containing the *2mepsps v2*, *aad*-12 and *pat* Expression Cassettes.

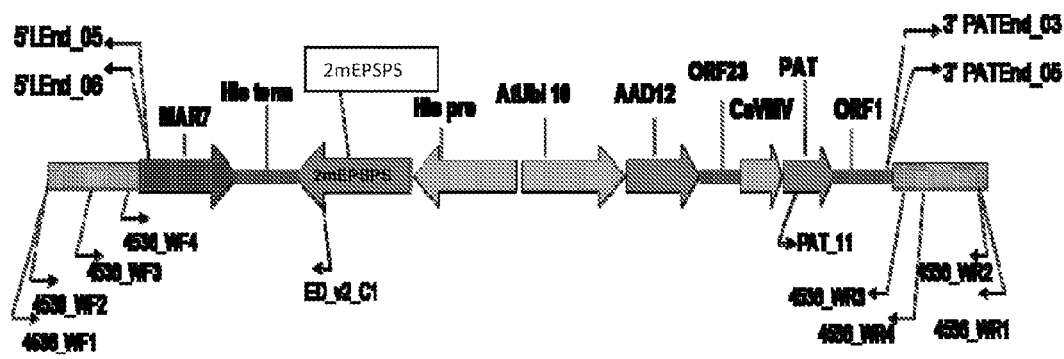
Figure 2. Schematic diagram of primer locations for soybean Event pDAB8291.45.36.2 from 5' to 3' borders.

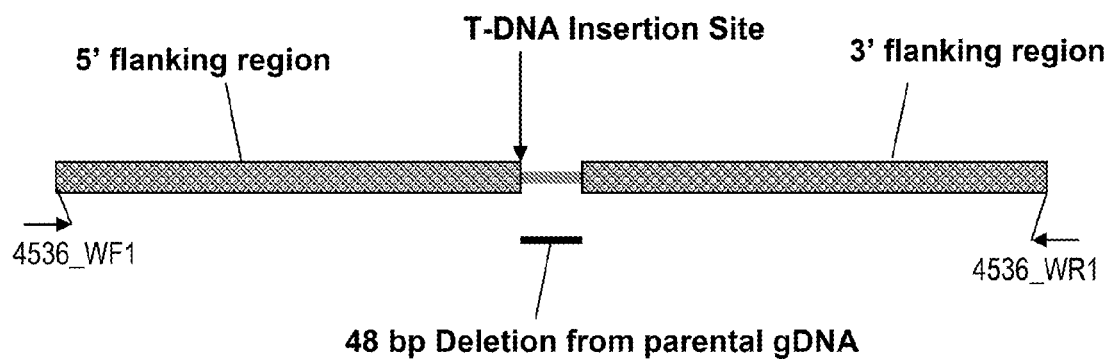
Figure 3. Schematic diagram depicting primer locations and genomic deletion in soybean Event pDAB8291.45.36.2.

Figure 4. The schematic diagram depicts the primer locations for the Taqman assay of the soybean event pDAB8291.45.36.2.
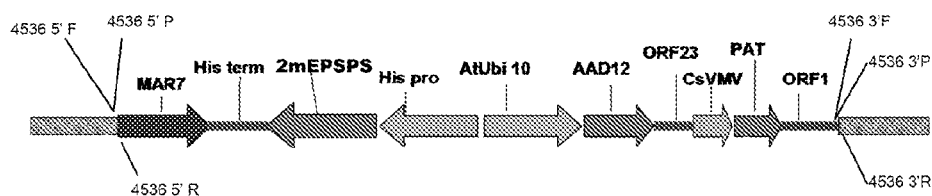

SEQUENCE LISTING

```
<160> NUMBER OF SEQ ID NOS: 29

<210> SEQ ID NO 1
<211> LENGTH: 3088
<212> TYPE: DNA
<213> ORGANISM: Artificial Sequence
<220> FEATURE:
<223> OTHER INFORMATION: The 5' flanking border sequence for the subject
      soybean Event pDAB8291.45.36.2

<400> SEQUENCE: 1
agctttgact ggaaaaacat gagcctacat attttttata ttttgcagat tgatggaagt      60
tacctgttca acttagaagg tattatccca aagctctgtc aattagctca agaaacagga     120
gaagatgaaa gtgcaagaaa tagtcgttca gctggtttga aagctctttc agcaatggta     180
tttattttat aattccacca ttgtttcaac ttttagatca caaattggtc ttgcacaaca     240
gcatgttgct tgtcagtttg tactttgaag gagagtgatt taaaaagaaa actatattta     300
agacatggta attgttatca acattagaaa tcagcactaa taggctagaa gcagcgctaa     360
acatgtttaa tattgagggg aaagattggt tgtactaaac ctagaagaaa tagtttaatc     420
atgcatccat agttagcttt ggttaagcaa agaatacact tttaggtact cgttaagact     480
taagtatccc caacattcat aacatcttac tttttttca atatatgtat tttttctttt     540
taatatcttg tcccggttgc aattcctact gccaacagat atattaagta tcttgctaca     600
gaatggtctt agttggaaag aatagatgat gttccttcca gtgatgtctt gacccttgag     660
agtcaactgg cataatcttc tggtctaaac taactctaga atgtcaaggg ggtctagctc     720
```

-continued

```
aattggttga gtaagggtgt gtgagttgtt gtaaacctct tgaccttgtc tttgattccc      780
atggataaaa aaaaactaac tctggaattg gatatacatc tatttcccat agcattttat      840
ttgtctgagc aattctagat tcttttgggg caatagctta tttctccctg gtctgatcat      900
taattgccaa gatcttccta ggtctcagcc attttttctgt ctacatagtg ccaaaaacag      960
ctacaataag aatcaatgtc ttttttgcttt agtactgtct aaagttaaat tctctgacgc     1020
ctttagaggt gccaacactt ctcttttctat ctttgttcat ttactatttt ttcctctagc     1080 attttttgtcc aacagtgggc aagtgcatct ctgctttatg gctgtcaaaa ttcaaatgat     1140
tttagattat cttctatttt tatcttcaat ggtccaataa tttcttgagc ttgccctagt     1200
tctaagttaa tgcctaaggt aaaaataaag agtttcttt ttcttctttt tttaataatg     1260
ttatggccaa ttagcatgtt ttaggacctg tgtagtaggc aattattggc accttagttg     1320
ttcttgtttt tacattttc atttatctct ctaagttctt gcttttacat gaattctctc     1380
tctctctcac tctcactctc actcttactt tttattttat caaaaggctt tggtttctta     1440
aatttacaat gatatgttaa attctatttc ttttccatt cgcttgcttt ggggttggat     1500
acaatgatat gttaaattta caaagatgct ggaatgaaat ggattatcat ttctgttgta     1560
tttcctgctt tctcagtaaa tctatctcct ttcttcacct taatataat ctatatactc     1620 atccttttga gttaaatgaa ctatttgct ctgtaggttc ggtttatggg tgaacaatct     1680
cacatatcag tcgaatttga taatgtaagt gattttttta cttcttcaat tgtatgaata     1740
cttacatagt ttttctaggt ggttgcatca acttgtaaac atactatttt ggttgtcttc     1800
ttatttttct ccaaatactt actacctccg gtcctattta taaaaaaaca agtgacagtg     1860
tattgtgtat tgtcacttgt ttcttatccc aatatgcatt atgtctacat tctgtaaaaa     1920
atgtcatatc aaattatgtg tactgtttca ctcctttcag ataagtttag tgtggctttt     1980
tcattgtcat tgtatcctca tataatttt atattgatgt taataaataa aaaatacttc     2040
cttcggttta taagaaacag atgactaatt catcaagacc gatgaaaata atttagttag     2100 cttttaattaa taaatgttat aaatttaaat tttatttctg aaatacccat agaattaaat     2160
gatttaacgg gtagttatat ttaatgacac tacttgtaat tcaagagata aatttttcca     2220
ccaatgagtg tgacttacac tgttaatggg tcaatgaatg cattcacttg catgagaagt     2280
aatgtctcat taatagactt tataataaat taagaaaata aaaggaaatt agaaattaat     2340
acatttaaat gtgggtccat gtgtcttaca attaggacaa taaaactcac ccatttgatt     2400
tttatataaa ggactggagg gagtgttaaa catgttgttt gatgtatagt gaaaatttct     2460
ctctatttca ttatagattg tttctgctgt cttggaaaac tatgaagttc ctaagaaaaa     2520
ttcagcaaac ctggatcatg aggaacaaga tgtgatggcc aatgagggtc aaatctctcc     2580
tttgctggat gtcaaaagga gaaaccctc ctggagaaaa gttgttaacg ataaaggcga     2640
aataaatgta gcaatgtaat tacttttatc agcagaaaat ctttgaaatg gatttatgat     2700
atcttctatt catttcatta cctttattgt tcataaattc atgcagggaa gatgacatga     2760
atccctcttt ttggtctgga gtttgcctac ataatatggc caatttagcc aaggagggga     2820
ctaccatacg tcgtgtaatg gaatctttat tccggtactt tgataatgga aacttatggt     2880
ctataaacca tggccttgcc ttttctgttt taaaggatat gctatttttg atggatgact     2940
ctggtacact tactttctta tttgatcata aaattctctt gtatcatata atctttttatt     3000 aattactcct cttctgtttc ctctttcatt ttccctccct cttgttgcag agaaaaacac     3060
acatgttttg ctgtcgacgt taattaag                                         3088
```

```
<210> SEQ ID NO 2
<211> LENGTH: 785
<212> TYPE: DNA
<213> ORGANISM: Artificial Sequence
<220> FEATURE:
<223> OTHER INFORMATION: The 3' flanking border sequence for the subject
      soybean Event pDAB8291.45.36.2

<400> SEQUENCE: 2
attgttgagg ttgccacttc acttgcccca tatgcaaaag tccaaccttc tgtatcaata      60
gttggtgcag taagtgacat gatgagacat ttgcggaagt gcatacactg ttccctggat     120
gactcaaatc tggcccctga tgtaatcaat tggaacaaga atttcaaaaa agttgtggat     180
aggtgccttg tacagttgtc aaataaggta agtcactttt cccacagttt tcatacttaa     240
acttgcagaa taactgaacc ataaatgctt tggacgattg atttgttttg cattttttt      300 tgtctttcaa atttggataa agttacaata tatgcaaagc tgtcattcaa tattagattt     360
atcataaaag tataggaaga gacctaatct gatactcatg aacaggttgg agaagcagat     420
cccattcttg atgttatggc cgtgatgcta gagaacatct caactatcac aacaatatct     480
agaaccacag tctatgctgt tcatcggacc gctcaaattg tagcctcctt accaaatgtg     540
tcctatcaga ataaggcaag gagtggatat tcctggtttt gttctttcct ctatggttca     600
ctactttgac tttttatgga taaatttgag actaaaaccc tacatttctc cccaggcatt     660
ccctgagacc ttgtttcatc aactactcct ggctatggtc catccagatc acgaaacacg     720
agtggtatct caccacatct tttccagtat tcttgtgcca acatctgttt tccctcatcc     780
aagct                                                                 785

<210> SEQ ID NO 3
<211> LENGTH: 27
<212> TYPE: DNA
<213> ORGANISM: Artificial Sequence
<220> FEATURE:
<223> OTHER INFORMATION: Primer 4536_WF1

<400> SEQUENCE: 3
cggtttatgg gtgaacaatc tcacata                                          27

<210> SEQ ID NO 4
<211> LENGTH: 26
<212> TYPE: DNA
<213> ORGANISM: Artificial Sequence
<220> FEATURE:
<223> OTHER INFORMATION: Primer 4536_WF2

<400> SEQUENCE: 4
gggtgaacaa tctcacatat cagtcg                                           26

<210> SEQ ID NO 5
<211> LENGTH: 28
<212> TYPE: DNA
<213> ORGANISM: Artificial Sequence
<220> FEATURE:
<223> OTHER INFORMATION: Primer 4536_WF3

<400> SEQUENCE: 5
tttaaatgtg ggtccatgtg tcttacaa                                         28

<210> SEQ ID NO 6
<211> LENGTH: 28
```

```
<212> TYPE: DNA
<213> ORGANISM: Artificial Sequence
<220> FEATURE:
<223> OTHER INFORMATION: Primer 4536_WF4

<400> SEQUENCE: 6
aatttagcca aggaggggac taccatac                                    28

<210> SEQ ID NO 7
<211> LENGTH: 28
<212> TYPE: DNA
<213> ORGANISM: Artificial Sequence
<220> FEATURE:
<223> OTHER INFORMATION: Primer 4536_WR1

<400> SEQUENCE: 7
gcaggcatat ttccaggaga taaagact                                    28

<210> SEQ ID NO 8
<211> LENGTH: 25
<212> TYPE: DNA
<213> ORGANISM: Artificial Sequence
<220> FEATURE:
<223> OTHER INFORMATION: Primer 4536_WR2

<400> SEQUENCE: 8
ataaagactg tgcccaaatt gacga                                       25

<210> SEQ ID NO 9
<211> LENGTH: 28
<212> TYPE: DNA
<213> ORGANISM: Artificial Sequence
<220> FEATURE:
<223> OTHER INFORMATION: Primer 4536_WR3

<400> SEQUENCE: 9
cgtccaaagc atttatggtt cagttatt                                    28

<210> SEQ ID NO 10
<211> LENGTH: 25
<212> TYPE: DNA
<213> ORGANISM: Artificial Sequence
<220> FEATURE:
<223> OTHER INFORMATION: Primer 4536_WR4

<400> SEQUENCE: 10
ggacacattt ggtaaggagg ctaca                                       25

<210> SEQ ID NO 11
<211> LENGTH: 25
<212> TYPE: DNA
<213> ORGANISM: Artificial Sequence
<220> FEATURE:
<223> OTHER INFORMATION: Primer ED_v2_C1

<400> SEQUENCE: 11
agtttgctga ggtgcttgag atgat                                       25

<210> SEQ ID NO 12
<211> LENGTH: 24
<212> TYPE: DNA
<213> ORGANISM: Artificial Sequence
<220> FEATURE:
<223> OTHER INFORMATION: Primer PAT_11

<400> SEQUENCE: 12
```

```
acagagccac aaacaccaca agag                                            24
```

<210> SEQ ID NO 13
<211> LENGTH: 10268
<212> TYPE: DNA
<213> ORGANISM: Artificial Sequence
<220> FEATURE:
<223> OTHER INFORMATION: Plasmid pDAB8291

<400> SEQUENCE: 13

```
agtcagcatc atcacaccaa aagttaggcc cgaatagttt gaaattagaa agctcgcaat      60
tgaggtctac aggccaaatt cgctcttagc cgtacaatat tactcaccgg atcctaaccg     120
gtgtgatcat gggccgcgat taaaaatctc aattatattt ggtctaattt agtttggtat     180
tgagtaaaac aaattcgaac caaaccaaaa tataaatata tagttttttat atatatgcct     240
ttaagacttt ttatagaatt ttctttaaaa aatatctaga aatatttgcg actcttctgg     300
catgtaatat ttcgttaaat atgaagtgct ccattttatt taactttaaa taattggttg     360
tacgatcact ttcttatcaa gtgttactaa aatgcgtcaa tctctttgtt cttccatatt     420
catatgtcaa aacctatcaa aattcttata tatcttttct gaatttgaag tgaaatttcg     480
ataatttaaa attaaataga acatatcatt atttaggtat catattgatt tttatactta     540
attactaaat ttggttaact ttgaaagtgt acatcaacga aaaattagtc aaacgactaa     600
aataaataaa tatcatgtgt tattaagaaa attctcctat aagaatattt taatagatca     660
tatgtttgta aaaaaaatta atttttacta acacatatat ttacttatca aaaatttgac     720
aaagtaagat taaaataata ttcatctaac aaaaaaaaaa ccagaaaatg ctgaaacccc     780
ggcaaaaccg aaccaatcca aaccgatata gttggtttgg tttgattttg atataaaccg     840
aaccaactcg gtccatttgc acccctaatc ataaatagctt taatatttca agatattatt     900
aagttaacgt tgtcaatatc ctggaaattt tgcaaaatga atcaagccta tatggctgta     960
atatgaattt aaaagcagct cgatgtggtg gtaaatatga atttacttga ttctaaaaaa    1020
atatcccaag tattaataat ttctgctagg aagaaggtta gctacgattt acagcaaagc    1080
cagaatacaa tgaaccataa agtgattgaa gctcgaaata tacgaaggaa caaatatttt    1140
taaaaaaata cgcaatgact tggaacaaaa gaaagtgata tatttttttgt tcttaaacaa    1200
gcatcccctc taaagaatgg cagttttcct ttgcatgtaa ctattatgct cccttcgtta    1260
caaaaatttt ggactactat tgggaacttc ttctgaaaat agtggccacc gcttaattaa    1320
ggcgcgccga cgaatgtccc cgatcaaatc tgagggacgt taaagcgatg ataaattgga    1380
accagaatat agaatctttg ttctgctcta gcttttcttc tgtacatttt ttacgattag    1440
actatgattt tcattcaata accaaaattc tgaagtttgt catcaagttg ctcaatcaaa    1500
cttgtaccgg tttgtttcgg ttttatatca gctcactgtt acactttaac caaaatcggt    1560
ttatgtctta ataaaggaat tgagtcggtt taactcatat ccgtaccaat gcgacgtcgt    1620
gtccgcgttt cagtagcttt gctcattgtc ttctacggga actttcccgg acataggaac    1680
cgccctttcg ttatcctcat ccatcgtgaa atcaggaaat aaatgttcga agatttgagg    1740
tcaaagtcg aatttcatgt tgtctcttct atttagatac aaaattgaag cattttcac     1800
caatttaatg ccaaaattta aaacaacgct gataaagtga aacttgattc gatttatatt    1860
tcaaccgaaa ctgctgaagc aagaagaaaa agcgtaatta cacataacaa gaacgctacc    1920
gcaaactact aaacgccaaa cccaatacaa agtaaaacg cagacgctta agtgagaaac     1980
ccagaaaaca caaacgcgga tcggggatc cactagttag gtgattaagc taactactca    2040
```

```
gttcttgaca aaggtgctga gcacatcaaa gtagtctggg aaggtcttgc gagtgcaccc    2100
agggtcacgt atggtgacag ggacttctgc acaggctgca agggagaaag ccattgccat    2160
gcggtggtca tcataggtgt ctatggctgt cacgttgagc ttctcgggag gtgtgatgat    2220
gcagtagtct ggtccttcct caacgctggc tccaagtttg gtcaactctg tgcgtattgc    2280
aaccatcctc tctgtctcct tgactctcca ggaagccaca tctctgatgg ctgttggtcc    2340
atcggcaaag agtgcaacca cagcaagagt catggcaaca tctggcatct tgttcatgtt    2400
gacatcaatg gctttgagat gtttccttcc gaatggctcc cttggaggtc cagtcactgt    2460
gacgagggtt tcagtccagg tgaccttttgc tcccatcatc tcaagcacct cagcaaactt   2520
cacatcacct tgcaagctgg tagtgccaca accttccact gtcacagtcc ctccagtgat    2580
tgcagcacca gccaagaagt agctggcaga gctggcatca ccttcaacat aggcattctt    2640
gggtgacttg tacttctgac ctcccttgat gtagaatctg tcccagctgt cagaatgctc    2700
agctttcaca ccaaaccttt ccatcaatct caaggtcatc tccacatagg gaatggagat    2760
gagtttgtca atgatctcaa tctccacatc accaagagcc aagggagctg ccatgagcaa    2820
ggctgacaag tactgggagc tgatggagcc agagagcttg accttgccac cagggagacc    2880
tccaatccca ttgacacgaa caggtggaca gtcggtgcca aggaagcagt caacatcagc    2940
tccaagttgc ttcaagccaa ccaccaagtc gccaatgggt ctctccctca tgcgtggcac    3000
gccatcaaga acataggtgg cattcccacc agctgcagtg acagctgcag tcaaggatct    3060
catggcaatc ccagcattcc caaggaagag ctggacttcc tctttggcat cttcaactgg    3120
gaactttcca ccacagccaa ccacaacagc acgcttggca gctttgtctg cttcaacaga    3180
caagccaaga gtcctcaagg ctccgagcat gtagtggaca tcctctgagt tgagaaggtt    3240
gtcaaccact gtggtccctt cagaaagagc tgcaagcaag aggatacggt ttgaaagtga    3300
cttgagccca gggagtttga ctgtgccaga gatctccttg atgggctgca gcacgatctc    3360
ctcggcgccg gccatgcacc ggatccttcc gccgttgctg acgttgccga ggcttctgga    3420
ggagcggcgg gcgacgggga ggctggcggt ggacttgagc ccctggaacg gagcgacggc    3480
ggtggccgac gaggccatca tcacggtggg cgccatagac agcggcggca ggtacgacag    3540
cgtctcgaac ttcttgttgc cgtaggccgg ccacacctgc atacattgaa ctcttccacc    3600
gttgctggga agggtggaga agtcgttagc cttcttggtg gtggggaagg cggcgttgga    3660
cttaaggccg gtgaacggag ccaccatgtt ggcctgagca ggggcggtcc ggctaacggt    3720
cgcgactgag gaggagatcg aagccatggg gatctgcgca tttaacaaga aattgaacag    3780
tcaattgggg attttcatta tccataacta aattttgaag aaattggaat actaaacgtc    3840
accacttaaa accctaatcc agtgaatcg ttatcgaacc agatataacc aaaaggggca     3900
aaattgactc gaaaacccta gttctcgata cacggctagg taatgacaat cgcacacaga    3960
caaatctggt tatacagaac ttcgaagcaa gaaaaaaacg atgaagaatg gatcatccaa    4020
taaatcgact agactcaatc ttcacaggtt tatcgatcca gcaaacttaa aagacggacc    4080
tttattttca aactggaatg ggacaaaacc cgaaactcta ttgtcgtaaa atcagatcgc    4140
ggagacagta acagaaaaaa cattaaaaag taatggaaag acctaaaccc ctgatctaat    4200
tacaaacaaa tcatacctgt tcttcgcctg aggggttcga aatcgataag cttggatcct    4260
ctagagtcga gagaaattga tgtctgtaga agaagaagaa cggttaagag tagatttggg    4320
tgagaaagat gtgaaattgt ttttataggc aaagacggag agtctatttt ttgagcaatc    4380
```

```
agatcgcata ttaaatctaa cggctgagat atcgatccgt gtgtacaata aaatgatgta    4440
taaaccgtcg atctgtttta atcgacggtt catattagtg atccgcgtga tggcagtgat    4500
agccactaag aatcgtcttt tgttttacat gtggcgccac aaattagggt aatgaagcgg    4560
caatattttg gaactcggaa aataaaattg cgccatcaca ttatttgaaa attttcacat    4620
gcttttattt taaaaaccca cgaattacaa gttacaaccg aaaagatttt ataatatagt    4680
gatttatact aattttgtag tagcttaatg tatattgata ctggaaaaac aatgacaatc    4740
atatgttagt attatcaagt tatcgtattg atattgatat tggaacatac aatgggtatt    4800 gccttcttc gaccataaat atcaccaaat ttacaaagtt tgtgtatacc aagttatcaa    4860
ttgtaaatgg gatgtcaaca ttttaatttc cctttgagaa actatagacc acaagaacac    4920
acttcaatag ataaagtaac tatttacata agaggtttta aaatcacatt aacaaaaata    4980 attccaacc ggcactcaca aatacaaaca gagcacacga catgtcaaag ccacaagtaa    5040
attcgttgag tggtggtttc attacaattg tgtcacttgc agcacaaact atcttgctct    5100
gggaatcatc tcagcatcaa agatcatgct cacttcaggg gaacttagtg tatccatgcc    5160
tcgactcata tttctcctcg acatgcatcc tgcagggggcg cgccatgccc gggcaagcgg    5220
ccgcacaagt ttgtacaaaa aagcaggctc cgcggtgact gactgaaaag cttgtcgacc    5280
tgcaggtcaa cggatcagga tattcttgtt taagatgttg aactctatgg aggtttgtat    5340
gaactgatga tctaggaccg gataagttcc cttcttcata gcaacttat tcaaagaatg    5400 ttttgtgtat cattcttgtt acattgttat taatgaaaaa atattattgg tcattggact    5460
gaacacgagt gttaaatatg gaccaggccc caaataagat ccattgatat atgaattaaa    5520
taacaagaat aaatcgagtc accaaaccac ttgcctttt taacgagact tgttcaccaa    5580
cttgatacaa aagtcattat cctatgcaaa tcaataatca tacaaaaata tccaataaca    5640 ctaaaaatt aaaagaaatg gataatttca caatatgtta tacgataaag aagttacttt    5700
tccaagaaat tcactgattt tataagccca cttgcattag ataaatggca aaaaaaaaca    5760 aaaggaaaa gaaataaagc acgaagaatt ctagaaaata cgaaatacgc ttcaatgcag    5820
tgggacccac ggttcaatta ttgccaattt tcagctccac cgtatattta aaaaataaaa    5880
cgataatgct aaaaaaatat aaatcgtaac gatcgttaaa tctcaacggc tggatcttat    5940
gacgaccgtt agaaattgtg gttgtcgacg agtcagtaat aaacggcgtc aaagtggttg    6000
cagccggcac acacgagtcg tgtttatcaa ctcaaagcac aaatactttt cctcaaccta    6060
aaaataaggc aattagccaa aaacaacttt gcgtgtaaac aacgctcaat acacgtgtca    6120
ttttattatt agctattgct tcaccgcctt agctttctcg tgacctagtc gtcctcgtct    6180
tttcttcttc ttcttctata aaacaatacc caaagcttct tcttcacaat tcagatttca    6240
atttctcaaa atcttaaaaa cttctctctca attctctcta ccgtgatcaa ggtaaatttc    6300
tgtgttcctt attctctcaa aatcttgat tttgttttcg ttcgatccca atttcgtata    6360
tgttctttgg tttagattct gttaatctta gatcgaagac gattttctgg gtttgatcgt    6420
tagatatcat cttaattctc gattagggtt tcataaatat catccgattt gttcaaataa    6480
tttgagtttt gtcgaataat tactcttcga tttgtgattt ctatctagat ctggtgttag    6540
tttctagttt gtgcgatcga atttgtcgat taatctgagt ttttctgatt aacagagatc    6600
tccatggctc agaccactct ccaaatcaca cccactggtg ccaccttggg tgccacagtc    6660
actggtgttc accttgccac acttgacgat gctggtttcg ctgccctcca tgcagcctgg    6720
cttcaacatg cactcttgat cttccctggg caacacctca gcaatgacca acagattacc    6780
```

```
tttgctaaac gctttggagc aattgagagg attggcggag gtgacattgt tgccatatcc   6840
aatgtcaagg cagatggcac agtgcgccag cactctcctg ctgagtggga tgacatgatg   6900
aaggtcattg tgggcaacat ggcctggcac gccgactcaa cctacatgcc agtcatggct   6960
caaggagctg tgttcagcgc agaagttgtc ccagcagttg ggggcagaac ctgctttgct   7020
gacatgaggg cagcctacga tgcccttgat gaggcaaccc gtgctcttgt tcaccaaagg   7080
tctgctcgtc actcccttgt gtattctcag agcaagttgg gacatgtcca acaggccggg   7140
tcagcctaca taggttatgg catggacacc actgcaactc ctctcagacc attggtcaag   7200
gtgcatcctg agactggaag gcccagcctc ttgatcggcc gccatgccca tgccatccct   7260
ggcatggatg cagctgaatc agagcgcttc cttgaaggac ttgttgactg ggcctgccag   7320
gctcccagag tccatgctca ccaatgggct gctggagatg tggttgtgtg ggacaaccgc   7380
tgtttgctcc accgtgctga gccctgggat ttcaagttgc cacgtgtgat gtggcactcc   7440
agactcgctg gacgcccaga aactgagggt gctgccttgg tttgagtagt tagcttaatc   7500
acctagagct cggtcaccag cataattttt attaatgtac taaattactg ttttgttaaa   7560
tgcaattttg ctttctcggg attttaatat caaaatctat ttagaaatac acaatatttt   7620
gttgcaggct tgctggagaa tcgatctgct atcataaaaa ttacaaaaaa attttatttg   7680
cctcaattat tttaggattg gtattaagga cgcttaaatt atttgtcggg tcactacgca   7740
tcattgtgat tgagaagatc agcgatacga aatattcgta gtactatcga taatttatt   7800 gaaaattcat aagaaaagca aacgttacat gaattgatga aacaatacaa agacagataa   7860
agccacgcac atttaggata ttggccgaga ttactgaata ttgagtaaga tcacggaatt   7920
tctgacagga gcatgtcttc aattcagccc aaatggcagt tgaaatactc aaaccgcccc   7980
atatgcagga gcggatcatt cattgtttgt ttggttgcct ttgccaacat gggagtccaa   8040
ggttgcggcc gcgcgccgac ccagcttttct tgtacaaagt ggttgcggcc gcttaattaa   8100
atttaaatgc ccgggcgttt aaacgcggcc gcttaattaa ggccggcctg cagcaaaccc   8160
agaaggtaat tatccaagat gtagcatcaa gaatccaatg tttacgggaa aaactatgga   8220
agtattatgt aagctcagca agaagcagat caatatgcgg cacatatgca acctatgttc   8280
aaaaatgaag aatgtacaga tacaagatcc tatactgcca gaatacgaag aagaatacgt   8340
agaaattgaa aagaagaaac caggcgaaga aaagaatctt gaagacgtaa gcactgacga   8400
caacaatgaa aagaagaaga taaggtcggt gattgtgaaa gagacataga ggacacatgt   8460
aaggtggaaa atgtaagggc ggaaagtaac cttatcacaa aggaatctta tcccccacta   8520
cttatccttt tatattttc cgtgtcattt ttgcccttga gttttcctat ataaggaacc   8580
aagttcggca tttgtgaaaa caagaaaaaa tttggtgtaa gctatttttct ttgaagtact   8640 gaggatacaa cttcagagaa atttgtaagt ttgtagatct ccatgtctcc ggagaggaga   8700
ccagttgaga ttaggccagc tacagcagct gatatggccg cggtttgtga tatcgttaac   8760
cattacattg agacgtctac agtgaacttt aggacagagc cacaaacacc acaagagtgg   8820
attgatgatc tagagaggtt gcaagataga tacccttggt tggttgctga ggttgagggt   8880
gttgtggctg gtattgctta cgctgggccc tggaaggcta ggaacgctta cgattggaca   8940
gttgagagta ctgtttacgt gtcacatagg catcaaaggt tgggcctagg atccacattg   9000
tacacacatt tgcttaagtc tatggaggcg caaggtttta agtctgtggt tgctgttata   9060
ggccttccaa acgatccatc tgttaggttg catgaggctt tgggatacac agcccggggt   9120
```

```
acattgcgcg cagctggata caagcatggt ggatggcatg atgttggttt ttggcaaagg    9180
gatttttgagt tgccagctcc tccaaggcca gttaggccag ttacccagat ctgaggtacc   9240
ctgagcttga gcttatgagc ttatgagctt agagctcgga tccactagta acggccgcca    9300
gtgtgctgga attcgccctt gactagatag gcgcccagat cggcggcaat agcttcttag    9360
cgccatcccg ggttgatcct atctgtgttg aaatagttgc ggtgggcaag gctctctttc    9420
agaaagacag gcggccaaag gaacccaagg tgaggtgggc tatggctctc agttccttgt    9480
ggaagcgctt ggtctaaggt gcagaggtgt tagcgggatg aagcaaaagt gtccgattgt    9540
aacaagatat gttgatccta cgtaaggata ttaaagtatg tattcatcac taatataatc    9600
agtgtattcc aatatgtact acgatttcca atgtctttat tgtcgccgta tgtaatcggc    9660
gtcacaaaat aatccccggt gactttcttt taatccagga tgaaataata tgttattata    9720
attttttgcga tttggtccgt tataggaatt gaagtgtgct tgcggtcgcc accactccca   9780
tttcataatt ttacatgtat ttgaaaaata aaaatttatg gtattcaatt taaacacgta    9840
tacttgtaaa gaatgatatc ttgaaagaaa tatagtttaa atatttattg ataaaataac    9900
aagtcaggta ttatagtcca agcaaaaaca taaatttatt gatgcaagtt taaattcaga    9960
aatatttcaa taactgatta tatcagctgg tacattgccg tagatgaaag actgagtgcg   10020
atattatggt gtaatacata gcggccgggt ttctagtcac cggttaggat ccgtttaaac   10080
tcgaggctag cgcatgcaca tagacacaca catcatctca ttgatgcttg gtaataattg   10140
tcattagatt gttttttatgc atagatgcac tcgaaatcag ccaattttag acaagtatca  10200
aacggatgtg acttcagtac attaaaaacg tccgcaatgt gttattaagt tgtctaagcg   10260
tcaatttg                                                             10268

<210> SEQ ID NO 14
<211> LENGTH: 3406
<212> TYPE: DNA
<213> ORGANISM: Artificial Sequence
<220> FEATURE:
<223> OTHER INFORMATION: Part of the 5' soybean genomic flanking and
      part of the 5' insert sequence

<400> SEQUENCE: 14
agctttgact ggaaaaacat gagcctacat attttttata ttttgcagat tgatggaagt      60
tacctgttca acttagaagg tattatccca aagctctgtc aattagctca agaaacagga    120
gaagatgaaa gtgcaagaaa tagtcgttca gctggtttga aagctctttc agcaatggta    180
tttatttat aattccacca ttgtttcaac ttttagatca caaattggtc ttgcacaaca     240
gcatgttgct tgtcagtttg tactttgaag gagagtgatt taaaaagaaa actatattta    300
agacatggta attgttatca acattagaaa tcagcactaa taggctagaa gcagcgctaa    360
acatgtttaa tattgagggg aaagattggt tgtactaaac ctagaagaaa tagtttaatc    420
atgcatccat agttagcttt ggttaagcaa agaatacact tttaggtact cgttaagact    480
taagtatccc caacattcat aacatcttac tttttttttca atatatgtat ttttttcttt   540
taatatcttg tcccggttgc aattcctact gccaacagat atattaagta tcttgctaca    600
gaatggtctt agttggaaag aatagatgat gttccttcca gtgatgtctt gacccttgag    660
agtcaactgg cataatcttc tggtctaaac taactctaga atgtcaaggg ggtctagctc    720
aattggttga gtaagggtgt gtgagttgtt gtaaacctct tgaccttgtc tttgattccc    780
atggataaaa aaaaactaac tctggaattg gatatacatc tatttcccat agcattttat    840
```

-continued

```
ttgtctgagc aattctagat tcttttgggg caatagctta tttctccctg gtctgatcat   900
taattgccaa gatcttccta ggtctcagcc attttctgt ctacatagtg ccaaaaacag    960
ctacaataag aatcaatgtc ttttgctt agtactgtct aaagttaaat tctctgacgc   1020
ctttagaggt gccaacactt ctcttctat ctttgttcat ttactatttt ttcctctagc   1080
attttgtcc aacagtgggc aagtgcatct ctgctttatg gctgtcaaaa ttcaaatgat   1140
tttagattat ctttctattt tatcttcaat ggtccaataa tttcttgagc ttgccctagt   1200
tctaagttaa tgcctaaggt aaaaataaag agtttcttt tcttctttt tttaataatg    1260
ttatggccaa ttagcatgtt ttaggacctg tgtagtaggc aattattggc accttagttg   1320
ttcttgtttt tacattttc atttatctct ctaagttctt gcttttacat gaattctctc    1380
tctctctcac tctcactctc actcttactt tttattttat caaaaggctt tggtttctta   1440
aatttacaat gatatgttaa attctatttc tttttccatt cgcttgcttt ggggttggat   1500
acaatgatat gttaaattta caaagatgct ggaatgaaat ggattatcat ttctgttgta   1560
tttcctgctt tctcagtaaa tctatctcct ttcttcacct taatataat ctatatactc    1620
atccttttga gttaaatgaa ctattttgct ctgtaggttc ggtttatggg tgaacaatct   1680
cacatatcag tcgaatttga taatgtaagt gatttttta cttcttcaat tgtatgaata    1740
cttacatagt ttttctaggt ggttgcatca acttgtaaac atactatttt ggttgtcttc   1800
ttattttct ccaaatactt actacctccg gtcctattta taaaaaaaca agtgacagtg    1860
tattgtgtat tgtcacttgt ttcttatccc aatatgcatt atgtctacat tctgtaaaaa   1920
atgtcatatc aaattatgtg tactgtttca ctcctttcag ataagtttag tgtggctttt   1980
tcattgtcat tgtatcctca tatataattt atattgatgt taataaataa aaaatacttc   2040
cttcggttta taagaaacag atgactaatt catcaagacc gatgaaaata atttagttag   2100
cttaattaa taaatgttat aaatttaaat tttatttctg aaatacccat agaattaaat    2160
gatttaacgg gtagttatat ttaatgacac tacttgtaat tcaagagata aattttccca   2220
ccaatgagtg tgacttacac tgttaatggg tcaatgaatg cattcacttg catgagaagt   2280
aatgtctcat taatagactt tataatatat taagaaaata aaggaaattt agaaattaat   2340
acatttaaat gtgggtccat gtgtcttaca attaggacaa taaaactcac ccatttgatt   2400
tttatataaa ggactggagg gagtgttaaa catgttgttt gatgtatagt gaaaatttct   2460
ctctatttca ttatagattg tttctgctgt cttggaaaac tatgaagttc ctaagaaaaa   2520
ttcagcaaac ctggatcatg aggaacaaga tgtgatggcc aatgagggtc aaatctctcc   2580
tttgctggat gtcaaaagga gaaacccttc ctggagaaaa gttgttaacg ataaaggcga   2640
aataaatgta gcaatgtaat tacttttatc agcagaaaat ctttgaaatg gatttatgat   2700
atcttctatt catttcatta cctttattgt tcataaattc atgcagggaa gatgacatga   2760
atccctcttt ttggtctgga gtttgcctac ataatatggc caatttagcc aaggagggga   2820
ctaccatacg tcgtgtaatg gaatctttat tccggtactt tgataatgga aacttatggt   2880
ctataaacca tggccttgcc ttttctgttt taaaggatat gctattttg atggatgact    2940
ctggtacact tactttctta tttgatcata aaattctctt gtatcatata atcttttatt   3000
aattactcct cttctgtttc ctctttcatt ttccctccct cttgttgcag agaaaaacac   3060
acatgttttg ctgtcgacgt taattaagag tcagcatcat cacaccaaaa gttaggcccg   3120
aatagtttga aattagaaag ctcgcaattg aggtctacag gccaaattcg ctcttagccg   3180
tacaatatta ctcaccggat cctaaccggt gtgatcatgg gccgcgatta aaaatctcaa   3240
```

```
ttatatttgg tctaatttag tttggtattg agtaaaacaa attcgaacca aaccaaaata        3300
taaatatata gtttttatat atatgccttt aagactttt atagaatttt ctttaaaaaa          3360
tatctagaaa tatttgcgac tcttctggca tgtaatattt cgttaa                       3406
```

<210> SEQ ID NO 15
<211> LENGTH: 1008
<212> TYPE: DNA
<213> ORGANISM: Artificial Sequence
<220> FEATURE:
<223> OTHER INFORMATION: Part of the 3' soybean genomic flanking and
      part of the 3' insert sequence

<400> SEQUENCE: 15

```
gcacatagac acacacatca tctcattgat gcttggtaat aattgtcatt agattgtttt         60
tatgcataga tgcactcgaa atcagccaat tttagacaag tatcaaacgg atgtgacttc        120
agtacattaa aaacgtccgc aatgtgttat taagttgtct aagcgtcaat ttgatttaca        180
attgaatata tcctgcccca gccagccaac agctcgattt acaattgttg aggttgccac        240
ttcacttgcc ccatatgcaa aagtccaacc ttctgtatca atagttggtg cagtaagtga        300
catgatgaga catttgcgga agtgcataca ctgttccctg gatgactcaa atctggcccc        360
tgatgtaatc aattggaaca agaatttcaa aaaagttgtg gataggtgcc ttgtacagtt        420
gtcaaataag gtaagtcact tttcccacag ttttcatact taaacttgca gaataactga        480
accataaatg ctttggacga ttgatttgtt ttgcattttt ttttgtcttt caaatttgga        540
taaagttaca atatatgcaa agctgtcatt caatattaga tttatcataa aagtatagga        600
agagacctaa tctgatactc atgaacaggt tggagaagca gatcccattc ttgatgttat        660
ggccgtgatg ctagagaaca tctcaactat cacaacaata tctagaacca cagtctatgc        720
tgttcatcgg accgctcaaa ttgtagcctc cttaccaaat gtgtcctatc agaataaggc        780
aaggagtgga tattcctggt tttgttcttt cctctatggt tcactacttt gacttttttat       840 ggataaattt gagactaaaa ccctacattt ctccccaggc attccctgag accttgtttc        900
atcaactact cctggctatg gtccatccag atcacgaaac acgagtggta tctcaccaca        960
tcttttccag tattcttgtg ccaacatctg tttttcccctca tccaagct                  1008
```

<210> SEQ ID NO 16
<211> LENGTH: 72
<212> TYPE: DNA
<213> ORGANISM: Artificial Sequence
<220> FEATURE:
<223> OTHER INFORMATION: A 72 base pair sequence spanning the 5'
      integration junction

<400> SEQUENCE: 16

```
acatgttttg ctgtcgacgt taattaagag tcagcatcat cacaccaaaa gttaggcccg         60
aatagtttga aa                                                             72
```

<210> SEQ ID NO 17
<211> LENGTH: 142
<212> TYPE: DNA
<213> ORGANISM: Artificial Sequence
<220> FEATURE:
<223> OTHER INFORMATION: A 142 base pair sequence spanning the 3'
      integration junction

<400> SEQUENCE: 17

```
cgtccgcaat gtgttattaa gttgtctaag cgtcaatttg atttacaatt gaatatatcc         60
```
tgccccagcc agccaacagc tcgatttaca attgttgagg ttgccacttc acttgcccca        120
tatgcaaaag tccaaccttc tg                                                 142

<210> SEQ ID NO 18
<211> LENGTH: 23
<212> TYPE: DNA
<213> ORGANISM: Artificial Sequence
<220> FEATURE:
<223> OTHER INFORMATION: Primer 4536_5'F

<400> SEQUENCE: 18
acatgttttg ctgtcgacgt taa                                                 23

<210> SEQ ID NO 19
<211> LENGTH: 24
<212> TYPE: DNA
<213> ORGANISM: Artificial Sequence
<220> FEATURE:
<223> OTHER INFORMATION: Primer 4536_5'R

<400> SEQUENCE: 19
tttcaaacta ttcgggccta actt                                                24

<210> SEQ ID NO 20
<211> LENGTH: 16
<212> TYPE: DNA
<213> ORGANISM: Artificial Sequence
<220> FEATURE:
<223> OTHER INFORMATION: Probe 4536_5'P

<400> SEQUENCE: 20
aagagtcagc atcatc                                                         16

<210> SEQ ID NO 21
<211> LENGTH: 24
<212> TYPE: DNA
<213> ORGANISM: Artificial Sequence
<220> FEATURE:
<223> OTHER INFORMATION: Primer 4536_3'F

<400> SEQUENCE: 21
cgtccgcaat gtgttattaa gttg                                                24

<210> SEQ ID NO 22
<211> LENGTH: 24
<212> TYPE: DNA
<213> ORGANISM: Artificial Sequence
<220> FEATURE:
<223> OTHER INFORMATION: Primer 4536_3'R

<400> SEQUENCE: 22
cagaaggttg gacttttgca tatg                                                24

<210> SEQ ID NO 23
<211> LENGTH: 17
<212> TYPE: DNA
<213> ORGANISM: Artificial Sequence
<220> FEATURE:
<223> OTHER INFORMATION: Probe 4536_3'P

<400> SEQUENCE: 23
caattgttga ggttgcc                                                        17

<210> SEQ ID NO 24

```
<211> LENGTH: 24
<212> TYPE: DNA
<213> ORGANISM: Artificial Sequence
<220> FEATURE:
<223> OTHER INFORMATION: Primer GMS116F

<400> SEQUENCE: 24
gtaatatggg ctcagaggaa tggt                                          24

<210> SEQ ID NO 25
<211> LENGTH: 23
<212> TYPE: DNA
<213> ORGANISM: Artificial Sequence
<220> FEATURE:
<223> OTHER INFORMATION: Primer GMS116R

<400> SEQUENCE: 25
atggagaaga acattggaat tgc                                           23

<210> SEQ ID NO 26
<211> LENGTH: 23
<212> TYPE: DNA
<213> ORGANISM: Artificial Sequence
<220> FEATURE:
<223> OTHER INFORMATION: Probe GMS116Probe

<400> SEQUENCE: 26
ccatggcccg gtaccatctg gtc                                           23

<210> SEQ ID NO 27
<211> LENGTH: 14191
<212> TYPE: DNA
<213> ORGANISM: Artificial Sequence
<220> FEATURE:
<223> OTHER INFORMATION: Expected Sequence of Soybean Event
      pDAB8291.45.36.2

<400> SEQUENCE: 27
agcttggatg agggaaaaca gatgttggca caagaatact ggaaaagatg tggtgagata    60
ccactcgtgt ttcgtgatct ggatggacca tagccaggag tagttgatga acaaggtct    120 cagggaatgc ctggggagaa atgtagggtt ttagtctcaa atttatccat aaaaagtcaa   180
agtagtgaac catagaggaa agaacaaaac caggaatatc cactccttgc cttattctga   240
taggacacat ttggtaagga ggctacaatt tgagcggtcc gatgaacagc atagactgtg   300
gttctagata ttgttgtgat agttgagatg ttctctagca tcacggccat aacatcaaga   360
atgggatctg cttctccaac ctgttcatga gtatcagatt aggtctcttc ctatactttt   420
atgataaatc taatattgaa tgacagcttt gcatatattg taactttatc caaatttgaa   480
agacaaaaaa aaatgcaaaa caaatcaatc gtccaaagca tttatggttc agttattctg   540
caagtttaag tatgaaaact gtgggaaaag tgacttacct tatttgacaa ctgtacaagg   600
cacctatcca caactttttt gaaattcttg ttccaattga ttacatcagg ggccagattt   660
gagtcatcca gggaacagtg tatgcacttc cgcaaatgtc tcatcatgtc acttactgca   720
ccaactattg atacagaagg ttggactttt gcatatgggg caagtgaagt ggcaacctca   780
acaattgtaa atcgagctgt tggctggctg gggcaggata tattcaattg taaatcaaat   840
tgacgcttag acaacttaat aacacattgc ggacgttttt aatgtactga agtcacatcc   900
gtttgatact tgtctaaaat tggctgattt cgagtgcatc tatgcataaa acaatctaa    960 tgacaattat taccaagcat caatgagatg atgtgtgtgt ctatgtgcat gcgctagcct  1020
```

```
cgagtttaaa cggatcctaa ccggtgacta gaaacccggc cgctatgtat tacaccataa    1080
tatcgcactc agtctttcat ctacggcaat gtaccagctg atataatcag ttattgaaat    1140
atttctgaat ttaaacttgc atcaataaat ttatgttttt gcttggacta taatacctga    1200
cttgttattt tatcaataaa tatttaaact atatttcttt caagatatca ttctttacaa    1260
gtatacgtgt ttaaattgaa taccataaat ttttattttt caaatacatg taaaattatg    1320
aaatgggagt ggtggcgacc gcaagcacac ttcaattcct ataacggacc aaatcgcaaa    1380
aattataata acatattatt tcatcctgga ttaaaagaaa gtcaccgggg attattttgt    1440
gacgccgatt acatacggcg acaataaaga cattggaaat cgtagtacat attggaatac    1500
actgattata ttagtgatga atacatactt taatatcctt acgtaggatc aacatatctt    1560
gttacaatcg dacacttttg cttcatcccg ctaacacctc tgcaccttag accaagcgct    1620
tccacaagga actgagagcc atagcccacc tcaccttggg ttcctttggc cgcctgtctt    1680
tctgaaagag agccttgccc accgcaacta tttcaacaca gataggatca acccgggatg    1740
gcgctaagaa gctattgccg ccgatctggg cgcctatcta gtcaagggcg aattccagca    1800
cactggcggc cgttactagt ggatccgagc tctaagctca taagctcata agctcaagct    1860
cagggtacct cagatctggg taactggcct aactggcctt ggaggagctg gcaactcaaa    1920
atccctttgc caaaaaccaa catcatgcca tccaccatgc ttgtatccag ctgcgcgcaa    1980
tgtaccccgg gctgtgtatc ccaaagcctc atgcaaccta acagatggat cgtttggaag    2040
gcctataaca gcaaccacag acttaaaacc ttgcgcctcc atagacttaa gcaaatgtgt    2100
gtacaatgtg gatcctaggc ccaacctttg atgcctatgt gacacgtaaa cagtactctc    2160
aactgtccaa tcgtaagcgt tcctagcctt ccagggccca gcgtaagcaa taccagccac    2220
aacaccctca acctcagcaa ccaaccaagg gtatctatct tgcaacctct ctagatcatc    2280
aatccactct tgtggtgttt gtggctctgt cctaaagttc actgtagacg tctcaatgta    2340
atggttaacg atatcacaaa ccgcggccat atcagctgct gtagctggcc taatctcaac    2400
tggtctcctc tccggagaca tggagatcta caaacttaca aatttctctg aagttgtatc    2460
ctcagtactt caaagaaaat agcttacacc aaatttttc ttgttttcac aaatgccgaa    2520
cttggttcct tatataggaa aactcaaggg caaaatgac acggaaaaat ataaaaggat    2580
aagtagtggg ggataagatt cctttgtgat aaggttactt tccgccctta cattttccac    2640
cttacatgtg tcctctatgt ctctttcaca atcaccgacc ttatcttctt cttttcattg    2700
ttgtcgtcag tgcttacgtc ttcaagattc ttttcttcgc ctggttcttc ttttcaatt    2760 tctacgtatt cttcttcgta ttctggcagt ataggatctt gtatctgtac attcttcatt    2820
tttgaacata ggttgcatat gtgccgcata ttgatctgct tcttgctgag cttacataat    2880
acttccatag ttttttcccgt aaacattgga ttcttgatgc tacatcttgg ataattacct    2940
tctgggtttg ctgcaggccg gccttaatta agcggccgcg tttaaacgcc cgggcattta    3000
aatttaatta agcggccgca accactttgt acaagaaagc tgggtcggcg cgcggccgca    3060
accttggact cccatgttgg caaaggcaac caaacaaaca atgaatgatc cgctcctgca    3120 tatgggcgg tttgagtatt tcaactgcca tttgggctga attgaagaca tgctcctgtc    3180
agaaattccg tgatcttact caatattcag taatctcggc caatatccta aatgtgcgtg    3240
gctttatctg tctttgtatt gtttcatcaa ttcatgtaac gtttgctttt cttatgaatt    3300
ttcaaataaa ttatcgatag tactacgaat atttcgtatc gctgatcttc tcaatcacaa    3360
tgatgcgtag tgacccgaca aataatttaa gcgtccttaa taccaatcct aaaataattg    3420
```

```
aggcaaataa aatttttttg taatttttat gatagcagat cgattctcca gcaagcctgc   3480
aacaaaatat tgtgtatttc taaatagatt ttgatattaa aatcccgaga aagcaaaatt   3540
gcatttaaca aaacagtaat ttagtacatt aataaaaatt atgctggtga ccgagctcta   3600
ggtgattaag ctaactactc aaaccaaggc agcaccctca gtttctgggc gtccagcgag   3660
tctggagtgc cacatcacac gtggcaactt gaaatcccag ggctcagcac ggtggagcaa   3720
acagcggttg tcccacacaa ccacatctcc agcagcccat ggtgagcat ggactctggg    3780 agcctggcag gcccagtcaa caagtccttc aaggaagcgc tctgattcag ctgcatccat   3840
gccagggatg gcatgggcat ggcggccgat caagaggctg ggccttccag tctcaggatg   3900
caccttgacc aatggtctga gaggagttgc agtggtgtcc atgccataac ctatgtaggc   3960
tgacccggcc tgttggacat gtcccaactt gctctgagaa tacacaaggg agtgacgagc   4020
agacctttgg tgaacaagag cacgggttgc ctcatcaagg gcatcgtagg ctgccctcat   4080
gtcagcaaag caggttctgc ccccaactgc tgggacaact tctgcgctga acacagctcc   4140
ttgagccatg actggcatgt aggttgagtc ggcgtgccag gccatgttgc ccacaatgac   4200
cttcatcatg tcatcccact cagcaggaga gtgctggcgc actgtgccat ctgccttgac   4260
attggatatg caacaatgt cacctccgcc aatcctctca attgctccaa agcgtttagc     4320
aaaggtaatc tgttggtcat tgctgaggtg ttgcccaggg aagatcaaga gtgcatgttg   4380
aagccaggct gcatggaggg cagcgaaacc agcatcgtca agtgtggcaa ggtgaacacc   4440
agtgactgtg gcacccaagg tggcaccagt gggtgtgatt tggagagtgg tctgagccat   4500
ggagatctct gttaatcaga aaaactcaga ttaatcgaca aattcgatcg cacaaactag   4560
aaactaacac cagatctaga tagaaatcac aaatcgaaga gtaattattc gacaaaactc   4620
aaattatttg aacaaatcgg atgatattta tgaaaccta atcgagaatt aagatgatat     4680
ctaacgatca aacccagaaa atcgtcttcg atctaagatt aacagaatct aaaccaaaga   4740
acatatacga aattgggatc gaacgaaaac aaaatcgaag attttgagag aataaggaac   4800
acagaaattt accttgatca cggtagagag aattgagaga aagttttaa gattttgaga     4860 aattgaaatc tgaattgtga agaagaagct ttgggtattg ttttatagaa gaagaagaag    4920
aaaagacgag gacgactagg tcacgagaaa gctaaggcgg tgaagcaata gctaataata   4980
aaatgacacg tgtattgagc gttgtttaca cgcaaagttg ttttttggcta attgccttat   5040 ttttaggttg aggaaaagta tttgtgcttt gagttgataa acacgactcg tgtgtgccgg   5100
ctgcaaccac tttgacgccg tttattactg actcgtcgac aaccacaatt tctaacggtc   5160
gtcataagat ccagccgttg agatttaacg atcgttacga tttatatttt tttagcatta   5220
tcgttttatt ttttaaatat acggtggagc tgaaaattgg caataattga accgtgggtc   5280
ccactgcatt gaagcgtatt tcgtatttc tagaattctt cgtgctttat ttctttttcct    5340 ttttgttttt ttttgccatt tatctaatgc aagtgggctt ataaaatcag tgaatttctt   5400
ggaaaagtaa cttctttatc gtataacata ttgtgaaatt atccatttct tttaatttt     5460 tagtgttatt ggatatttt gtatgattat tgatttgcat aggataatga cttttgtatc    5520
aagttggtga acaagtctcg ttaaaaaagg caagtggttt ggtgactcga tttattcttg   5580
ttatttaatt catatatcaa tggatcttat ttggggcctg gtccatattt aacactcgtg   5640
ttcagtccaa tgaccaataa tattttttca ttaataacaa tgtaacaaga atgatacaca   5700
aaacattctt tgaataagtt cgctatgaag aagggaactt atccggtcct agatcatcag   5760
```

```
ttcatacaaa cctccataga gttcaacatc ttaaacaaga atatcctgat ccgttgacct    5820
gcaggtcgac aagcttttca gtcagtcacc gcggagcctg cttttttgta caaacttgtg    5880
cggccgcttg cccgggcatg gcgcgcccct gcaggatgca tgtcgaggag aaatatgagt    5940
cgaggcatgg atacactaag ttcccctgaa gtgagcatga tctttgatgc tgagatgatt    6000
cccagagcaa gatagtttgt gctgcaagtg acacaattgt aatgaaacca ccactcaacg    6060
aatttacttg tggctttgac atgtcgtgtg ctctgtttgt atttgtgagt gccggttggt    6120
aattattttt gttaatgtga ttttaaaacc tcttatgtaa atagttactt tatctattga    6180
agtgtgttct tgtggtctat agtttctcaa agggaaatta aaatgttgac atcccattta    6240
caattgataa cttggtatac acaaactttg taaatttggt gatatttatg gtcgaaagaa    6300
ggcaataccc attgtatgtt ccaatatcaa tatcaatacg ataacttgat aatactaaca    6360
tatgattgtc attgtttttc cagtatcaat atacattaag ctactacaaa attagtataa    6420
atcactatat tataaatctt tttcggttgt aacttgtaat tcgtgggttt ttaaaataaa    6480
agcatgtgaa aattttcaaa taatgtgatg gcgcaatttt atttttccgag ttccaaaata    6540 ttgccgcttc attaccctaa tttgtggcgc cacatgtaaa acaaaagacg attcttagtg    6600
gctatcactg ccatcacgcg gatcactaat atgaaccgtc gattaaaaca gatcgacggt    6660
ttatacatca ttttattgta cacacggatc gatatctcag ccgttagatt taatatgcga    6720
tctgattgct caaaaaatag actctccgtc tttgcctata aaaacaattt cacatctttc    6780
tcacccaaat ctactcttaa ccgttcttct tcttctacag acatcaattt ctctcgactc    6840
tagaggatcc aagcttatcg atttcgaacc cctcaggcga agaacaggta tgatttgttt    6900
gtaattagat caggggttta ggtctttcca ttactttta atgttttttc tgttactgtc    6960
tccgcgatct gattttacga caatagagtt tcgggttttg tcccattcca gtttgaaaat    7020
aaaggtccgt ctttaagtt tgctggatcg ataaacctgt gaagattgag tctagtcgat    7080
ttattggatg atccattctt catcgttttt ttcttgcttc gaagttctgt ataaccagat    7140
ttgtctgtgt gcgattgtca ttacctagcc gtgtatcgag aactagggtt ttcgagtcaa    7200 ttttgccccct tttggttata tctggttcga taacgattca tctggattag ggttttaagt    7260
ggtgacgttt agtattccaa tttcttcaaa atttagttat ggataatgaa aatccccaat    7320
tgactgttca atttcttgtt aaatgcgcag atccccatgg cttcgatctc ctcctcagtc    7380
gcgaccgtta gccggaccgc ccctgctcag gccaacatgg tggctccgtt caccggcctt    7440
aagtccaacg ccgccttccc caccaccaag aaggctaacg acttctccac ccttcccagc    7500
aacggtggaa gagttcaatg tatgcaggtg tggccggcct acggcaacaa gaagttcgag    7560
acgctgtcgt acctgccgcc gctgtctatg gcgccaccg tgatgatggc ctcgtcggcc    7620
accgccgtcg ctccgttcca ggggctcaag tccaccgcca gcctcccgt cgcccgccgc    7680 tcctccagaa gcctcggcaa cgtcagcaac ggcggaagga tccggtgcat ggccggcgcc    7740
gaggagatcg tgctgcagcc catcaaggag atctctggca cagtcaaact ccctggctca    7800
aagtcacttt caaaccgtat cctcttgctt gcagctcttt ctgaagggac cacagtggtt    7860
gacaaccttc tcaactcaga ggatgtccac tacatgctcg agccttgag gactcttggc    7920 ttgtctgttg aagcagacaa agctgccaag cgtgctgttg tggttggctg tggtggaaag    7980
ttcccagttg aagatgccaa agaggaagtc cagctcttcc ttgggaatgc tgggattgcc    8040
atgagatcct tgactgcagc tgtcactgca gctggtggga atgccaccta tgttcttgat    8100
ggcgtgccac gcatgaggga gagacccatt ggcgacttgg tggttggctt gaagcaactt    8160
```

```
ggagctgatg ttgactgctt ccttggcacc gactgtccac ctgttcgtgt caatgggatt    8220
ggaggtctcc ctggtggcaa ggtcaagctc tctggctcca tcagctccca gtacttgtca    8280
gccttgctca tggcagctcc cttggctctt ggtgatgtgg agattgagat cattgacaaa    8340
ctcatctcca ttccctatgt ggagatgacc ttgagattga tggaaaggtt tggtgtgaaa    8400
gctgagcatt ctgacagctg gacagattc tacatcaagg gaggtcagaa gtacaagtca     8460
cccaagaatg cctatgttga aggtgatgcc agctctgcca gctacttctt ggctggtgct    8520
gcaatcactg gagggactgt gacagtggaa ggttgtggca ctaccagctt gcaaggtgat    8580
gtgaagtttg ctgaggtgct tgagatgatg ggagcaaagg tcacctggac tgaaacctcc    8640
gtcacagtga ctggacctcc aagggagcca ttcggaagga acatctcaa agccattgat     8700 gtcaacatga caagatgcc agatgttgcc atgactcttg ctgtggttgc actctttgcc     8760
gatggaccaa cagccatcag agatgtggct tcctggagag tcaaggagac agagaggatg    8820
gttgcaatac gcacagagtt gaccaaactt ggagccagcg ttgaggaagg accagactac    8880
tgcatcatca cacctcccga gaagctcaac gtgacagcca tagacaccta tgatgaccac    8940
cgcatggcaa tggcttttctc ccttgcagcc tgtgcagaag tccctgtcac catacgtgac   9000
cctgggtgca ctcgcaagac cttcccagac tactttgatg tgctcagcac ctttgtcaag    9060
aactgagtag ttagcttaat cacctaacta gtggatcccc cgatccgcgt tgtgttttc     9120 tgggtttctc acttaagcgt ctgcgtttta cttttgtatt gggtttggcg tttagtagtt    9180
tgcggtagcg ttcttgttat gtgtaattac gcttttttctt cttgcttcag cagtttcggt   9240
tgaaatataa atcgaatcaa gtttcacttt atcagcgttg ttttaaattt tggcattaaa    9300
ttggtgaaaa ttgcttcaat tttgtatcta aatagaagag acaacatgaa attcgacttt    9360
tgacctcaaa tcttcgaaca tttatttcct gatttcacga tggatgagga taacgaaagg    9420
gcggttccta tgtccgggaa agttcccgta gaagacaatg agcaaagcta ctgaaacgcg    9480
gacacgacgt cgcattggta cggatatgag ttaaaccgac tcaattcctt tattaagaca    9540
taaaccgatt ttggttaaag tgtaacagtg agctgatata aaaccgaaac aaaccggtac    9600
aagtttgatt gagcaacttg atgacaaact tcagaatttt ggttattgaa tgaaaatcat    9660
agtctaatcg taaaaaatgt acagaagaaa agctagagca gaacaaagat tctatattct    9720
ggttccaatt tatcatcgct ttaacgtccc tcagatttga tcggggacat tcgtcggcgc    9780
gccttaatta agcggtggcc actatttttca gaagaagttc ccaatagtag tccaaaattt   9840
ttgtaacgaa gggagcataa tagttacatg caaaggaaaa ctgccattct ttagagggga    9900
tgcttgttta agaacaaaaa atatatcact ttcttttgtt ccaagtcatt gcgtatttt     9960 ttaaaaatat ttgttccttc gtatatttcg agcttcaatc actttatggt tcattgtatt    10020
ctggctttgc tgtaaatcgt agctaacctt cttcctagca gaaattatta atacttggga    10080
tattttttta gaatcaagta aattacatat taccaccaca tcgagctgct tttaaattca    10140
tattacagcc atataggctt gattcatttt gcaaaatttc caggatattg acaacgttaa    10200
cttaataata tcttgaaata ttaaagctat tatgattagg ggtgcaaatg gaccgagttg    10260
gttcggttta tatcaaaatc aaaccaaacc aactatatcg gtttggattg gttcggtttt    10320
gccgggtttt cagcattttc tggtttttt tttgttagat gaatattatt ttaatcttac     10380
tttgtcaaat ttttgataag taaatatatg tgttagtaaa aattaatttt ttttacaaac    10440
atatgatcta ttaaaatatt cttataggag aatttttctta ataacacatg atatttattt   10500
```

```
attttagtcg tttgactaat ttttcgttga tgtacacttt caaagttaac caaatttagt   10560
aattaagtat aaaaatcaat atgataccta aataatgata tgttctattt aattttaaat   10620
tatcgaaatt tcacttcaaa ttcgaaaaag atatataaga attttgatag gttttgacat   10680
atgaatatgg aagaacaaag agattgacgc attttagtaa cacttgataa gaaagtgatc   10740
gtacaaccaa ttatttaaag ttaataaaaa tggagcactt catatttaac gaaatattac   10800
atgccagaag agtcgcaaat atttctagat attttttaaa gaaaattcta taaaaagtct   10860
taaaggcata tatataaaaa ctatatattt atattttggt ttggttcgaa tttgttttac   10920
tcaataccaa actaaattag accaaatata attgagattt ttaatcgcgg cccatgatca   10980
caccggttag gatccggtga gtaatattgt acggctaaga gcgaatttgg cctgtagacc   11040
tcaattgcga gctttctaat ttcaaactat tcgggcctaa cttttggtgt gatgatgctg   11100
actcttaatt aacgtcgaca gcaaaacatg tgtgttttc tctgcaacaa gagggaggga   11160
aaatgaaaga ggaaacagaa gaggagtaat taataaaaga ttatatgata caagagaatt   11220
ttatgatcaa ataagaaagt aagtgtacca gagtcatcca tcaaaaatag catatccttt   11280
aaaacagaaa aggcaaggcc atggtttata gaccataagt ttccattatc aaagtaccgg   11340
aataaagatt ccattacacg acgtatggta gtcccctcct tggctaaatt ggccatatta   11400
tgtaggcaaa ctccagacca aaaagaggga ttcatgtcat cttccctgca tgaatttatg   11460
aacaataaag gtaatgaaat gaatagaaga tatcataaat ccatttcaaa gattttctgc   11520
tgataaaagt aattacattg ctacatttat ttcgccttta tcgttaacaa cttttctcca   11580
ggaagggttt ctccttttga catccagcaa aggagagatt tgaccctcat ggccatcac   11640 atcttgttcc tcatgatcca ggtttgctga attttctta ggaacttcat agttttccaa   11700
gacagcagaa acaatctata atgaaataga gagaaatttt cactatacat caaacaacat   11760
gtttaacact ccctccagtc ctttatataa aaatcaaatg ggtgagtttt attgtcctaa   11820
ttgtaagaca catggaccca catttaaatg tattaatttc taatttcctt ttattttctt   11880
aatttattat aaagtctatt aatgagacat tacttctcat gcaagtgaat gcattcattg   11940
acccattaac agtgtaagtc acactcattg gtggaaaaat ttatctcttg aattacaagt   12000
agtgtcatta aatataacta cccgttaaat catttaattc tatgggtatt tcagaaataa   12060
aatttaaatt tataacattt attaattaaa gctaactaaa ttattttcat cggtcttgat   12120
gaattagtca tctgtttctt ataaaccgaa ggaagtattt tttatttatt aacatcaata   12180
taaattatat atgaggatac aatgacaatg aaaaagccac actaaactta tctgaaagga   12240
gtgaaacagt acacataatt tgatatgaca tttttttacag aatgtagaca taatgcatat   12300
tgggataaga aacaagtgac aatacacaat acactgtcac ttgtttttt ataaatagga   12360 ccggaggtag taagtatttg gagaaaaata agaagacaac caaaatagta tgtttacaag   12420
ttgatgcaac cacctagaaa aactatgtaa gtattcatac aattgaagaa gtaaaaaaat   12480
cacttacatt atcaaattcg actgatatgt gagattgttc acccataaac cgaacctaca   12540
gagcaaaata gttcatttaa ctcaaaagga tgagtatata gattatatta aaggtgaaga   12600
aaggagatag atttactgag aaagcaggaa atacaacaga aatgataatc catttcattc   12660
cagcatcttt gtaaatttaa catatcattg tatccaaccc caaagcaagc gaatggaaaa   12720
agaaatagaa tttaacatat cattgtaaat ttaagaaacc aaagcctttt gataaaataa   12780
aaagtaagag tgagagtgag agtgagagag agagagaatt catgtaaaag caagaactta   12840
gagagataaa tgaaaaatgt aaaaacaaga acaactaagg tgccaataat tgcctactac   12900
```
acaggtccta aaacatgcta attggccata acattattaa aaaaagaaga aaaaagaaac    12960
tctttatttt taccttaggc attaacttag aactagggca agctcaagaa attattggac    13020
cattgaagat aaaatagaaa gataatctaa aatcatttga attttgacag ccataaagca    13080
gagatgcact tgcccactgt tggacaaaaa tgctagagga aaaaatagta aatgaacaaa    13140
gatagaaaga gaagtgttgg cacctctaaa ggcgtcagag aatttaactt tagacagtac    13200
taaagcaaaa agacattgat tcttattgta gctgttttg gcactatgta gacagaaaaa    13260
tggctgagac ctaggaagat cttggcaatt aatgatcaga ccagggagaa ataagctatt    13320
gccccaaaag aatctagaat tgctcagaca aataaaatgc tatgggaaat agatgtatat    13380
ccaattccag agttagtttt tttttatcca tgggaatcaa agacaaggtc aagaggttta    13440
caacaactca cacacccctta ctcaaccaat tgagctagac ccccttgaca ttctagagtt    13500
agtttagacc agaagattat gccagttgac tctcaagggt caagacatca ctggaaggaa    13560
catcatctat tctttccaac taagaccatt ctgtagcaag atacttaata tatctgttgg    13620
cagtaggaat tgcaaccggg acaagatatt aaaagaaaaa aatacatata ttgaaaaaaa    13680
agtaagatgt tatgaatgtt ggggatactt aagtcttaac gagtacctaa aagtgtattc    13740
tttgcttaac caaagctaac tatggatgca tgattaaact atttcttcta ggtttagtac    13800
aaccaatctt tccctcaat attaaacatg tttagcgctg cttctagcct attagtgctg    13860
atttctaatg ttgataacaa ttaccatgtc ttaaatatag ttttcttttt aaatcactct    13920
ccttcaaagt acaaactgac aagcaacatg ctgttgtgca agaccaattt gtgatctaaa    13980
agttgaaaca atggtggaat tataaaataa ataccattgc tgaaagagct ttcaaaccag    14040
ctgaacgact atttcttgca ctttcatctt ctcctgtttc ttgagctaat tgacagagct    14100
ttgggataat accttctaag ttgaacaggt aacttccatc aatctgcaaa atataaaaaa    14160
tatgtaggct catgtttttc cagtcaaagc t                                   14191

<210> SEQ ID NO 28
<211> LENGTH: 14619
<212> TYPE: DNA
<213> ORGANISM: Artificial
<220> FEATURE:
<223> OTHER INFORMATION: Hypothetical sequence of Event 9582.812.9.1
      containing 5' genomic flank, 9582 T-strand insert, 3' genomic
      flank

<400> SEQUENCE: 28
ttaattataa tgactttatt ataaaatgaa caatttcaaa atcttcacac tccaattta     60 gattccttt atatcatttt ctattgagta aaccaccatt tccattctta aaaatgtgag    120
gcctcgcata aaagcatgaa aatggcaaaa acatccccaa aattacattt tatcagtcca    180
gttaatcaat cgtaaggatc ttagtgtctc tattaacata tgatgaggtg acgtgttaag    240
tgttatgcca tgtacttgtt gatctgtcat gttgcgatca cgtcagcata aatcaaaata    300
aaacttttaa agtacaaaat gataataata ttttatttat ttatttcctc tcgcatccca    360
agatgacagt gaagaaaata attttttgag accgataatt ctaacataca ctattgactt    420
cagattataa agtactgttc aaatatgaaa tttaaatgct attctagacc aaaatctgaa    480
aattaccaaa atttccctca tgcatcaaac tatattgaat ctcatttaa gacaaaatac    540 aattggaaaa attataaaag ctttattttta aacttagaaa attactataa tatttgaatt    600 ttttctaca actatctaga ttttgtttta aaattatcaa aataccctga gccttttgat    660

```
caagagtatt attgtcttta gttattgtcg aaaatattat caattgacag tataagttta    720
gtcactattt tgattaaata ttatactttt tttaaggatt aattattata cttttataac    780
ttaatccttt ttattataaa atgaacaatt ttaaaatctt ctcactccaa ttttatactc    840
actttatatt cttaataata tgttgtatga gcagaactaa actgaaattc cttaaaaaga    900
aagtcttgat attggtatga gtcttgtgaa taaaagaatt gattgaggga ttccactaaa    960
tcttgccact gactttttat cattgtctat ttttgtttca gaaatcaaat cagtatatat    1020
acttttttat ctgtccattg ttcaatttcg agcgtctcga tatattatgc gcctaaattg    1080
gacatccgag ttaaaagtta tgaccattcg aatttcccga cacccagtca gcatcatcac    1140
accaaaagtt aggcccgaat agtttgaaat tagaaagctc gcaattgagg tctacaggcc    1200
aaattcgctc ttagccgtac aatattactc accggatcct aaccggtgtg atcatgggcc    1260
gcgattaaaa atctcaatta tatttggtct aatttagttt ggtattgagt aaaacaaatt    1320
cggcgccatg cccgggcaag cggccgcaca agtttgtaca aaaaagcagg ctccgcggtg    1380
actgactgaa aagcttgtcg acctgcaggt caacggatca ggatattctt gtttaagatg    1440
ttgaactcta tggaggtttg tatgaactga tgatctagga ccggataagt tcccttcttc    1500
atagcgaact tattcaaaga atgttttgtg tatcattctt gttacattgt tattaatgaa    1560
aaaatattat tggtcattgg actgaacacg agtgttaaat atggaccagg ccccaaataa    1620
gatccattga tatatgaatt aaataacaag aataaatcga gtcaccaaac cacttgcctt    1680
ttttaacgag acttgttcac caacttgata caaaagtcat tatcctatgc aaatcaataa    1740
tcatacaaaa atatccaata acactaaaaa attaaaagaa atggataatt tcacaatatg    1800
ttatacgata aagaagttac ttttccaaga aattcactga ttttataagc ccacttgcat    1860
tagataaatg gcaaaaaaaa acaaaaagga aagaaataa agcacgaaga attctagaaa    1920
atacgaaata cgcttcaatg cagtgggacc cacggttcaa ttattgccaa ttttcagctc    1980
caccgtatat ttaaaaaata aaacgataat gctaaaaaaa tataaatcgt aacgatcgtt    2040
aaatctcaac ggctggatct tatgacgacc gttagaaatt gtggttgtcg acgagtcagt    2100
aataaacggc gtcaaagtgg ttgcagccgg cacacacgag tcgtgtttat caactcaaag    2160
cacaaatact tttcctcaac ctaaaaataa ggcaattagc caaaaacaac tttgcgtgta    2220
aacaacgctc aatacacgtg tcatttttatt attagctatt gcttcaccgc cttagctttc    2280
tcgtgaccta gtcgtcctcg tcttttcttc ttcttcttct ataaacaat acccaaagct    2340 tcttcttcac aattcagatt tcaatttctc aaaatcttaa aaactttctc tcaattctct    2400
ctaccgtgat caaggtaaat ttctgtgttc cttattctct caaaatcttc gattttgttt    2460
tcgttcgatc ccaatttcgt atatgttctt tggtttagat tctgttaatc ttagatcgaa    2520
gacgattttc tgggtttgat cgttagatat catcttaatt ctcgattagg gtttcataaa    2580
tatcatccga tttgttcaaa taatttgagt tttgtcgaat aattactctt cgatttgtga    2640
tttctatcta gatctggtgt tagtttctag tttgtgcgat cgaatttgtc gattaatctg    2700
agtttttctg attaacagag atctccatgg agaacaatat ccagaaccag tgtgtcccat    2760
acaattgcct caacaatcct gaagttgaga tcctcaacga agagaggagc actgacgcc    2820 ttcccttga catctccctc tccctcacaa ggttcctttt gtctgagttt gttcctggtg    2880
tgggtgtggc ctttggcctc tttgacctca tctgggcctt catcaccca tctgattgga    2940 gcctcttcct tctccagatt gaacaattga ttgagcagag gattgagacc cttgaaagga    3000
acagagccat caccacactt cgtggccttg ctgacagcta tgaaatctac attgaagcac    3060
```

```
tccgtgagtg ggaagccaat cccaacaatg ctcaactccg tgaagatgtg aggattcgct     3120
ttgccaacac agatgacgct ttgatcacag ccatcaacaa tttcaccctc accagctttg     3180
agatcccttt gctctcagtc tatgttcaag ctgcaaacct ccacttgagc ttgcttaggg     3240
atgctgtgtc cttcggacaa ggttggggac ttgacatagc cactgtcaac aatcactaca     3300
acagactcat caacttgatt catcgctaca ccaaacattg cttggacacc tacaatcaag     3360
gattggagaa cctcagaggc accaacactc gccaatgggc aaggttcaac cagtttagaa     3420
gggatctcac actcactgtg cttgacatag ttgctctctt ccccaactat gatgttcgca     3480
cctacccaat tcaaaccagc tcccaactta caagggaaat ctacacctcc tcagtcattg     3540
aggacagccc agtttctgcc aacatcccca atggtttcaa ccgtgctgag tttggtgtca     3600 gaccaccccca tctcatggac ttcatgaact ccttgtttgt gactgccgag actgttaggt     3660
cccaaactgt gtggggaggc caccttgtta gctcccgcaa caccgctggc aaccgcatca     3720
acttcccatc ctatgggggtt ttcaatcctg gtggagccat ctggattgca gatgaggacc     3780
caaggccttt ctacagaacc ttgtcagatc ctgtctttgt cagaggaggc tttggcaatc     3840
cacactatgt tcttggtttg aggggagtgg cttttcagca gactggcacc aatcacaccc     3900
gcacattcag aaacagcggc accattgaca gccttgatga gatcccacct caagacaaca     3960
gcggagcacc ctggaacgac tactcccatg tgctcaatca tgtcaccttt gtgcgctggc     4020
ctggtgagat cagcggttca gattcttgga gagcaccaat gttctcatgg acccatcgct     4080
ctgccacacc cacaaacacc attgatccag agagaatcac ccagattccc ttggtgaagg     4140
cacacacact tcagtctgga accacagttg tcagagggcc tgggttcact ggtggagaca     4200
ttctcagacg cacctctgga gggccatttg cttacaccat tgtcaacatc aatgggcaac     4260
ttccccagcg ttaccgtgcc agaatccgct atgcttccac cactaacttg agaatctatg     4320
tcacagttgc tggtgaaagg atctttgctg tcagttcaa caagacaatg gacactggtg     4380
atccattgac attccagtca ttctcctatg ccaccatcaa cactgcattc accttttccaa     4440 tgagccagtc cagcttcaca gtgggtgcag ataccttcag ctccggcaat gaggtgtaca     4500
ttgaccgctt tgagttgatt ccagtgactg ccacacttga ggctgagtct gacttggagc     4560
gtgctcagaa ggccgtgaat gctctcttca cctcttcaaa tcagattggg ctcaagacag     4620
atgtgactga ctaccatata gaccgtgttt ccaatcttgt tgagtgcctc tctgatgagt     4680
tctgcttgga tgagaagaaa gagttgtcag agaaggtcaa gcacgccaag aggctctctg     4740
atgagaggaa cttgcttcaa gatcccaact tcagagggat caaccgtcaa ttggatcgtg     4800
gatggagggg atcaactgac ataaccattc aaggaggtga cgatgtgttc aaggagaact     4860
atgtcacact cttgggggacc tttgatgagt gctacccaac ataccttttac cagaagatag     4920 acgaaagcaa gctcaaggcc tacacaagat accagttgag aggttacatt gaggactctc     4980
aagaccttga aatctacctc atcagataca acgccaaaca tgagacagtc aatgtgcctg     5040
ggactggttc actctggcca ctttcagccc caagccccat tggcaagtgt gcccatcact     5100
cacatcactt ctccttggac atagatgttg gctgcactga cttgaatgag gaccttggtg     5160
tgtgggtgat cttcaagatc aagacccaag atggccatgc aaggttgggc aatcttgagt     5220 ttccttgaaga gaaaccactt gttggagaag cccttgccag agtgaagagg gctgagaaga     5280
aatggaggga caagagagag aagttggagt gggaaacaaa cattgtgtac aaagaagcca     5340
aagaatcagt tgatgctttg tttgtgaact cccaatatga taggctccaa gctgacacca     5400
```

```
acatagcaat gattcatgct gcagacaaaa gggttcacag cattcgtgaa gcataccttc   5460
ctgaactctc agtgattcct ggggtcaatg ctgcaatctt tgaagagctt gaaggacgca   5520
tcttcactgc cttctccttg tatgatgcaa ggaatgtcat caagaatggt gacttcaaca   5580
atggcctttc tgctggaat gtgaaagggc acgtggatgt tgaagagcag aacaatcacc    5640
gctctgtcct tgttgtccct gagtgggaag ctgaagtttc acaagaagtt cgtgtctgcc   5700
ctggtcgtgg ctacattctt cgtgtgactg cttacaaaga aggctatgga gaaggttgtg   5760
tcaccatcca cgagatagag aacaatactg atgaattgaa gttcagcaac tgtgttgagg   5820
aagaggtcta cccaaacaat actgtcactg caatgactac cactgcaact caagaagagt   5880
atgagggcac ttacacttct cgcaaccgtg gctatgatgg agcctatgag agcaactcat   5940
ctgtgcctgc tgactatgct tcagcctatg aagagaaggc atacactgat ggaaggcgtg   6000
acaatccttg tgaaagcaac agaggctatg ggactacac accctccca gctggctatg    6060 tgaccaaaga gttggagtac tttcctgaaa ctgacaaggt ttggattgag ataggagaaa   6120
ctgaaggcac attcatagtt gactctgtgg agcttttgct catggaagag tgagtagtta   6180
gcttaatcac ctagagctcg gtcaccagca taattttat taatgtacta aattactgtt    6240
ttgttaaatg caattttgct ttctcgggat tttaatatca aaatctattt agaaatacac   6300 aatatttgt tgcaggcttg ctggagaatc gatctgctat cataaaaatt acaaaaaaat    6360
tttatttgcc tcaattattt taggattggt attaaggacg cttaaattat tgtcgggtc    6420 actacgcatc attgtgattg agaagatcag cgatacgaaa tattcgtagt actatcgata   6480
atttatttga aaattcataa gaaaagcaaa cgttacatga attgatgaaa caatacaaag   6540
acagataaag ccacgcacat ttaggatatt ggccgagatt actgaatatt gagtaagatc   6600
acggaatttc tgacaggagc atgtcttcaa ttcagcccaa atggcagttg aaatactcaa   6660
accgccccat atgcaggagc ggatcattca ttgtttgttt ggttgccttt gccaacatgg   6720
gagtccaagg ttgcggccgc gcgccgaaaa caactttgta tacaaaagtt gccgcggtga   6780
ctgactgaac taaacccaga aggtaattat ccaagatgta gcatcaagaa tccaatgttt   6840
acgggaaaaa ctatggaagt attatgtaag ctcagcaaga agcagatcaa tatgcggcac   6900
atatgcaacc tatgttcaaa atgaagaat gtacagatac aagatcctat actgccagaa    6960
tacgaagaag aatacgtaga aattgaaaaa gaagaaccag gcgaagaaaa gaatcttgaa   7020
gacgtaagca ctgacgacaa caatgaaaag aagaagataa ggtcggtgat tgtgaaagag   7080
acatagagga cacatgtaag gtggaaaatg taagggcgga aagtaaccct atcacaaagg   7140
aatcttatcc cccactactt atccttttat attttccgt gtcattttg cccttgagtt      7200 ttcctatata aggaaccaag ttcggcattt gtgaaaacaa gaaaaaattt ggtgtaagct    7260
attttctttg aagtactgag gatacaactt cagagaaatt tgtaagtttg tagatccaac   7320
aatggacaac aatcccaaca tcaacgagtg cattccttac aactgcctga gcaaccctga   7380
ggttgaggtg ctgggtggag aacggattga gactggttac acacctatcg acatctcgtt   7440
gtcacttacc caattccttt tgtcagagtt cgtgcccggt gctggattcg tgcttggact   7500
tgtcgatatc atttggggaa tctttggtcc ctctcaatgg gacgcctttc ttgtacagat   7560
agagcagtta attaaccaaa gaatagaaga attcgctagg aaccaagcca tctcaaggtt   7620
agaaggcctc agcaaccttt accagattta cgcagaatct tttcgagagt gggaagcaga   7680
cccgaccaat cctgccttaa gagaggagat gcgcattcaa ttcaatgaca tgaacagcgc   7740
gctgacgacc gcaattccgc tcttcgccgt tcagaattac caagttcctc ttttatccgt   7800
```

```
gtacgtgcag gctgccaacc tgcacttgtc ggtgctccgc gatgtctccg tgttcggaca    7860
acggtggggc tttgatgccg caactatcaa tagtcgttat aatgatctga ctaggcttat    7920
tggcaactat accgattatg ctgttcgctg gtacaacacg ggtctcgaac gtgtctgggg    7980
accggattct agagattggg tcaggtacaa ccagttcagg cgagagttga cactaactgt    8040
cctagacatt gtcgctctct ttcccaacta cgactctagg cgctacccaa tccgtactgt    8100
gtcacaattg acccgggaaa tctacacaaa cccagtcctc gagaacttcg acggtagctt    8160
tcgaggctcg gctcagggca tagagagaag catcaggtct ccacacctga tggacatatt    8220
gaacagtatc acgatctaca ccgatgcgca ccgcggttat tactactggt cagggcatca    8280
gatcatggca tcacccgttg ggttctctgg accagaattc actttcccac tttacgggac    8340
tatgggcaat gcagctccac aacaacgtat tgttgctcaa ctcggtcagg gcgtgtatag    8400
aaccttgtcc agcactctat ataggagacc tttcaacatc ggcatcaaca atcaacaatt    8460
gtctgtgctt gacgggacag aatttgccta tggaacctcc tcaaatctgc catccgctgt    8520
ctacagaaag agcggaacag ttgatagctt ggatgagatc cctccacaga caacaacgt     8580 tccacctagg caagggttta gccatcgcct tagccatgtg tccatgttcc gttcaggctt    8640
tagtaatagc agcgttagta tcatcagagc tccgatgttc tcttggatac atcgtagtgc    8700
tgagtttaac aacataattg catccgatag cattactcag atcccagctg tcaaggggaa    8760
cttttctctt aatggttctg tcatttcagg accaggattc actggaggcg acttggttag    8820
gctgaattct tccggcaaca acatccagaa tagagggtat attgaagtgc ccattcactt    8880
cccatcgaca tctaccagat atcgtgttcg tgtaaggtat gcctctgtta ccctattca    8940 cctcaacgtc aattgggta attcctccat cttttccaat acagtaccag cgacagctac    9000
atccttggat aatctccaat ctagcgattt cggttacttc gaaagtgcca atgccttcac    9060
ctcttcccta ggtaacatag taggtgttag aaatttctcc ggaaccgccg gagtgataat    9120
cgaccgcttc gaattcattc ccgttactgc aacgctcgag gcagagtctg acttggaaag    9180
agcacagaag gcggtgaatg ctctgttcac ttcgtccaat cagattgggc tcaagacaga    9240
tgtgactgac tatcacatcg atcgcgtttc caaccttgtt gagtgcctct ctgatgagtt    9300
ctgtttggat gagaagaagg agttgtccga gaaggtcaaa catgctaagc gacttagtga    9360
tgagcggaac ttgcttcaag atcccaactt tcgcgggatc aacaggcaac tagatcgtgg    9420
atggagggga agtacggaca tcaccattca aggaggtgat gatgtgttca aggagaacta    9480
tgttacgctc ttgggtacct ttgatgagtg ctatccaaca tacctgtacc agaagataga    9540
tgaatcgaaa ctcaaagcct acacaagata ccagttgaga ggttacatcg aggacagtca    9600
agaccttgag atctacctca tcagatacaa cgccaaacat gagacagtca atgtgcctgg    9660
gacgggttca ctctggccac tttcagcccc aagtcccatc ggcaagtgtg cccatcactc    9720
acaccacttc tccttggaca tagacgttgg ctgtaccgac ctgaacgaag acctcggtgt    9780
gtgggtgatc ttcaagatca agactcaaga tggccatgcc aggctaggca atctggagtt    9840
tctagaagag aaaccacttg ttggagaagc cctcgctaga gtgaagaggg ctgagaagaa    9900
gtggagggac aagagagaga agttggaatg ggaaacaaac attgtgtaca agaagccaa     9960 agaaagcgtt gacgctctgt ttgtgaactc tcagtatgat aggctccaag ctgataccaa   10020
catagctatg attcatgctg cagacaaacg cgttcatagc attcgggaag cttaccttcc   10080
tgaacttagc gtgattccgg gtgtcaatgc tgctatcttt gaagagttag aagggcgcat   10140
```

```
cttcactgca ttctccttgt atgatgcgag gaatgtcatc aagaatggtg acttcaacaa   10200
tggcctatcc tgctggaatg tgaaagggca cgtagatgta gaagaacaga acaatcaccg   10260
ctctgtcctt gttgttcctg agtgggaagc agaagtttca caagaagttc gtgtctgtcc   10320
tggtcgtggc tacattcttc gtgttaccgc gtacaaagaa ggatacgag  aaggttgcgt   10380 caccatacac gagattgaga acaacaccga cgagctgaag ttcagcaact gcgtcgagga   10440
ggaagtctac ccaaacaaca ccgtaacttg caatgactac actgcgactc aagaggagta   10500
tgagggtact tacacttctc gcaatcgagg atacgatgga gcctatgaga gcaactcttc   10560
tgtacccgct gactatgcat cagcctatga ggagaaggct acaccgatg  gacgtaggga   10620 caatccttgc gaatctaaca gaggctatgg ggactacaca ccgttaccag ccggctatgt   10680
caccaaagag ttagagtact tccagaaaac cgacaaggtt tggattgaga ttggagaaac   10740
ggaaggaaca ttcattgttg atagcgtgga gttacttctg atggaggaat gagtagttag   10800
cttaatcacc tagagctcgg ttacctatca aaatctattt agaaatacac aatattttgt   10860
tgcaggcttg ctggagaatc gatctgctat cataaaaatt acaaaaaaat tttatttgcc   10920
tcaattattt taggattggt attaaggacg cttaaattat ttgtcgggtc actacgcatc   10980
attgtgattg agaagatcag cgatacgaaa tattcgtagt actatcgata atttatttga   11040
aaattcataa gaaaagcaaa cgttacatga attgatgaaa caatacaaag acagataaag   11100
ccacgcacat ttaggatatt ggccgagatt actgaatatt gagtaagatc acggaatttc   11160
tgacaggagc atgtcttcaa ttcagcccaa atggcagttg aaatactcaa accgccccat   11220
atgcaggagc ggatcattca ttgtttgttt ggttgccttt gccaacatgg gagtccaagg   11280
ttgcggccgc gcgccgaccc agctttcttg tacaaagtgg ttgcggccgc ttaattaaat   11340
ttaaatgccc gggcgtttaa acgcggccgc ttaattaagg ccggcctgca gcaaacccag   11400
aaggtaatta tccaagatgt agcatcaaga atccaatgtt tacgggaaaa actatggaag   11460
tattatgtaa gctcagcaag aagcagatca atatgcggca catatgcaac ctatgttcaa   11520
aaatgaagaa tgtacagata caagatccta tactgccaga atacgaagaa gaatacgtag   11580
aaattgaaaa agaagaacca ggcgaagaaa agaatcttga agacgtaagc actgacgaca   11640
acaatgaaaa gaagaagata aggtcggtga ttgtgaaaga gacatagagg acacatgtaa   11700
ggtggaaaat gtaagggcgg aaagtaacct tatcacaaag gaatcttatc ccccactact   11760 tatccttttta tatttttccg tgtcattttt gcccttgagt tttcctatat aaggaaccaa   11820
gttcggcatt tgtgaaaaca agaaaaaatt tggtgtaagc tattttcttt gaagtactga   11880
ggatacaact tcagagaaat ttgtaagttt gtagatctcc atgtctccgg agaggagacc   11940
agttgagatt aggccagcta cagcagctga tatggccgcg gtttgtgata tcgttaacca   12000
ttacattgag acgtctacag tgaactttag gacagagcca caaacaccac aagagtggat   12060
tgatgatcta gagaggttgc aagatagata cccttggttg gttgctgagg ttgagggtgt   12120
tgtggctggt attgcttacg ctgggccctg gaaggctagg aacgcttacg attggacagt   12180
tgagagtact gtttacgtgt cacataggca tcaaaggttg ggcctaggat ccacattgta   12240
cacacatttg cttaagtcta tggaggcgca aggttttaag tctgtggttg ctgttatagg   12300
ccttccaaac gatccatctg ttaggttgca tgaggctttg ggatacacag cccggggtac   12360
attgcgcgca gctggataca agcatggtgg atggcatgat gttggttttt ggcaaaggga   12420
ttttgagttg ccagctcctc caaggccagt taggccagtt acccagatct gaggtaccct   12480
gagcttgagc ttatgagctt atgagcttag agctcggatc cactagtaac ggccgccagt   12540
```

```
gtgctggaat tcgcccttga ctagataggc gcccagatcg gcggcaatag cttcttagcg    12600
ccatcccggg ttgatcctat ctgtgttgaa atagttgcgg tgggcaaggc tctctttcag    12660
aaagacaggc ggccaaagga acccaaggtg aggtgggcta tggctctcag ttccttgtgg    12720
aagcgcttgg tctaaggtgc agaggtgtta gcgggatgaa gcaaaagtgt ccgattgtaa    12780
caagatatgt tgatcctacg taaggatatt aaagtatgta ttcatcacta atataatcag    12840
tgtattccaa tatgtactac gatttccaat gtctttattg tcgccgtatg taatcggcgt    12900
cacaaaataa tccccggtga ctttctttta atccaggatg aaataatatg ttattataat    12960
ttttgcgatt tggtccgtta taggaattga agtgtgcttg cggtcgccac cactcccatt    13020
tcataatttt acatgtattt gaaaataaa  aatttatggt attcaattta aacacgtata    13080
cttgtaaaga atgatatctt gaagaaata  tagtttaaat atttattgat aaaataacaa    13140
gtcaggtatt atagtccaag caaaaacata aatttattga tgcaagttta aattcagaaa    13200
tatttcaata actgattata tcagctggta cattgccgta gatgaaagac tgagtgcgat    13260
attatggtgt aatacatagc ggccgggttt ctagtcaccg gttaggatcc gtttaaactc    13320
gaggctagcg catgcacata gacacacaca tcatctcatt gatgcttggt ataattgtc    13380 attagattgt ttttatgcat agatgcactc gaaatcagcc aattttagac aagtatcaaa    13440
cggatgtgac ttcagtacat taaaaacgtc cgcaatgtgc cattggcaac aacctctgat    13500
gccgtaactt ttctttgttg gttcagaaat ccaaccgtta tggataattc taaatcctca    13560
tacttcatct ttccacaaaa gcacaaattc tcctactagt aggctttaga tgtgttttat    13620
atctctaaaa gcattaaata ttttttattt ttcattcatt atttcataaa agatagtaaa    13680
gtcccctttg tctgcagaga aaatggtgaa aaaagaaaat aaataaataa ataataaagt    13740
gatgtaacat tcatatttttt atattatatt ttaattcaaa aactttaatc tcatgtgact    13800 tttattttc ttttcactac cgaacggagc ctgagagaat atagcattac tcaaccgtta    13860
tattgctgaa aaatttctag taatgaccat ttgaatttct cgagagcttc cgttgttcaa    13920
tttctagcgt ctctatatgt gatgcggcag aatcggacct ccgagtgaaa agttatgacc    13980
atttgaattt ttcgaaagct tccgttgttt aatttcgagc gtctcgatat attatgcggc    14040
tgaatcggac ctccgagtga aaagttatga tcatttgaat tgctcaagag cttccattgt    14100
tcaatttcga acgtctcgat atattatgcg catgaatcag acatccgagt gaaaagttat    14160
gaccatttga attgctcaag agtttccatt gccccatttt gaacgtctcg atatattatg    14220
cgcctgaatc ggacttccga gttaaatgtt attctcaaga gcttttgttg ttcaatttca    14280
agcgtctcga tatattatgc acctgaatcg gatctccgag tgaaatgtta gttccatttg    14340
aattggtcaa gtgcttccat agcatggtgg gcgagagtac caccctccac caaacaaacc    14400
cactctctat attcctattt ctgtatactt ctctagacaa cgttagtagt aacacaacca    14460
ctctcattag ccttaaccga cccagagaaa acacgcatcg gttaatgcta ttcctttctc    14520
tgaaatcgct tcgaagacaa gaaaagaatt aataaccaaa agaaaccgca cctcatacca    14580
gaaatagctt acatgcctaa cgattttctt tgcttttaa                          14619
```

<210> SEQ ID NO 29
<211> LENGTH: 15294
<212> TYPE: DNA
<213> ORGANISM: Artificial Sequence
<220> FEATURE:
<223> OTHER INFORMATION: Expected sequence of soybean event
     9582.814.19.1

<400> SEQUENCE: 29

```
ttaacaatga ccaagattta tgctatatag aagacttgga gggcttaagg ctatgatata      60
ttatggatga tatggttctg atttgtgtag tttcgaagga tcaaatcaac catttgttgg     120
tacaatggga agaaaaaatg tttcatcat tccactctat tgaaaaagat ccaacaattg     180
taacaccccg acgaatcaca ccggaaagag aagaatccaa agattgtgta ggtatgagac     240
tgtatagttg atgaaaactt aaaaaaatta attggtacta cttataccaa caagatgcat     300
atatttttcg atagcctatc acataagaac ttcatagtta agggtgctta acttggagta     360
gttatgaaat gagtgacctt taaaataat tattgtctta ggttattgta tgaaaataaa     420
aaataataat aaatatacat aaaaaataat aattttataa aattaacctt atattatcat     480
taatttattt ttagattttg ttattcatta ttaatatatg aggtataaat gaaaaatata     540
attaatgtca cattaaaaaa ttaaaatgat aattattttg aaacaaatta tttatttta     600
tacgacaatt ataatagaaa tttgagagta aaaaaaaatt gaaaattcat aaaatatatg     660
aatatattca tttctcctat ccgtcaaata aatctgctcc ataatttatc taagcattgg     720
tcttgtagtt cagagtaata aaattttagc aattattagt tagtacagat acatttaaag     780
aaataatata ttttagcaac tagaagttta taaaaagttt taaattataa agacttatat     840
ataaatttag taaaactaga tggatgtccc aagtaaattt tatataacta ttctcgtaca     900
acattaatga aaatcttgtt tctattattt atatgtatat tattatttta ttttggaaca     960
atatgggatt aaaaactctt ataaattaaa tcttagaata agttttccta acatgttttt    1020
tttatggatg tttcctaac atgtttggtt atcttagttt tgctttaatt ttgtcggatt    1080
atttttggac tttattaggt aattttgata aaacttttag ttgatgttag tagtttactc    1140
ttacataatg atttgatatt gaatgtgtat aattggaagg caataaatga agatcaagcg    1200
tacaagagtt cgccaatcaa gaggatttga agagagtaaa atattatgcg aagtcccatg    1260
tgaagaaaat ccaaccattg gaataaaaaa taaagttttt tctttggaat tgctaatgct    1320
acagcactta ttggtacttg tcctaaaaat gaaactctag ctatatttag cacttgatat    1380
tcatgaatca aacttctcta tgaaataacc gcggtgcgca tcggtgcctg ttgatcccgc    1440
gcaagttggg atcttgaagc aagttccgct catcactaag tcgcttagca tgtttgacct    1500
tctcggacaa ctccttcttc tctttaattg atcaacagtc agcatcatca caccaaaagt    1560
taggcccgaa tagtttgaaa ttagaaagct cgcaattgag gtctacaggc caaattcgct    1620
cttagccgta caatattact caccggatcc taaccggtgt gatcatgggc cgcgattaaa    1680
aatctcaatt atatttggtc taatttagtt tggtattgag taaaacaaat tcggcgccat    1740
gcccgggcaa gcggccgcac aagtttgtac aaaaaagcag gctccgcggt gactgactga    1800
aaagcttgtc gacctgcagg tcaacggatc aggatattct tgtttaagat gttgaactct    1860
atggaggttt gtatgaactg atgatctagg accggataag ttcccttctt catagcgaac    1920
ttattcaaag aatgttttgt gtatcattct tgttacattg ttattaatga aaaaatatta    1980
ttggtcattg gactgaacac gagtgttaaa tatggaccag gccccaaata agatccattg    2040
atatatgaat taaataacaa gaataaatcg agtcaccaaa ccacttgcct ttttaacga    2100
gacttgttca ccaacttgat acaaagtca ttatcctatg caaatcaata atcatacaaa    2160
aatatccaat aacactaaaa aattaaaaga aatggataat ttcacaatat gttatacgat    2220
aaagaagtta cttttccaag aaattcactg attttataag cccacttgca ttagataaat    2280
```

```
ggcaaaaaaa aacaaaaagg aaaagaaata aagcacgaag aattctagaa aatacgaaat    2340
acgcttcaat gcagtgggac ccacggttca attattgcca attttcagct ccaccgtata    2400
tttaaaaaat aaaacgataa tgctaaaaaa atataaatcg taacgatcgt taaatctcaa    2460
cggctggatc ttatgacgac cgttagaaat tgtggttgtc gacgagtcag taataaacgg    2520
cgtcaaagtg gttgcagccg gcacacacga gtcgtgttta tcaactcaaa gcacaaatac    2580
ttttcctcaa cctaaaaata aggcaattag ccaaaaacaa ctttgcgtgt aaacaacgct    2640
caatacacgt gtcattttat tattagctat tgcttccacg ccttagcttt ctcgtgacct    2700
agtcgtcctc gtcttttctt cttcttcttc tataaaacaa tacccaaagc ttcttcttca    2760
caattcagat ttcaatttct caaaatctta aaaactttct ctcaattctc tctaccgtga    2820
tcaaggtaaa tttctgtgtt ccttattctc tcaaaatctt cgattttgtt ttcgttcgat    2880
cccaatttcg tatatgttct ttggtttaga ttctgttaat cttagatcga agacgatttt    2940
ctgggtttga tcgttagata tcatcttaat tctcgattag ggtttcataa atatcatccg    3000
atttgttcaa ataatttgag ttttgtcgaa taattactct tcgatttgtg atttctatct    3060
agatctggtg ttagtttcta gtttgtgcga tcgaatttgt cgattaatct gagttttctt    3120
gattaacaga gatctccatg gagaacaata tccagaacca gtgtgtccca tacaattgcc    3180
tcaacaatcc tgaagttgag atcctcaacg aagagaggag cactggacgc cttcccttg     3240 acatctccct ctccctcaca aggttccttt tgtctgagtt tgttcctggt gtgggtgtgg    3300
cctttggcct ctttgacctc atctggggct tcatcacccc atctgattgg agcctcttcc    3360
ttctccagat tgaacaattg attgagcaga ggattgagac ccttgaaagg aacagagcca    3420
tcaccacact tcgtggcctt gctgacagct atgaaatcta cattgaagca ctccgtgagt    3480
gggaagccaa tcccaacaat gctcaactcc gtgaagatgt gaggattcgc tttgccaaca    3540
cagatgacgc tttgatcaca gccatcaaca atttcaccct caccagcttt gagatccctt    3600
tgctctcagt ctatgttcaa gctgcaaacc tccacttgag cttgcttagg gatgctgtgt    3660
ccttcggaca aggttgggga cttgacatag ccactgtcaa caatcactac aacagactca    3720
tcaacttgat tcatcgctac accaaacatt gcttggacac ctacaatcaa ggattggaga    3780
acctcagagg caccaacact cgccaatggg caaggttcaa ccagtttaga agggatctca    3840
cactcactgt gcttgacata gttgctctct tccccaacta tgatgttcgc acctacccaa    3900
ttcaaaccag ctcccaactt acaagggaaa tctacacctc ctcagtcatt gaggacagcc    3960
cagtttctgc caacatacce aatggtttca accgtgctga gtttggtgtc agaccacccc    4020
atctcatgga cttcatgaac tccttgtttg tgactgccga gactgttagg tcccaaactg    4080
tgtggggagg ccaccttgtt agctcccgca acaccgctgg caaccgcatc aacttccccat   4140 cctatgggt tttcaatcct ggtggagcca tctggattgc agatgaggac ccaaggcctt    4200
tctacagaac cttgtcagat cctgtctttg tcagaggagg ctttggcaat ccacactatg    4260
ttcttggttt gaggggagtg gcttttcagc agactggcac caatcacacc cgcacattca    4320
gaaacagcgg caccattgac agccttgatg agatcccacc tcaagacaac agcggagcac    4380
cctggaacga ctactcccat gtgctcaatc atgtcacctt tgtgcgctgg cctggtgaga    4440
tcagcggttc agattcttgg agagcaccaa tgttctcatg gacccatcgc tctgccacac    4500
ccacaaacac cattgatcca gagagaatca cccagattcc cttggtgaag gcacacacac    4560
ttcagtctgg aaccacagtt gtcagagggc ctgggttcac tggtgagac attctcagac     4620 gcacctctgg agggccattt gcttacacca ttgtcaacat caatgggcaa cttccccagc    4680
```

```
gttaccgtgc cagaatccgc tatgcttcca ccactaactt gagaatctat gtcacagttg    4740
ctggtgaaag gatctttgct ggtcagttca acaagacaat ggacactggt gatccattga    4800
cattccagtc attctcctat gccaccatca acactgcatt cacctttcca atgagccagt    4860
ccagcttcac agtgggtgca gataccttca gctccggcaa tgaggtgtac attgaccgct    4920
ttgagttgat tccagtgact gccacacttg aggctgagtc tgacttggag cgtgctcaga    4980
aggccgtgaa tgctctcttc acctcttcaa atcagattgg gctcaagaca gatgtgactg    5040
actaccatat agaccgtgtt tccaatcttg ttgagtgcct ctctgatgag ttctgcttgg    5100
atgagaagaa agagttgtca gagaaggtca agcacgccaa gaggctctct gatgagagga    5160
acttgcttca agatcccaac ttcagaggga tcaaccgtca attggatcgt ggatggaggg    5220
gatcaactga cataaccatt caaggaggtg acgatgtgtt caaggagaac tatgtcacac    5280
tcttggggac ctttgatgag tgctacccaa cataccttta ccagaagata gacgaaagca    5340
agctcaaggc ctacacaaga taccagttga gaggttacat tgaggactct caagaccttg    5400
aaatctacct catcagatac aacgccaaac atgagacagt caatgtgcct gggactggtt    5460
cactctggcc actttcagcc ccaagcccca ttggcaagtg tgcccatcac tcacatcact    5520
tctccttgga catagatgtt ggctgcactg acttgaatga ggaccttggt gtgtgggtga    5580
tcttcaagat caagacccaa gatggccatg caaggttggg caatcttgag tttcttgaag    5640
agaaaccact tgttggagaa gcccttgcca gagtgaagag ggctgagaag aaatggaggg    5700
acaagagaga gaagttggag tgggaaacaa acattgtgta caagaagcc aaagaatcag    5760 ttgatgcttt gtttgtgaac tcccaatatg ataggctcca agctgacacc aacatagcaa    5820
tgattcatgc tgcagacaaa agggttcaca gcattcgtga agcatacctt cctgaactct    5880
cagtgattcc tggggtcaat gctgcaatct ttgaagagct tgaaggacgc atcttcactg    5940
ccttctcctt gtatgatgca aggaatgtca tcaagaatgg tgacttcaac aatggccttt    6000
cctgctggaa tgtgaaaggg cacgtggatg ttgaagagca gaacaatcac cgctctgtcc    6060
ttgttgtccc tgagtgggaa gctgaagttt cacaagaagt tcgtgtctgc cctggtcgtg    6120
gctacattct tcgtgtgact gcttacaaag aaggctatgg agaaggttgt gtcaccatcc    6180
acgagataga gaacaatact gatgaattga agttcagcaa ctgtgttgag gaagaggtct    6240
acccaaacaa tactgtcact tgcaatgact acactgcaac tcaagaagag tatgagggca    6300
cttacacttc tcgcaaccgt ggctatgatg gagcctatga gagcaactca tctgtgcctg    6360
ctgactatgc ttcagcctat gaagagaagg catacactga tggaaggcgt gacaatcctt    6420
gtgaaagcaa cagaggctat ggggactaca cacccctccc agctggctat gtgaccaaag    6480
agttggagta ctttcctgaa actgacaagg tttggattga gataggagaa actgaaggca    6540
cattcatagt tgactctgtg gagcttttgc tcatggaaga gtgagtagtt agcttaatca    6600
cctagagctc ggtcaccagc ataattttta ttaatgtact aaattactgt tttgttaaat    6660
gcaattttgc tttctcggga ttttaatatc aaaatctatt tagaaataca caatatttg    6720 ttgcaggctt gctggagaat cgatctgcta tcataaaaat tacaaaaaaa tttatttgc    6780 ctcaattatt ttaggattgg tattaaggac gcttaaatta tttgtcgggt cactacgcat    6840
cattgtgatt gagaagatca gcgatacgaa atattcgtag tactatcgat aatttatttg    6900
aaaattcata agaaaagcaa acgttacatg aattgatgaa acaatacaaa gacagataaa    6960
gccacgcaca tttaggatat tggccgagat tactgaatat tgagtaagat cacggaattt    7020
```

```
ctgacaggag catgtcttca attcagccca aatggcagtt gaaatactca aaccgcccca    7080
tatgcaggag cggatcattc attgtttgtt tggttgcctt tgccaacatg ggagtccaag    7140
gttgcggccg cgcgccgaaa acaactttgt atacaaaagt tgccgcggtg actgactgaa    7200
ctaaacccag aaggtaatta tccaagatgt agcatcaaga atccaatgtt tacgggaaaa    7260
actatggaag tattatgtaa gctcagcaag aagcagatca atatgcggca catatgcaac    7320
ctatgttcaa aaatgaagaa tgtacagata caagatccta tactgccaga atacgaagaa    7380
gaatacgtag aaattgaaaa agaagaacca ggcgaagaaa agaatcttga agacgtaagc    7440
actgacgaca caatgaaaaa gaagaagata aggtcggtga ttgtgaaaga gacatagagg    7500
acacatgtaa ggtggaaaat gtaagggcgg aaagtaacct tatcacaaag gaatcttatc    7560
ccccactact tatccttta tattttccg tgtcattttt gcccttgagt tttcctatat    7620
aaggaaccaa gttcggcatt tgtgaaaaca agaaaaaatt tggtgtaagc tattttcttt    7680
gaagtactga ggatacaact tcagagaaat ttgtaagttt gtagatccaa caatggacaa    7740
caatcccaac atcaacgagt gcattcctta caactgcctg agcaaccctg aggttgaggt    7800
gctgggtgga gaacggattg agactggtta cacacctatc gacatctcgt tgtcacttac    7860
ccaattcctt ttgtcagagt tcgtgcccgg tgctggattc gtgcttggac ttgtcgatat    7920
catttgggga atctttggtc cctctcaatg ggacgccttt cttgtacaga tagagcagtt    7980
aattaaccaa agaatagaag aattcgctag gaaccaagcc atctcaaggt tagaaggcct    8040
cagcaacctt taccagattt acgcagaatc ttttcgagag tgggaagcag acccgaccaa    8100
tcctgcctta agagaggaga tgcgcattca attcaatgac atgaacagcg cgctgacgac    8160
cgcaattccg ctcttcgccg ttcagaatta ccaagttcct cttttatccg tgtacgtgca    8220
ggctgccaac ctgcacttgt cggtgctccg cgatgtctcc gtgttcggac aacggtgggg    8280
ctttgatgcc gcaactatca atagtcgtta taatgatctg actaggctta ttggcaacta    8340
taccgattat gctgttcgct ggtacaacac gggtctcgaa cgtgtctggg accggattc    8400 tagagattgg gtcaggtaca accagttcag gcgagagttg acactaactg tcctagacat    8460
tgtcgctctc tttcccaact acgactctag gcgctaccca atccgtactg tgtcacaatt    8520
gacccgggaa atctacacaa acccagtcct cgagaacttc gacggtagct ttcgaggctc    8580
ggctcagggc atagagagaa gcatcaggtc tccacacctg atggacatat tgaacagtat    8640
cacgatctac accgatgcgc accgcggtta ttactactgg tcagggcatc agatcatggc    8700
atcacccgtt gggttctctg gaccagaatt cactttccca cttttacggga ctatgggcaa    8760 tgcagctcca caacaacgta ttgttgctca actcggtcag ggcgtgtata gaaccttgtc    8820
cagcactcta tataggagac ctttcaacat cggcatcaac aatcaacaat tgtctgtgct    8880
tgacgggaca gaatttgcct atggaacctc ctcaaatctg ccatccgctg tctacagaaa    8940
gagcggaaca gttgatagct tggatgagat ccctccacag aacaacaacg ttccacctag    9000
gcaagggttt agccatcgcc ttagccatgt gtccatgttc cgttcaggct ttagtaatag    9060
cagcgttagt atcatcagag ctccgatgtt ctcttggata catcgtagtg ctgagtttaa    9120
caacataatt gcatccgata gcattactca gatcccagct gtcaagggga actttctctt    9180
taatggttct gtcatttcag gaccaggatt cactggaggc gacttggtta ggctgaattc    9240
ttccggcaac aacatccaga atagagggta tattgaagtg cccattcact tcccatcgac    9300
atctaccaga tatcgtgttc gtgtaaggta tgcctctgtt accccctattc acctcaacgt    9360 caattggggt aattcctcca tctttttccaa tacagtacca gcgacagcta catccttgga    9420
```

```
taatctccaa tctagcgatt tcggttactt cgaaagtgcc aatgccttca cctcttccct   9480
aggtaacata gtaggtgtta gaaatttctc cggaaccgcc ggagtgataa tcgaccgctt   9540
cgaattcatt cccgttactg caacgctcga ggcagagtct gacttggaaa gagcacagaa   9600
ggcggtgaat gctctgttca cttcgtccaa tcagattggg ctcaagacag atgtgactga   9660
ctatcacatc gatcgcgttt ccaaccttgt tgagtgcctc tctgatgagt tctgtttgga   9720
tgagaagaag gagttgtccg agaaggtcaa acatgctaag cgacttagtg atgagcggaa   9780
cttgcttcaa gatcccaact ttcgcgggat caacaggcaa ctagatcgtg gatggagggg   9840
aagtacggac atcaccattc aaggaggtga tgatgtgttc aaggagaact atgttacgct   9900
cttgggtacc tttgatgagt gctatccaac ataccctgtac cagaagatag atgaatcgaa   9960
actcaaagcc tacacaagat accagttgag aggttacatc gaggacagtc aagaccttga  10020
gatctacctc atcagataca acgccaaaca tgagacagtc aatgtgcctg gacgggttc   10080 actctggcca ctttcagccc caagtccat cggcaagtgt gcccatcact cacaccactt  10140
ctccttggac atagacgttg gctgtaccga cctgaacgaa gacctcggtg tgtgggtgat  10200
cttcaagatc aagactcaag atggccatgc caggctaggc aatctggagt ttctagaaga  10260
gaaaccactt gttggagaag ccctcgctag agtgaagagg gctgagaaga gtggaggga  10320 caagagagag aagttggaat gggaaacaaa cattgtgtac aaagaagcca agaaagcgt   10380 tgacgctctg tttgtgaact ctcagtatga taggctccaa gctgatacca acatagctat  10440
gattcatgct gcagacaaac gcgttcatag cattcgggaa gcttaccttc ctgaacttag  10500
cgtgattccg ggtgtcaatg ctgctatctt tgaagagtta gaagggcgca tcttcactgc  10560
attctccttg tatgatgcga ggaatgtcat caagaatggt gacttcaaca atggcctatc  10620
ctgctggaat gtgaaagggc acgtagatgt agaagaacag aacaatcacc gctctgtcct  10680
tgttgttcct gagtgggaag cagaagtttc acaagaagtt cgtgtctgtc ctggtcgtgg  10740
ctacattctt cgtgttaccg cgtacaaaga aggatacgga gaaggttgcg tcaccataca  10800
cgagattgag aacaacaccg acgagctgaa gttcagcaac tgcgtcgagg aggaagtcta  10860
cccaaacaac accgtaactt gcaatgacta cactgcgact caagaggagt atgagggtac  10920
ttacacttct cgcaatcgag gatacgatgg agcctatgag agcaactctt ctgtacccgc  10980
tgactatgca tcagcctatg aggagaaggc ttacaccgat ggacgtaggg acaatccttg  11040
cgaatctaac agaggctatg gggactacac accgttacca gccggctatg tcaccaaaga  11100
gttagagtac tttccagaaa ccgacaaggt ttggattgag attggagaaa cggaaggaac  11160
attcattgtt gatagcgtgg agttacttct gatggaggaa tgagtagtta gcttaatcac  11220
ctagagctcg gttacctatc aaaatctatt tagaaataca caatattttg ttgcaggctt  11280
gctggagaat cgatctgcta tcataaaaat tacaaaaaaa ttttatttgc ctcaattatt  11340
ttaggattgg tattaaggac gcttaaatta tttgtcgggt cactacgcat cattgtgatt  11400
gagaagatca gcgatacgaa atattcgtag tactatcgat aatttatttg aaaattcata  11460
agaaaagcaa acgttacatg aattgatgaa acaatacaaa gacagataaa gccacgcaca  11520
tttaggatat tggccgagat tactgaatat tgagtaagat cacggaattt ctgacaggag  11580
catgtcttca attcagccca aatggcagtt gaaatactca aaccgcccca tatgcaggag  11640
cggatcattc attgtttgtt tggttgcctt tgccaacatg ggagtccaag gttgcggccg  11700
cgcgccgacc cagctttctt gtacaaagtg gttgcggccg cttaattaaa tttaaatgcc  11760
```

```
cgggcgttta aacgcggccg cttaattaag gccggcctgc agcaaaccca gaaggtaatt   11820
atccaagatg tagcatcaag aatccaatgt ttacgggaaa aactatggaa gtattatgta   11880
agctcagcaa gaagcagatc aatatgcggc acatatgcaa cctatgttca aaaatgaaga   11940
atgtacagat acaagatcct atactgccag aatacgaaga agaatacgta gaaattgaaa   12000
aagaagaacc aggcgaagaa aagaatcttg aagacgtaag cactgacgac aacaatgaaa   12060
agaagaagat aaggtcggtg attgtgaaag agacatagag gacacatgta aggtggaaaa   12120
tgtaagggcg gaaagtaacc ttatcacaaa ggaatcttat cccccactac ttatccttt   12180
atatttttcc gtgtcatttt tgcccttgag ttttcctata taaggaacca agttcggcat   12240
ttgtgaaaac aagaaaaaat ttggtgtaag ctattttctt tgaagtactg aggatacaac   12300
ttcagagaaa tttgtaagtt tgtagatctc catgtctccg gagaggagac cagttgagat   12360
taggccagct acagcagctg atatggccgc ggtttgtgat atcgttaacc attacattga   12420
gacgtctaca gtgaacttta ggacagagcc acaaacacca caagagtgga ttgatgatct   12480
agagaggttg caagatagat acccttggtt ggttgctgag gttgagggtg ttgtggctgg   12540
tattgcttac gctgggccct ggaaggctag gaacgcttac gattggacag ttgagagtac   12600
tgtttacgtg tcatataggc atcaaaggtt gggcctagga tccacattgt acacacattt   12660
gcttaagtct atggaggcgc aaggttttaa gtctgtggtt gctgttatag gccttccaaa   12720
cgatccatct gttaggttgc atgaggcttt gggatacaca gcccggggta cattgcgcgc   12780
agctggatac aagcatggtg gatggcatga tgttggtttt tggcaaaggg attttgagtt   12840
gccagctcct ccaaggccag ttaggccagt tacccagatc tgaggtaccc tgagcttgag   12900
cttatgagct tatgagctta gagctcggat ccactagtaa cggccgccag tgtgctggaa   12960
ttcgcccttg actagatagg cgcccagatc ggcggcaata gcttcttagc gccatcccgg   13020
gttgatccta tctgtgttga aatagttgcg gtgggcaagg ctctctttca gaaagacagg   13080
cggccaaagg aacccaaggt gaggtgggct atggctctca gttccttgtg gaagcgcttg   13140
gtctaaggtg cagaggtgtt agcgggatga agcaaaagtg tccgattgta acaagatatg   13200
ttgatcctac gtaaggatat taaagtatgt attcatcact aatataatca gtgtattcca   13260
atatgtacta cgatttccaa tgtctttatt gtcgccgtat gtaatcggcg tcacaaaata   13320
atccccggtg actttctttt aatccaggat gaaataatat gttattataa ttttgcgat   13380
ttggtccgtt ataggaattg aagtgtgctt gcggtcgcca ccactcccat ttcataattt   13440
tacatgtatt tgaaaaataa aaatttatgg tattcaattt aaacacgtat acttgtaaag   13500
aatgatatct tgaaagaaat atagtttaaa tatttattga taaaataaca agtcaggtat   13560
tatagtccaa gcaaaaacat aaattttattg atgcaagttt aaattcagaa atatttcaat   13620
aactgattat atcagctggt acattgccgt agatgaaaga ctgagtgcga tattatggtg   13680
taatacatag cggccgggtt tctagtcacc ggttaggatc cgtttaaact cgaggctagc   13740
gcatgcacat agacacacac atcatctcat tgatgcttgg taataattgt cattagattg   13800
ttttttatgca tagatgcact cgaaatcagc caattttaga caagtatcaa acggatgtga   13860
cttcagtaca ttaaaaacgt ccgcaatatg atattcatta atttttatatt atctaaaaga   13920
gttaaaagag aaaaaagaaa tatgacaatt ttttctttc acatcttcta acctaaaagt   13980
atgactctat ggaggctaag tttagaaaaa gatacggatc tagggtgtgg aaacatcaat   14040
ggtcaactcc ttttatattt caatcaattg ggttttgctt tatctttaca ttttctcctt   14100
ttattttcca cgtctattca aatctacttg ttagcgggtg attactcttt tttctttat   14160
```

```
agatgccaat tatttctctc ctatgtatta aattagagta tattgtcttg aaagtgactt    14220 agtatttag tttatagtct cttaaagaac gacacctttt attcttaact ctctttatca     14280
agttttaatt taaaattatt ttaaattaag tatgcataca tatcttaata tttttcttaa    14340
ttatttttaa attccctaaa tttaatgttt tcatacaatg taagagatat acatattaat    14400
tatatttaaa gataaaactt actttcctgc aataaaataa agaaaaggac agtcatacaa    14460
ttatataatt aatccagaat atttatagct tttaaacatt tattttctat caattaagta    14520
ataactttaa ataaaattaa gagtacttt ttatactcca aagaatttat ttattttcaa     14580
caaaatcgtc tgactgtttc aattgatcat tatcagccta gcataaccta aatttcattt    14640
tcaaacataa cttttggcac caaatcaccc ggcattgcaa aaaagtcttt tgcgatatga    14700
ccctccacga cgcagaacca ctgttattca ttaccatcac ttttaatcct aatttcccat    14760
acacttaccc tttccatgac atcttcaaag cctttatttt gcttttcttg tttaagctgt    14820
tttaacctaa tttcatgcat ataaacaaag agtaaagcaa aggcaaatat ttgtacgtat    14880
agtttttaga cagaaaagga aagtaaatta tagagataat gaagtttgct cttttaaatt    14940
cgtcgtgatg ttatccatca tatctaaatg cttattcctg tttttgtctt ttttctcttt    15000
taccggagtt tattttatat aattaattaa agttagtaga tctatattct ttttcataga    15060
taatccatct tctttggagg cacatcgatc attaatcata gagttttgag aagcattatc    15120
actaaagctt caattaatta tatccaataa acggtattgg tgtatgatgt tatgatagca    15180
aatagataat ctaatctata cgagccacaa aagggggcatg aactctatct cgaagaaatt   15240
ggagatgaag ggattgagat tggcaccttg tgctattatt gcccactaat catt          15294
```

STACKED HERBICIDE TOLERANCE EVENT 8291.45.36.2, RELATED TRANSGENIC SOYBEAN LINES, AND DETECTION THEREOF

CROSS-REFERENCE TO RELATED APPLICATIONS

This application is a National Stage filing of International Application Serial No. PCT/US2011/063133, filed Dec. 2, 2011 and designating the United States, which claims priority to U.S. Provisional Application Ser. No. 61/419,709 filed Dec. 3, 2010, U.S. Provisional Application Ser. No. 61/471,845 filed Apr. 5, 2011, U.S. Provisional Application Ser. No. 61/511,664 filed Jul. 26, 2011, and U.S. Provisional Application Ser. No. 61/521,798 filed Aug. 10, 2011, the disclosures of which are expressly incorporated herein by reference.

BACKGROUND OF THE INVENTION

Glyphosate (N-phosphonomethylglycine), a broad-spectrum herbicide, inhibits 5-enolpyruvylshikimate-3-phosphate synthase (EPSPS), an enzyme in the shikimate biosynthetic pathway that produces the essential aromatic amino acids in plant cells Inhibition of EPSPS effectively disrupts protein synthesis and thereby kills the affected plant cells. Because glyphosate is non-selective, it kills both weeds and crop plants. Thus it is useful with crop plants when one can modify the crop plants to be resistant to glyphosate, allowing the desirable plants to survive exposure to the glyphosate.

Recombinant DNA technology has been used to isolate mutant EPSP synthases that are glyphosate-resistant. Such glyphosate-resistant mutant EPSP synthases can be transformed into plants and confer glyphosate-resistance upon the transformed plants. By way of example, a glyphosate tolerance gene was isolated from *Agrobacterium* strain CP4 as described in U.S. Pat. No. 5,633,435. This reference and all references cited herein are hereby incorporated by reference.

Other glyphosate tolerance genes have been created through the introduction of mutations. These include the AroA gene isolated by Comai and described at U.S. Pat. Nos. 5,094,945, 4,769,061, and 4,535,060. A single mutant has been utilized, as described in U.S. Pat. No. 5,310,667, by substituting an alanine residue for a glycine residue between amino acid positions 80 and 120. Double mutants have been described in U.S. Pat. Nos. 6,225,114 and 5,866,775 in which, in addition to the above mutation, a second mutation (a threonine residue for an alanine residue between positions 170 and 210) was introduced into a wild-type EPSPS gene.

Other work resulted in the production of glyphosate resistant maize through the introduction of a modified maize EPSPS gene bearing mutations at residue 102 (changing threonine to isoleucine) and residue 106 (changing proline to serine) of the amino acid sequence encoded by GenBank Accession No. X63374. See U.S. Pat. Nos. 6,566,587 and 6,040,497.

Examples of events providing resistance to glyphosate in soybeans include soybean line GTS 40-3-2 (Padgette et al. 1995), soybean event MON89788 (U.S. Pat. No. 7,608,761), U.S. Pat. No. 7,608,761 relates to soybean event MON89788, each of which was produced by inserting the cp4 epsps gene into soybean.

The widespread adoption of the glyphosate tolerant cropping system and the increasing use of glyphosate has contributed to the prevalence of glyphosate-resistant and difficult-to-control weeds in recent years. In areas where growers are faced with glyphosate resistant weeds or a shift to more difficult-to-control weed species, growers can compensate for glyphosate's weaknesses by tank mixing or alternating with other herbicides that will control the missed weeds.

One popular and efficacious tankmix partner for controlling broadleaf escapes in many instances has been 2,4-dichlorophenoxyacetic acid (2,4-D). 2,4-D, which has been used as a herbicide for more than 60 years, provides broad spectrum, post-emergence control of many annual, biennial, and perennial broadleaf weeds including several key weeds in corn, soybeans, and cotton. Key weeds controlled by 2,4-D (560-1120 g ae/ha rates) in row crop production include *Ambrosia artemisiifolia, Ambrosia trifida, Xanthium strumarium, Chenopodium album, Helianthus annuus, Ipomoea* sp., *Abutilon theophrasti, Conyza Canadensis*, and *Senna obtusifolia*. 2,4-D provides partial control of several key weeds including *Polygonum pensylvanicum, Polygonum persicaria, Cirsium arvense, Taraxacum officinale*, and *Amaranthus* sp. including *Amaranthus rudis*, and *Amaranthus palmeri*.

A limitation to further use of 2,4-D is that its selectivity in dicot crops like soybean or cotton is very poor, and hence 2,4-D is not typically used on (and generally not near) sensitive dicot crops. Additionally, 2,4-D's use in grass crops is somewhat limited by the nature of crop injury that can occur. 2,4-D in combination with glyphosate has been used to provide a more robust burndown treatment prior to planting no-till soybeans and cotton; however, due to these dicot species' sensitivity to 2,4-D, these burndown treatments must occur at least 14-30 days prior to planting (Agriliance, 2005).

One organism that has been extensively researched for its ability to degrade 2,4-D is *Ralstonia eutropha*, which contains a gene that codes for tfdA (Streber et al., 1987), an enzyme which catalyzes the first step in the mineralization pathway. (See U.S. Pat. No. 6,153,401 and GENBANK Acc. No. M16730). tfdA has been reported to degrade 2,4-D (Smejkal et al., 2001). The products that result from the degradation have little or no herbicidal activity compared to 2,4-D. tfdA has been used in transgenic plants to impart 2,4-D resistance in dicot plants (e.g., cotton and tobacco) normally sensitive to 2,4-D (Streber et al. (1989), Lyon et al. (1989), Lyon (1993), and U.S. Pat. No. 5,608,147).

A number of tfdA-type genes that encode proteins capable of degrading 2,4-D have been identified from the environment and deposited into the Genbank database. Many homologues are similar to tfdA (>85% amino acid identity). However, there are a number of polynucleotide sequences that have a significantly lower identity to tfdA (25-50%), yet have the characteristic residues associated with α-ketoglutarate dioxygenase Fe (II) dioxygenases.

An example of a 2,4-D-degrading gene with low homology (<35%) to tfdA is the aad-12 gene from *Delftia acidovorans* (US Patent App 2011/0203017). The aad-12 gene encodes an S-enantiomer-specific α-ketoglutarate-dependent dioxygenase which has been used in plants to confer tolerance to certain phenoxy auxin herbicides, including, but not limited to: phenoxyacetic acid herbicides such as 2,4-D and MCPA; phenoxybutanoic acid herbicides (e.g., 2,4-DB and MCPB); and pyridyloxyalkanoic acid herbicides (e.g., pyridyloxyacetic acid herbicides such as triclopyr and fluoroxypyr), and including acid, salt, or ester forms of the active ingredient(s). (See, e.g., WO 2007/053482).

Glufosinate-ammonium ("glufosinate") is a non-systemic, non-selective herbicide in the phosphinothricin class of herbicides. Used primarily for post-emergence control of a wide range of broadleaf and grassy weeds, L-phosphinothricin, the active ingredient in glufosinate, controls weeds through the irreversible inhibition of glutamine-synthase, an enzyme which is necessary for ammonia detoxification in plants. Glufosinate herbicides are sold commercially, for example, under the brand names Ignite®, BASTA® and Liberty®.

The enzyme phosphinothricin N-acetyl transferase (PAT), isolated from the soil bacterium *Streptomyces viridochromogenes*, catalyzes the conversion of L-phosphinothricin to its inactive form by acetylation. A plant-optimized form of the gene expressing PAT has been used in soybeans to confer tolerance to glufosinate herbicide. One such example of glufosinate resistant soybeans is event A5547-127. Most recently, the use of glufosinate herbicide in combination with the glufosinate-tolerance trait has been proposed as a non-selective means to effectively manage ALS- and glyphosate resistant weeds.

The expression of heterologous or foreign genes in plants is influenced by where the foreign gene is inserted in the chromosome. This could be due to chromatin structure (e.g., heterochromatin) or the proximity of transcriptional regulation elements (e.g., enhancers) close to the integration site (Weising et al., *Ann. Rev. Genet.* 22:421-477, 1988), for example. The same gene in the same type of transgenic plant (or other organism) can exhibit a wide variation in expression level amongst different events. There may also be differences in spatial or temporal patterns of expression. For example, differences in the relative expression of a transgene in various plant tissues may not correspond to the patterns expected from transcriptional regulatory elements present in the introduced gene construct.

Thus, large numbers of events are often created and screened in order to identify an event that expresses an introduced gene of interest to a satisfactory level for a given purpose. For commercial purposes, it is common to produce hundreds to thousands of different events and to screen those events for a single event that has desired transgene expression levels and patterns. An event that has desired levels and/or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

BRIEF SUMMARY OF THE INVENTION

The subject invention relates, in part, to effective means for managing weed resistance, which helps preserve the usefulness of herbicide-tolerant technologies. In some embodiments, the subject invention can provide growers with great flexibility and convenience in weed control options.

More specifically, the present invention relates in part to the soybean (*Glycine max*) event designated pDAB8291.45.36.2 ("Event pDAB8291.45.36.2") having representative seed deposited with American Type Culture Collection (ATCC) with Accession No. PTA-11335, and progeny derived thereof. The subject invention includes soybean plants comprising Event pDAB8291.45.36.2 (and includes soybean plants comprising a transgenic insert in a genomic segment comprising SEQ ID NO:1 and SEQ ID NO:2).

The transgenic insert present in the subject event and deposited seed comprises three herbicide tolerance genes: aad-12, 2mepsps, and a pat gene. The aad-12 gene, derived from *Delftia acidovorans*, encodes the aryloxyalkanoate dioxygenase (AAD-12) protein, which confers tolerance to, e.g., 2,4-dichlorophenoxyacetic acid and pyridyloxyacetate herbicides. The 2mepsps gene, a modified EPSPS sequence isolated from maize, produces a protein which confers tolerance to glyphosate herbicides. The pat gene, from the soil bacterium *Streptomyces viridochromogenes*, confers tolerance to the herbicide glufosinate.

Other aspects of the invention comprise progeny plants, soybeans, seeds, and/or regenerable parts of the plants and seeds and progeny comprising soybean event pDAB8291.45.36.2, as well as food or feed products made from any thereof. The invention also includes plant parts of Event pDAB8291.45.36.2 that include, but are not limited to, pollen, ovule, flowers, shoots, roots, leaves, nuclei of vegetative cells, pollen cells, and other plant cells that comprise Event pDAB8291.45.36.2. The invention further relates to soybean plants having tolerance to multiple herbicides including phenoxyacetic acid herbicides, phenoxybutanoic acid herbicides, pyridyloxyalkanoic acid herbicides, glyphosate, and/or glufosinate. Such soybean plants may also be stacked with genes that confer tolerance to various other non-selective and selective herbicides, including but not limited to dicamba, imidazolinone, and HPPD herbicides. The invention further includes novel genetic compositions Event pDAB8291.45.36.2 and aspects of agronomic performance of soybean plants comprising Event pDAB8291.45.36.2.

This invention relates in part to plant breeding and herbicide tolerant plants. This invention includes a novel transformation event in soybean plants comprising a polynucleotide, as described herein, inserted into a specific site within the genome of a soybean cell.

In some embodiments, said event/polynucleotide can be "stacked" with other traits, including, for example, agronomic traits and/or insect-inhibitory proteins. However, the subject invention includes plants having the single event, as described herein.

In some embodiments, the subject herbicide tolerance event can be combined in a breeding stack with an insect resistance event. In some of these embodiments, the insect resistance event comprises a cry1F gene and a cry1Ac gene. Some such events and stacks are specifically exemplified herein, including soybean event 9582.812.9.1 ("the 812 Event") and soybean event 9582.814.19.1 ("the 814 Event"). Plants, plant cells, and seeds, for example, comprising any combination of the subject events are included in the subject invention.

The additional traits may be stacked into the plant genome, or into the same locus as Event pDAB8291.45.36.2, for example via plant breeding, re-transformation of the transgenic plant containing Event DAS-8291.45.36.2, or addition of new traits through targeted integration via homologous recombination.

Other embodiments include the excision of a portion or all of the transgenic insert and/or flanking sequences of Event DAS-8291.45.36.2. Upon excision, another and/or additional insert can be targeted to the specific chromosomal site of Event DAS-8291.45.36.2. The exemplified insert can be replaced, or further insert(s) can be stacked, in this manner, with the exemplified insert of the subject soybean event.

In one embodiment, the present invention encompasses a soybean chromosomal target site located on chromosome 03. In some embodiments, the target site comprises a heterologous nucleic acid. In some embodiments, the soybean chromosomal target site is located between or within the genomic flanking sequences set forth in SEQ ID NO:1 and SEQ ID NO:2.

In one embodiment, the present invention encompasses a method of making a transgenic soybean plant comprising inserting a heterologous nucleic acid at a position on chromosome 03. In another embodiment, the heterologous nucleic acid is inserted on chromosome 03 near or between various exemplified polynucleotide segments as described herein.

Additionally, the subject invention provides assays for detecting the presence of the subject event in a sample (of soybeans, for example). The assays can be based on the DNA sequence of the recombinant construct, inserted into the soybean genome, and on the genomic sequences flanking the insertion site. Kits and conditions useful in conducting the assays are also provided.

Thus, the subject invention relates in part to the cloning and analysis of the DNA sequences of the whole exemplified insert and the border regions thereof (in transgenic soybean lines). These sequences are unique. Based on these insert and border (and junction) sequences, event-specific primers can be and were generated. PCR analysis demonstrated that the event can be identified by analysis of the PCR amplicons generated with these event-specific primer sets. Thus, these and other related procedures can be used to uniquely identify soybean lines comprising the event of the subject invention.

The subject invention also relates in part to realtime or endpoint TaqMan PCR assays for the detection of event 8291.45.36.2. Some embodiments are directed to assays that are capable of high throughput zygosity analysis. The subject invention further relates, in part, to the use of a GMFL01-25-J19 (GenBank: AK286292.1) reference gene for use in determining zygosity. These and other related procedures can be used to uniquely identify the zygosity of Event pDAB8291.45.36.2 and breed soybean lines comprising the event.

BRIEF DESCRIPTION OF THE FIGURES

FIG. 1 is a plasmid map of pDAB8291.

FIG. 2 is a schematic diagram depicting primer locations for soybean Event pDAB8291.45.36.2.

FIG. 3 is a schematic diagram depicting primer locations and genomic DNA deletion in soybean Event pDAB8291.45.36.2.

FIG. 4 is a schematic diagram depicting primer locations for soybean Event pDAB8291.45.36.2

BRIEF DESCRIPTION OF THE SEQUENCES

SEQ ID NO:1 provides the 5' flanking border sequence for the subject soybean Event pDAB8291.45.36.2.
SEQ ID NO:2 provides the 3' flanking border sequence for the subject soybean Event pDAB8291.45.36.2.
SEQ ID NO:3 provides primer 4536_WF1.
SEQ ID NO:4 provides primer 4536_WF2.
SEQ ID NO:5 provides primer 4536_WF3.
SEQ ID NO:6 provides primer 4536_WF4.
SEQ ID NO:7 provides primer 4536_WR1.
SEQ ID NO:8 provides primer 4536_WR2.
SEQ ID NO:9 provides primer 4536_WR3.
SEQ ID NO:10 provides primer 4536_WR4.
SEQ ID NO:11 provides primer ED_v2_C1.
SEQ ID NO:12 provides primer PAT_11.
SEQ ID NO:13 provides sequence for plasmid pDAB8291.
SEQ ID NO:14 provides partial 5' soybean genomic flanking and partial 5' insert sequence.
SEQ ID NO:15 provides partial 3' soybean genomic flanking and partial 3' insert sequence.
SEQ ID NO:16 provides a 72 base pair sequence spanning the 5' integration junction.
SEQ ID NO:17 provides a 142 base pair sequence spanning the 3' integration junction.
SEQ ID NO:18 provides primer 4536_5'F.
SEQ ID NO:19 provides primer 4536_5'R.
SEQ ID NO:20 provides probe 4536_5'P.
SEQ ID NO:21 provides primer 4536_3'F.
SEQ ID NO:22 provides primer 4536_3'R.
SEQ ID NO:23 provides probe 4536_3'P.
SEQ ID NO:24 provides primer GMS 116F.
SEQ ID NO:25 provides primer GMS116R.
SEQ ID NO:26 provides probe GMS116Probe.
SEQ ID NO:27 provides the expected sequence of soybean Event pDAB8291.45.36.2.
SEQ ID NO:28 provides the expected sequence of Soybean Event 9582.812.9.1, including the 5' genomic flanking sequence, pDAB9582 T-strand insert, and 3' genomic flanking sequence.
SEQ ID NO:29 provides the expected sequence of Soybean Event 9582.814.19.1, including the 5' genomic flanking sequence, pDAB9582 T-strand insert, and 3' genomic flanking sequence.

DETAILED DESCRIPTION OF THE INVENTION

The invention described herein includes novel transformation events of soybean plants (soybean) comprising a cassette for the expression of multiple herbicide tolerance genes inserted into a specific locus within the genome of a soybean cell.

The exemplified transgenic insert comprising Event pDAB8291.45.36.2 includes genetic elements for the expression of three different herbicide tolerance genes: (1) a synthetic aad-12 gene; (2) a codon-optimized, modified EPSPS sequence from maize encoding a protein containing mutations, as compared to the wild-type EPSPS polypeptide: at amino acid residues 102 (from threonine to isoleucine) and 106 (from proline to serine) and which confers resistance or tolerance to glyphosate herbicides; and (3) a pat gene which confers tolerance or resistance to the glufosinate herbicides. The aad-12 gene was derived from *Delftia acidovorans* and encodes an aryloxyalkanoate dioxygenase (AAD-12) protein enzyme capable of deactivating herbicides having an α-ketoglutarate moiety, including phenoxyalkanoate herbicides (e.g., phenoxyacetic acid herbicides such as 2,4-D and MCPA; and phenoxybutanoic acid herbicides such as 2,4-DB and MCPB) and pyridyloxyalkanoic acid herbicides (e.g., pyridyloxyacetic acid herbicides such as triclopyr and fluoroxypyr), including acid, salt, or ester forms of the active ingredient(s)

More specifically, the subject invention relates in part to transgenic soybean Event pDAB8291.45.36.2, plant lines comprising these events, and the cloning and analysis of the DNA sequences of this insert, and/or the border regions thereof. Plant lines of the subject invention can be detected using sequences disclosed and suggested herein.

In some embodiments, a polynucleotide segment exemplified or described herein (such as SEQ ID NO:1, SEQ ID NO:2, and/or the insert therebetween, as depicted in FIG. 2 for example) can be excised and/or subsequently re-targeted with additional polynucleotide sequence(s).

This invention relates in part to plant breeding and herbicide tolerant plants. In some embodiments, said polynucleotide sequence can be "stacked" with other traits (such as other herbicide tolerance gene(s) and/or gene(s) that encode insect-inhibitory proteins or inhibitory RNA sequences, for example). However, the subject invention also includes plants having a single event, as described herein.

In some embodiments, the subject herbicide tolerance event can be combined in a breeding stack with an insect resistance event. In some embodiments, the insect resistance event is selected from the group consisting of the 812 Event and the 814 Event (as defined in greater detail below), each of which comprises a cry1F gene and a cry1Ac gene. Plants, plant cells, and seeds, for example, comprising any combination of the subject events are included in the subject invention.

U.S. provisional application Ser. No. 61/471,845, filed Apr. 5, 2011, relates in part to soybean lines comprising Soybean Event 9582.812.9.1 (the 812 Event). Seeds comprising this event were deposited and made available to the public without restriction (but subject to patent rights), with the American Type Culture Collection (ATCC), 10801 University Boulevard, Manassas, Va., 20110. The deposit, designated as ATCC Deposit No. PTA-11602, was made on Jan. 20, 2011. This deposit was made and will be maintained in accordance with and under the terms of the Budapest Treaty with respect to seed deposits for the purposes of patent procedure.

U.S. provisional application Ser. Nos. 61/511,664 (filed Jul. 26, 2011) and 61/521,798 (filed Aug. 10, 2011) relates in part to soybean lines comprising soybean event 9582.814.19.1 (the 814 Event). Seeds comprising this event were deposited with the American Type Culture Collection (ATCC), 10801 University Boulevard, Manassas, Va., 20110. The deposit, ATCC Patent Deposit Designation PTA-12006, was received by the ATCC on Jul. 21, 2011. This deposit was made and will be maintained in accordance with and under the terms of the Budapest Treaty with respect to seed deposits for the purposes of patent procedure.

The subject invention also includes plants, seeds, and plant cells, for example, comprising SEQ ID NO:27 (Event pDAB8291.45.36.2 (also called "the 4536 Event"), SEQ ID NO:28 (the 812 Event), and/or SEQ ID NO:29 (the 814 Event), and variants of these sequences having, for example, at least 95,%, 96%, 97%, 98%, or 99% identity with such sequences. It is not uncommon for some variation (such as deletion of some segments) to occur upon integration of an insert sequence within the plant genome. This is discussed in more detail in Example 7, for example.

The subject invention also provides assays for detecting the presence of the subject event in a sample. Aspects of the subject invention include methods of designing and/or producing any diagnostic nucleic acid molecules exemplified or suggested herein, particularly those based wholly or partially on the subject flanking sequences.

In some embodiments, this invention relates to herbicide-tolerant soybean lines, and the identification thereof. The subject invention relates in part to detecting the presence of the subject event in order to determine whether progeny of a sexual cross contain the event of interest. In addition, a method for detecting the event is included and is helpful, for example, for complying with regulations requiring the pre-market approval and labeling of foods derived from recombinant crop plants, for example. It is possible to detect the presence of the subject event by any well-known nucleic acid detection method such as polymerase chain reaction (PCR) or DNA hybridization using nucleic acid probes. Event-specific PCR assays are discussed herein. (See e.g. Windels et al. (Med. Fac. Landbouww, Univ. Gent 64/5b: 459462, 1999) for another example.) Some of these examples relate to using a primer set spanning the junction between the insert and flanking DNA. More specifically, one primer included sequence from the insert and a second primer included sequence from flanking DNA as described herein.

Exemplified herein is soybean Event pDAB8291.45.36.2, and its selection and characterization for stability and expression in soybean plants from generation to generation. Both flanking sequences of Event pDAB8291.45.36.2 have been sequenced and are described herein as SEQ ID NO:1 and SEQ ID NO:2. Event specific assays were developed. It has also been mapped onto the soybean genome (soybean chromosome 03). Event pDAB8291.45.36.2 can be introgressed into elite cultivars where it will confer tolerance to phenoxy auxin, glyphosate and glufosinate herbicides in inbred and hybrid soybean lines.

The version of the gene encoding the mutant 5-enolpyruvyl-3-phosphoshikimic acid synthase (EPSPS) used in preferred embodiments of the subject invention is hemicot codon-usage-optimized (for both dicots and monocots). The wild-type EPSPS gene was isolated from *Zea mays*, and the wild-type sequence was deposited under GenBank accession number X63374. See also U.S. Pat. No. 6,566,587 (in particular, SEQ ID No. 3 therein).

To obtain high expression of heterologous genes in plants, it may be preferred to reengineer said genes so that they are more efficiently expressed in plant cells. Modification of the wild-type plant EPSPS nucleotide sequence can provide such resistance when expressed in a plant cell. As described in the '587 patent, when comparing an EPSPS polypeptide to the wild-type polypeptide, modification to substitute isoleucine for threonine at residue 102 and substitute serine for proline at position 106 of the protein, the result is the double mutant EPSPS polypeptide (2mEPSPS) used in the subject insert. When expressed in a plant cell, it provides tolerance to glyphosate. The subject EPSPS gene, also referred to as the "2mepsps gene" or DMMG, was optimized to improve expression in both dicotyledonous plants as well as monocotyledonous plants, and in particular in soybean. Codon usage was selected based upon preferred hemicot codon usage, i.e. redesigned such that the protein is encoded by codons having a bias toward both monocot and dicot plant usage. Deleterious sequences and superfluous restriction sites can be removed to increase the efficiency of transcription/translation of the 2mepsps coding sequence and to facilitate DNA manipulation steps. The subject hemicot-optimized version of the monocot gene is further detailed in U.S. Ser. No. 13/303,502 (filed Nov. 23, 2011, claiming priority to Dec. 3, 2010) entitled, "OPTIMIZED EXPRESSION OF GLYPHOSATE RESISTANCE ENCODING NUCLEIC ACID MOLECULES IN PLANT CELLS."

As previously referenced herein, the introduction and integration of a transgene into a plant genome involves some random events (hence the name "event" for a given insertion that is expressed). That is, with many transformation techniques such as *Agrobacterium* transformation, the "gene gun," and WHISKERS, it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

During the process of introducing an insert into the genome of plant cells, it is not uncommon for some deletions or other alterations of the insert and/or genomic flanking sequences to occur. Thus, the relevant segment of the plasmid sequence provided herein might comprise some minor variations. The same is true for the flanking sequences provided herein. Thus, a plant comprising a polynucleotide having some range of identity with the subject flanking and/or insert sequences is within the scope of the subject invention. Identity to the sequence of the present invention can be a polynucleotide sequence having at least 65% sequence identity, more preferably at least 70% sequence identity, more preferably at least 75% sequence identity, more preferably at least 80% identity, and more preferably at least 85% 86%, 87%, 88%, 89%, 90%, 91%, 92%, 93%, 94%, 95%, 96%, 97%, 98%, 99% sequence identity with a sequence exemplified or described herein. Hybridization and hybridization conditions as provided herein can also be used to define such plants and polynculeotide sequences of the subject invention. The sequence which comprises the flanking sequences plus the full insert sequence can be confirmed with reference to the deposited seed.

As "events" are originally random events, as part of this disclosure at least 2500 seeds of a soybean line comprising Event pDAB8291.45.36.2 have been deposited and made available to the public without restriction (but subject to patent rights), with the American Type Culture Collection (ATCC), 10801 University Boulevard, Manassas, Va., 20110. The deposit has been designated as ATCC Deposit No. PTA-11335. 100 packets (25 seeds per packet) of *Glycine max* seeds ("Soybean Seed *Glycine max* L.: pDAB8291.45.36.2") were deposited on behalf of Dow AgroSciences LLC and M.S. Technologies, LLC on Sep. 14, 2010. The deposit was tested on Oct. 4, 2010, and on that date, the seeds were viable. This deposit was made and will be maintained in accordance with and under the terms of the Budapest Treaty with respect to seed deposits for the purposes of patent procedure. The deposit will be maintained without restriction at the ATCC depository, which is a public depository, for a period of 30 years, or five years after the most recent request, or for the effective life of the patent, whichever is longer, and will be replaced if it becomes nonviable during that period.

The deposited seeds are part of the subject invention. Clearly, soybean plants can be grown from these seeds, and such plants are part of the subject invention. The subject invention also relates to DNA sequences contained in these soybean plants that are useful for detecting these plants and progeny thereof. Detection methods and kits of the subject invention can be directed to identifying any one, two, or even all three of these events, depending on the ultimate purpose of the test.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR §1.822 is used.

As used herein, the term "progeny" denotes the offspring of any generation of a parent plant which comprises soybean Event pDAB8291.45.36.2.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" spans the point at which DNA inserted into the genome is linked to DNA from the soybean native genome flanking the insertion point, the identification or detection of one or the other junction sequences in a plant's genetic material being sufficient to be diagnostic for the event. Included are the DNA sequences that span the insertions in herein-described soybean events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

The subject invention relates in part to event identification using such flanking, junction, and insert sequences. Related PCR primers and amplicons are included in the invention. According to the subject invention, PCR analysis methods using amplicons that span across inserted DNA and its borders can be used to detect or identify commercialized transgenic soybean varieties or lines derived from the subject proprietary transgenic soybean lines.

The binary plasmid, pDAB8291 (SEQ ID NO:13) comprises the genetic elements depicted in FIG. 1. The following genetic elements (T-strand border sequences are not included) are contained within the T-strand region of pDAB8291. In Table 1, the residue numbering of the genetic elements is provided with respect to SEQ ID NO:13 disclosed herein.

TABLE 1

Residue Numbering of the Genetic Elements Comprising Binary Plasmid pDAB8291 (SEQ ID NO: 13).

| Genetic Element | Position | Reference |
|---|---|---|
| RB7 MARv3 (Matrix Attachment Region) | 137 bp-1302 bp | Thompson and Myatt, (1997) *Plant Mol. Biol.*, 34: 687-692.; WO9727207 |
| Intervening Sequence | 1303 bp-1341 bp | Not applicable |
| Histone H4A7 48 3'UTR (Untranslated Region) | 1342 bp-2002 bp | Chabouté et al., (1987) *Plant Mol. Biol.*, 8: 179-191 |
| Intervening Sequence containing stop codons in all 6-frames | 2003 bp-2037 bp | Not applicable |
| 2mEPSPS v2 | 2038 bp-3376 bp | concurrently filed application referenced above |
| OTPc (optimized transit peptide) | 3377 bp-3748 bp | U.S. Pat. No. 5,510,471 |
| Intervening Sequence | 3749 bp-3761 bp | Not applicable |
| Intron 2 | 3762 bp-4227 bp | Chaubet et al., (1992) *J. Mol. Biol.*, 225: 569-574 |
| Histone H4A7 48 Promoter | 4228 bp-5182 bp | Chabouté et al., (1987) *Plant Mol. Biol.*, 8: 179-191 |
| Intervening Sequence | 5183 bp-5274 bp | Not applicable |
| AtUbi 10 Promoter (*Arabidopsis thaliana* Ubiquitin 10 Promoter) | 5275 bp-6596 bp | Callis, et al., (1990) *J. Biol. Chem.*, 265: 12486-12493 |
| Intervening Sequence | 6597 bp-6604 bp | Not applicable |
| aad-12 v1 | 6605 bp-7483 bp | WO 2007/053482 |
| Intervening Sequence containing stop codons in all 6-frames | 7484 bp-7588 bp | Not applicable |
| AtuORF23 3' UTR (*Agrobacterium tumefaciens* Open Reading Frame 23 UTR) | 7589 bp-8045 bp | U.S. Pat. No. 5,428,147 |
| Intervening Sequence | 8046 bp-8159 bp | Not applicable |
| CsVMV Promoter (Cassava Vein Mosaic Virus Promoter) | 8160 bp-8676 bp | Verdaguer et al., (1996) *Plant Mol. Biol.*, 31: 1129-1139 |
| Intervening Sequence | 8677 bp-8683 bp | Not applicable |
| pat v6 | 8684 bp-9235 bp | Wohlleben et al., (1988) *Gene* 70: 25-37 |
| Intervening Sequence containing stop codons in all 6-frames | 9326 bp-9337 bp | Not applicable |
| AtuORF1 3'UTR (*Agrobacterium tumefaciens* Open Reading Frame 1 UTR) | 9338 bp-10,041 bp | Huang et al., (1990) *J. Bacteriol.* 172: 1814-1822 |

SEQ ID NOs: 14 and 15, respectively, are the 5' and 3' flanking sequences together with 5' and 3' portions of the insert sequence, as described in more detail below, and thus include the 5' and 3' "junction" or "transition" sequences of the insert and the genomic DNA. With respect to SEQ ID NO:14, residues 1-3088 are 5' genomic flanking sequence, and residues 3089-3406 are residues of the 5' end of the insert. With respect to SEQ ID NO:15, residues 1-223 are residues of the 3' end of the insert, and residues 224-1008 are 3' genomic flanking sequence. The junction sequence or transition with respect to the 5' end of the insert thus occurs at residues 3088-3089 of SEQ ID NO:14. The junction sequence or transition with respect to the 3' end of the insert thus occurs at residues 223-224 of SEQ ID NO:15. Polynucleotides of the subject invention include those comprising, for example, 5, 10, 20, 50, 100, 150, or 200 bases, or possibly more, and any increments therebetween, on either side of the junction sequence. Thus, a primer spanning the junction sequence could comprise, for example, 5-10 bases that would hybridize with flanking sequence and 5-10 bases that would hybridize with insert sequence. Probes and amplicons could be similarly designed, although they would often be longer than primers.

The subject sequences (including the flanking sequences) are unique. Based on these insert and flanking sequences, event-specific primers were generated. PCR analysis demonstrated that these soybean lines can be identified in different soybean genotypes by analysis of the PCR amplicons generated with these event-specific primer sets. Thus, these and other related procedures can be used to uniquely identify these soybean lines. The sequences identified herein are unique.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit soybean breeding programs as well as quality control, especially for commercialized transgenic soybean seeds. PCR detection kits for these transgenic soybean lines can also now be made and used. This can also benefit product registration and product stewardship.

Furthermore, flanking soybean/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of the subject disclosure, it should be clear that the subject invention includes seeds available under ATCC Deposit No. PTA-11335. The subject invention also includes a herbicide-tolerant soybean plant grown from a seed deposited with the ATCC under accession number PTA-11335. The subject invention further includes parts of said plant, such as leaves, tissue samples, seeds produced by said plant, pollen, and the like (wherein they comprise a transgenic insert flanked by SEQ ID NO:1 and SEQ ID NO:2).

Still further, the subject invention includes descendant and/or progeny plants of plants grown from the deposited seed, preferably a herbicide-resistant soybean plant wherein said plant has a genome comprising a detectable wild-type genomic DNA/insert DNA junction sequence as described herein. As used herein, the term "soybean" means *Glycine max* and includes all varieties thereof that can be bred with a soybean plant.

The invention further includes processes of making crosses using a plant of the subject invention as at least one parent. For example, the subject invention includes an $F_1$ hybrid plant having as one or both parents any of the plants exemplified herein. Also within the subject invention is seed produced by such $F_1$ hybrids of the subject invention. This invention includes a method for producing an $F_1$ hybrid seed by crossing an exemplified plant with a different (e.g. in-bred parent) plant and harvesting the resultant hybrid seed. The subject invention includes an exemplified plant that is either a female parent or a male parent. Characteristics of the resulting plants may be improved by careful consideration of the parent plants.

A herbicide-tolerant soybean plant of the subject invention can be bred by first sexually crossing a first parental soybean plant consisting of a soybean plant grown from seed of any one of the lines referred to herein, and a second parental soybean plant, thereby producing a plurality of first progeny plants; then selecting a first progeny plant that is resistant to a herbicide (or that possesses at least one of the events of the subject invention); selfing the first progeny plant, thereby producing a plurality of second progeny plants; and then selecting from the second progeny plants a plant that is resistant to a herbicide (or that possesses at least one of the events of the subject invention). These steps can further include the back-crossing of the first progeny plant or the second progeny plant to the second parental soybean plant or a third parental soybean plant. A soybean crop comprising soybean seeds of the subject invention, or progeny thereof, can then be planted.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The DNA molecules of the present invention can be used as molecular markers in a marker assisted breeding (MAB) method. DNA molecules of the present invention can be used in methods (such as, AFLP markers, RFLP markers, RAPD markers, SNPs, and SSRs) that identify genetically linked agronomically useful traits, as is known in the art. The herbicide-resistance trait can be tracked in the progeny of a cross with a soybean plant of the subject invention (or progeny thereof and any other soybean cultivar or variety) using the MAB methods. The DNA molecules are markers for this trait, and MAB methods that are well known in the art can be used to track the herbicide-resistance trait(s) in soybean plants where at least one soybean line of the subject invention, or progeny thereof, was a parent or ancestor. The methods of the present invention can be used to identify any soybean variety having the subject event.

Methods of the subject invention include a method of producing a herbicide-tolerant Soybean plant wherein said method comprises introgessing Event pDAB8291.45.36.2 into a soybean cultivar. More specifically, methods of the present invention can comprise crossing two plants of the subject invention, or one plant of the subject invention and any other plant. Preferred methods further comprise selecting progeny of said cross by analyzing said progeny for an event detectable according to the subject invention. For example, the subject invention can be used to track the subject event through breeding cycles with plants comprising other desirable traits, such as agronomic traits such as those tested herein in various Examples. Plants comprising the subject event and the desired trait can be detected, identified, selected, and quickly used in further rounds of breeding, for example. The subject event/trait can also be combined through breeding, and tracked according to the subject invention, with an insect resistant trait(s) and/or with further herbicide tolerance traits. One embodiment of the latter is a plant comprising the subject event combined with a gene encoding resistance to the herbicide dicamba.

Thus, the subject invention can be combined with, for example, additional traits encoding glyphosate resistance (e.g., resistant plant or bacterial glyphosate oxidase (GOX)), glyphosate acetyl transferase (GAT), additional traits for glufosinate resistance (e.g. bialaphos resistance (bar)), traits conferring acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance traits (e.g., Bxn), traits for resistance to dicamba herbicide (see, e.g., U.S. 2003/0135879), traits for resistance to inhibitors of HPPD (4-hydroxlphenyl-pyruvate-dioxygenase) enzyme, traits for resistance to inhibitors of phytoene desaturase (PDS), traits for resistance to photosystem II inhibiting herbicides (e.g., psbA), traits for resistance to photosystem I inhibiting herbicides, traits for resistance to protoporphyrinogen oxidase IX (PPO)-inhibiting herbicides (e.g., PPO-1), and traits for resistance to phenylurea herbicides (e.g., CYP76B1). One or more of such traits can be combined with the subject invention to provide the ability to effectively control, delay and/or prevent weed shifts and/or resistance to herbicides of multiple classes.

It will be appreciated by those of skill in the art that the aad-12 gene used in the subject invention also provides resistance to compounds that are converted to phenoxyacetate auxin herbicides (e.g., 2,4-DB, MCPB, etc.). The butyric acid moiety present in the 2,4-DB herbicide is converted through β-oxidation to the phytotoxic 2,4-dichlorophenoxyacetic acid. Likewise, MCPB is converted through β-oxidation to the phytotoxic MCPA. The butanoic acid herbicides are themselves nonherbicidal, but are converted to their respective acid from by β-oxidation within susceptible plants to produce the acetic acid form of the herbicide that is phytotoxic. Plants incapable of rapid β-oxidation are not harmed by the butanoic acid herbicides. However, plants that are capable of rapid β-oxidation and can convert the butanoic acid herbicide to the acetic form are subsequently protected by AAD-12.

Methods of applying herbicides are well known in the art. Such applications can include tank mixes of more than one herbicide. Preferred herbicides for use according to the subject invention are combinations of glyphosate, glufosinate, and a phenoxy auxin herbicide (such as 2,4-D; 2,4-DB; MCPA; MCPB). Other preferred combinations induce glyphosate plus 2,4-D or glufosinate plus 2,4-D mixtures. These three types of herbicides can be used in advantageous combinations that would be apparent to one skilled in the art having the benefit of the subject disclosure. One or more of the subject herbicides can be applied to a field/area prior to planting it with seeds of the subject invention. Such applications can be within 14 days, for example, of planting seeds of the subject invention. One or more of the subject herbicides can also be applied after planting prior to emergence. One or more of the subject herbicides can also be applied to the ground (for controlling weeds) or over the top of the weeds and/or over the top of transgenic plants of the subject invention. The subject three herbicides can be rotated or used in combination to, for example, control or prevent weeds that might to tolerant to one herbicide but not another. Various application times for the subject three types of herbicides can be used in various ways as would be known in the art.

Additionally, the subject event can be stacked with one or more additional herbicide tolerance traits, one or more additional input (e.g., insect resistance (e.g., the 812 Event or the 814 Event), fungal resistance, or stress tolerance, et al.) or output (e.g., increased yield, improved oil profile, improved fiber quality, et al.) traits, both transgenic and nontransgenic. Thus, the subject invention can be used to provide a complete agronomic package of improved crop quality with the ability to flexibly and cost effectively control any number of agronomic pests.

Methods to integrate a polynucleotide sequence within a specific chromosomal site of a plant cell via homologous recombination have been described within the art. For instance, site specific integration as described in U.S. Patent Application Publication No. 2009/0111188 A1, describes the use of recombinases or integrases to mediate the introduction of a donor polynucleotide sequence into a chromosomal target. In addition, International Patent Application No. WO 2008/021207, describes zinc finger mediated-homologous recombination to integrate one or more donor polynucleotide sequences within specific locations of the genome. The use of recombinases such as FLP/FRT as described in U.S. Pat. No. 6,720,475, or CRE/LOX as described in U.S. Pat. No. 5,658,772, can be utilized to integrate a polynucleotide sequence into a specific chromosomal site. Finally the use of meganucleases for targeting donor polynucleotides into a specific chromosomal location was described in Puchta et al., PNAS USA 93 (1996) pp. 5055-5060).

Other various methods for site specific integration within plant cells are generally known and applicable (Kumar et al., Trends in Plant Sci. 6(4) (2001) pp. 155-159). Furthermore, site-specific recombination systems which have been identified in several prokaryotic and lower eukaryotic organisms may be applied to use in plants. Examples of such systems include, but are not limited too; the R/RS recombinase system from the pSR1 plasmid of the yeast Zygosaccharomyces rouxii (Araki et al. (1985) J. Mol. Biol. 182: 191-203), and the Gin/gix system of phage Mu (Maeser and Kahlmann (1991) Mol. Gen. Genet. 230: 170-176).

In some embodiments of the present invention, it can be desirable to integrate or stack a new transgene(s) in proximity to an existing transgenic event. The transgenic event can be considered a preferred genomic locus which was selected based on unique characteristics such as single insertion site, normal Mendelian segregation and stable expression, and a superior combination of efficacy, including herbicide tolerance and agronomic performance in and across multiple environmental locations. The newly integrated transgenes should maintain the transgene expression characteristics of the existing transformants. Moreover, the development of assays for the detection and confirmation of the newly integrated event would be overcome as the genomic flanking sequences and chromosomal location of the newly integrated event are already identified. Finally, the integration of a new transgene into a specific chromosomal location which is linked to an existing transgene would expedite the introgression of the transgenes into other genetic backgrounds by sexual out-crossing using conventional breeding methods.

In some embodiments of the present invention, it can be desirable to excise polynucleotide sequences from a transgenic event. For instance transgene excision as described in U.S. patent application Ser. No. 13/011,666, describes the use of zinc finger nucleases to remove a polynucleotide sequence, consisting of a gene expression cassette, from a chromosomally integrated transgenic event. The polynucleotide sequence which is removed can be a selectable marker. Upon excision and removal of a polynucleotide sequence the modified transgenic event can be retargeted by the insertion of a polynucleotide sequence. The excision of a polynucleotide sequence and subsequent retargeting of the modified transgenic event provides advantages such as re-use of a selectable marker or the ability to overcome unintended changes to the plant transcriptome which results from the expression of specific genes.

The subject invention discloses herein a specific site on chromosome 03 in the soybean genome that is excellent for insertion of heterologous nucleic acids. Also disclosed is a 5' flanking sequence and a 3' flanking sequence, which can also be useful in identifying and/or targeting the location of the insertion/targeting site on chromosome 03. Thus, the subject invention provides methods to introduce heterologous nucleic acids of interest into this pre-established target site or in the vicinity of this target site. The subject invention also encompasses a soybean seed and/or a soybean plant comprising any heterologous nucleotide sequence inserted at the disclosed target site or in the general vicinity of such site. One option to accomplish such targeted integration is to excise and/or substitute a different insert in place of the pat expression cassette exemplified herein. In this general regard, targeted homologous recombination, for example and without limitation, can be used according to the subject invention.

As used herein gene, event or trait "stacking" is combining desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two or more different traits, including for example, two or more different insect traits, insect resistance trait(s) and disease resistance trait(s), two or more herbicide resistance traits, and/or insect resistance trait(s) and herbicide resistant trait(s). The use of a selectable marker in addition to a gene of interest can also be considered gene stacking.

"Homologous recombination" refers to a reaction between any pair of nucleotide sequences having corresponding sites containing a similar nucleotide sequence through which the two nucleotide sequences can interact (recombine) to form a new, recombinant DNA sequence. The sites of similar nucleotide sequence are each referred to herein as a "homology sequence." Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

The subject event enables transgenic expression of three different herbicide tolerance proteins resulting in tolerance to combinations of herbicides that would control nearly all broadleaf and grass weeds. This multi-herbicide tolerance trait expression cassette/transgenic insert can be stacked with other herbicide tolerance traits (e.g., glyphosate resistance, glufosinate resistance, imidazolinone resistance, dicamba resistance, HPPD resistance, bromoxynil resistance, et al.), and insect resistance traits (such as Cry1F, Cry1Ab, Cry1Ac, Cry 34/45, Cry1Be, Cry1Ca, Cry1Da, Cry1Ea, Cry1Fa, vegetative insecticidal proteins ("VIPS")—including VIP3A, and the like), for example. Additionally, the herbicide tolerance proteins in the expression cassette/transgenic insert of the subject invention can serve as one or more selectable marker sto aid in selection of primary transformants of plants genetically engineered with a second gene or group of genes.

These combinations of traits give rise to novel methods of controlling weeds (and like) species, due to the newly acquired resistance or inherent tolerance to herbicides (e.g., glyphosate). Thus, novel methods for controlling weeds using Event pDAB8291.45.36.2 are within the scope of the invention.

The use of the subject transgenic traits, stacked or transformed individually into crops, provides a tool for controlling other herbicide tolerant volunteer crops that do not contain genes for conferring tolerance to phenoxy, pyridyloxy, glyphosate and/or glufosinate herbicides.

A preferred plant, or a seed, of the subject invention comprises in its genome the insert sequences, as identified herein, together with at least 20-500 or more contiguous flanking nucleotides on both sides of the insert, as described herein. Unless indicated otherwise, reference to flanking sequences refers to those identified with respect to SEQ ID NO:1 and SEQ ID NO:2. Again, the subject events include heterologous DNA inserted between the subject flanking genomic sequences immediately adjacent to the inserted DNA. All or part of these flanking sequences could be expected to be transferred to progeny that receives the inserted DNA as a result of a sexual cross of a parental line that includes the event.

The subject invention includes tissue cultures of regenerable cells of a plant of the subject invention. Also included is a plant regenerated from such tissue culture, particularly where said plant is capable of expressing all the morphological and physiological properties of an exemplified variety. Preferred plants of the subject invention have all the physiological and morphological characteristics of a plant grown from the deposited seed. This invention further comprises progeny of such seed and seed possessing the quality traits of interest.

Manipulations (such as mutation, further transfection, and further breeding) of plants or seeds, or parts thereof, may lead to the creation of what may be termed "essentially derived" varieties. The International Union for the Protection of New Varieties of Plants (UPOV) has provided the following guideline for determining if a variety has been essentially derived from a protected variety:

[A] variety shall be deemed to be essentially derived from another variety ("the initial variety") when (i) it is predominantly derived from the initial variety, or from a variety that is itself predominantly derived from the initial variety, while retaining the expression of the essential characteristics that result from the genotype or combination of genotypes of the initial variety;

(ii) it is clearly distinguishable from the initial variety; and (iii) except for the differences which result from the act of derivation, it conforms to the initial variety in the expression of the essential characteristics that result from the genotype or combination of genotypes of the initial variety.

UPOV, Sixth Meeting with International Organizations, Geneva, Oct. 30, 1992; document prepared by the Office of the Union.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by seed weight, oil content, and total oil produced per acre, is within 15% of the average yield of an otherwise comparable commercial canola variety without the premium value traits grown in the same region.

"Agronomically elite" means that a line has desirable agronomic characteristics such as yield, maturity, disease resistance, and the like, in addition to the herbicide tolerance due to the subject event(s). Agronomic traits, taken individually or in any combination, as set forth in Examples, below, in a plant comprising an event of the subject invention, are within the scope of the subject invention. Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers directed to and/or comprising "junction sequences" or "transition sequences" (where the soybean genomic flanking sequence meets the insert sequence). For example, this includes a polynucleotide probes, primers, and/or amplicons designed to identify one or both junction sequences (where the insert meets the flanking sequence), the coordinates of which are discussed elsewhere herein. One common design is to have one primer that hybridizes in the flanking region, and one primer that hybridizes in the insert. Such primers are often each about at least 15 residues in length. With this arrangement, the primers can be used to generate/amplify a detectable amplicon that indicates the presence of an event of the subject invention. These primers can be used to generate an amplicon that spans (and includes) a junction sequence as indicated above.

The primer(s) "touching down" in the flanking sequence is typically not designed to hybridize beyond about 200 bases or so beyond the junction. Thus, typical flanking primers would be designed to comprise at least 15 residues of either strand within 200 bases into the flanking sequences from the beginning of the insert. That is, primers comprising a sequence of an appropriate size from (or hybridizing to) residues within 100 to 200-500 or so bases from either or both junction sequences identified above are within the scope of the subject invention. Insert primers can likewise be designed anywhere on the insert, but residues on the insert (including the complement) within 100 to 200-500 or so bases in from the junction sequence(s) identified above, can be used, for example, non-exclusively for such primer design.

One skilled in the art will also recognize that primers and probes can be designed to hybridize, under a range of standard hybridization and/or PCR conditions, to segments of sequences exemplified herein (or complements thereof), wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

It should be noted that errors in PCR amplification can occur which might result in minor sequencing errors, for example. That is, unless otherwise indicated, the sequences listed herein were determined by generating long amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the "insert" are illustrated in the Figures and are discussed in more detail below in the Examples. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a soybean plant. DNA sequences are provided that comprise the subject transgene/genomic insertion region junction sequence provided herein, segments comprising a junction sequence identified herein, and complements of any such exemplified sequences and any segments thereof. The insertion region junction sequence spans the junction between heterologous DNA inserted into the genome and the DNA from the soybean cell flanking the insertion site. Such sequences can be diagnostic for the given event.

Based on these insert and border sequences, event-specific primers can be generated. PCR analysis demonstrated that soybean lines of the subject invention can be identified in different soybean genotypes by analysis of the PCR amplicons generated with these event-specific primer sets. These and other related procedures can be used to uniquely identify these soybean lines. Thus, PCR amplicons derived from such primer pairs are unique and can be used to identify these soybean lines.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of soybean genomic sequence from one or more of the aforementioned soybean plants and/or sequences that are useful as primer sequences for the production of an amplicon product diagnostic for one or more of these soybean plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a transgene portion of a DNA sequence identified herein, or complements thereof, and a similar length of flanking soybean DNA sequence (such as SEQ ID NO:1 and SEQ ID NO:2 and segments thereof) from these sequences, or complements thereof. Such sequences are useful as DNA primers in DNA amplification methods. The amplicons produced using these primers are diagnostic for any of the soybean events referred to herein. Therefore, the invention also includes the amplicons produced by such DNA primers and homologous primers.

This invention also includes methods of detecting the presence of DNA, in a sample, that corresponds to the soybean event referred to herein. Such methods can comprise: (a) contacting the sample comprising DNA with a primer set that, when used in a nucleic acid amplification reaction with DNA from at least one of these soybean events, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to said event, wherein said method comprises: (a) contacting the sample comprising DNA with a probe that hybridizes under stringent hybridization conditions with DNA from at least one of said soybean events and which does not hybridize under the stringent hybridization conditions with a control soybean plant (non-event-of-interest DNA); (b) subjecting the sample and probe to stringent hybridization conditions; and (c) detecting hybridization of the probe to the DNA.

In still further embodiments, the subject invention includes methods of producing a soybean plant comprising Event pDAB8291.45.36.2, wherein said method comprises the steps of: (a) sexually crossing a first parental soybean line (comprising an expression cassettes of the present invention, which confers said herbicide resistance trait to plants of said line) and a second parental soybean line (that lacks this herbicide tolerance trait) thereby producing a plurality of progeny plants; and (b) selecting a progeny plant by the use of molecular markers. Such methods may optionally comprise the further step of back-crossing the progeny plant to the second parental soybean line to producing a true-breeding soybean plant that comprises said herbicide tolerance trait.

According to another aspect of the invention, methods of determining the zygosity of progeny of a cross with said event is provided. Said methods can comprise contacting a sample, comprising soybean DNA, with a primer set of the subject invention. Said primers, when used in a nucleic-acid amplification reaction with genomic DNA from at least one of said soybean events, produces a first amplicon that is diagnostic for at least one of said soybean events. Such methods further comprise performing a nucleic acid amplification reaction, thereby producing the first amplicon; detecting the first amplicon; and contacting the sample comprising soybean DNA with said primer set (said primer set, when used in a nucleic-acid amplification reaction with genomic DNA from soybean plants, produces a second amplicon comprising the native soybean genomic DNA homologous to the soybean genomic region; and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits can be developed using the compositions disclosed herein and methods well known in the art of DNA detection. The kits are useful for identification of the subject soybean event DNA in a sample and can be applied to methods for breeding soybean plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said soybean events, whether from a soybean plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence. An "isolated" polynucleotide connotes that the polynucleotide is in a non-natural state—operably linked to a heterologous promoter, for example. A "purified" protein likewise connotes that the protein is in a non-natural state.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., with regards to endpoint TaqMan and real-time PCR applications, one will select 1.5 mM to about 4.0 mM $MgCl2$ at temperature of about 60° C. to about 75° C. and may vary hold times, as described herein, for increasing stringency. For other hybridization techniques one will typically employ relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a marker nucleic acid molecule of the present invention has the nucleic acid sequence as set forth herein in one of the exemplified sequences, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Patent No. 4,683,195 and U.S. Pat. No. 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject soybean event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of the present invention. Following this method, an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the flanking/transgene insert sequence due to successful amplification and hybridization.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the soybean genome that is excellent for an insertion, the subject invention also includes a soybean seed and/or a soybean plant comprising at least one non-aad12/pat/2mepsps coding sequence in or around the general vicinity of this genomic location. One option is to substitute a different insert in place of the insert exemplified herein. In these general regards, targeted homologous recombination, for example, can be used according to the subject invention. This type of technology is the subject of, for example, WO 03/080809 A2 and the corresponding published U.S. application (U.S. 2003/0232410). Thus, the subject invention includes plants and plant cells comprising a heterologous insert (in place of or with multi-copies of the exemplified insert), flanked by all or a recognizable part of the flanking sequences identified herein as SEQ ID NO:1 and SEQ ID NO:2. An additional copy (or additional copies) of the exemplified insert or any of its components could also be targeted for insertion in this/these manner(s).

All patents, patent applications, provisional applications, and publications referred to or cited herein are incorporated by reference in their entirety to the extent they are not inconsistent with the explicit teachings of this specification.

The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

The following abbreviations are used unless otherwise indicated.

bp base pair
° C. degrees Celcius
DNA deoxyribonucleic acid
DIG digoxigenin
EDTA ethylenediaminetetraacetic acid
kb kilobase
μg microgram
μL microliter
mL milliliter
M molar mass
OLP overlapping probe
PCR polymerase chain reaction
PTU plant transcription unit
SDS sodium dodecyl sulfate
SOP standard operating procedure
SSC a buffer solution containing a mixture of sodium chloride and sodium citrate, pH 7.0
TBE a buffer solution containing a mixture of Tris base, boric acid and EDTA, pH 8.3
V volts

EXAMPLES

Example 1

Transformation and Selection of the 2mEPSPS and AAD-12 Soybean Event 8291.45.36.2

Transgenic soybean (*Glycine max*) containing the Soybean Event 8291.45.36.2 was generated through *Agrobacterium*-mediated transformation of soybean cotyledonary node explants. The disarmed *Agrobacterium* strain EHA101 (Hood et al., 2006) carrying the binary vector pDAB8291 (FIG. 1) containing the selectable marker, pat, and the genes of interest, aad-12 and 2mepsps v2, within the T-strand DNA region, was used to initiate transformation.

*Agrobacterium*-mediated transformation was carried out using a modified procedure of Zeng et al. (2004). Briefly, soybean seeds (cv Maverick) were germinated on basal media and cotyledonary nodes were isolated and infected with *Agrobacterium*. Shoot initiation, shoot elongation, and rooting media were supplemented with cefotaxime, timentin and vancomycin for removal of *Agrobacterium*. Glufosinate selection was employed to inhibit the growth of non-transformed shoots. Selected shoots were transferred to rooting medium for root development and then transferred to soil mix for acclimatization of plantlets.

Terminal leaflets of selected plantlets were leaf painted with glufosinate to screen for putative transformants. The screened plantlets were transferred to the greenhouse, allowed to acclimate and then leaf-painted with glufosinate to reconfirm tolerance and deemed to be putative transformants. The screened plants were sampled and molecular analyses for the confirmation of the selectable marker gene and/or the gene of interest were carried out. $T_0$ plants were allowed to self fertilize in the greenhouse to give rise to $T_1$ seed.

This event, Soybean Event 8291.45.36.2, was generated from an independent transformed isolate. The $T_1$ plants were backcrossed and introgressed into elite varieties over subsequent generations. The event was selected based on its unique characteristics such as single insertion site, normal Mendelian segregation and stable expression, and a superior combination of efficacy, including herbicide tolerance and agronomic performance. The following examples contain the data which were used to characterize Soybean Event 8291.45.36.2.

Example 2

Characterization of AAD-12, 2mEPSPS and PAT Protein in Soybean Event 8291.45.36.2

The biochemical properties of the recombinant AAD-12, 2mEPSPS and PAT protein derived from the transgenic soybean event pDAB8291.45.36.2 were characterized. Quantitative enzyme-linked immunosorbent assay (ELISA) was used to characterize the biochemical properties of the protein and confirm expression of AAD-12, PAT and 2mEPSPS protein.

Example 2.1

Expression of the AAD-12 Protein in Plant Tissues

Levels of AAD-12 protein were determined in soybean event pDAB8291.45.36.2. The soluble, extractable AAD-12 protein was measured using a quantitative enzyme-linked immunosorbent assay (ELISA) method from soybean leaf tissue.

Samples of soybean tissues were isolated from the test plants and prepared for expression analysis. The AAD-12 protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using an AAD-12 ELISA kit in a sandwich format. The kit was used following the manufacturer's suggested protocol.

Detection analysis was performed to investigate the expression stability and heritability both vertically (between generations) and horizontally (between lineages of the same generation) in soybean event pDAB8291.45.36.2. At the T4 generation soybean event pDAB8291.45.36.2 expression was stable (not segregating) and consistent across all lineages. Field expression level studies were performed on soybean event pDAB8291.45.36.2; average expression across all lineages was approximately 200-250 ng/cm$^2$.

Example 2.2

Expression of the 2mEPSPS Protein in Plant Tissues

Levels of 2mEPSPS protein were determined in soybean event pDAB8291.45.36.2. The soluble, extractable 2mEPSPS protein was measured using a quantitative enzyme-linked immunosorbent assay (ELISA) method from soybean leaf tissue.

Samples of soybean tissues were isolated from the test plants and prepared for expression analysis. The 2mEPSPS protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using a 2mEPSPS ELISA kit in a sandwich format. The kit was used following the manufacturer's suggested protocol.

Detection analysis was performed to investigate the expression stability and heritability both vertically (between generations) and horizontally (between lineages of the same generation) in soybean event pDAB8291.45.36.2. At the T4 generation soybean event pDAB8291.45.36.2 expression was stable (not segregating) and consistent across all lineages. Field expression level studies were performed on soybean event pDAB8291.45.36.2. Average expression across all lineages was approximately 5,000-10,000 ng/cm$^2$.

Example 2.3

Expression of the PAT Protein in Plant Tissues

Levels of PAT protein were determined in soybean event pDAB8291.45.36.2. The soluble, extractable PAT protein was measured using a quantitative enzyme-linked immunosorbent assay (ELISA) method from soybean leaf tissue.

Samples of soybean tissues were isolated from the test plants and prepared for expression analysis. The PAT protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using a PAT ELISA kit in a sandwich format. The kit was used following the manufacturer's suggested protocol.

Detection analysis was performed to investigate the expression stability and heritability both vertically (between generations) and horizontally (between lineages of the same generation) in soybean event pDAB8291.45.36.2. At the T4 generation soybean event pDAB8291.45.36.2 expression was stable (not segregating) and consistent across all lineages. Field expression level studies were performed on soybean event pDAB8291.45.36.2. Average expression across all lineages was approximately 15-20 ng/cm$^2$.

Example 3

Cloning and Characterization of DNA Sequence in the Insert and the Flanking Border Regions of Soybean Event pDAB8291.45.36.2

To characterize and describe the genomic insertion site, the sequence of the flanking genomic DNA border regions of soybean event pDAB8291.45.36.2 were determined. In total, 4,414 bp of soybean event pDAB8291.45.36.2 genomic sequence was confirmed, comprising 3,088 bp of 5' flanking border sequence (SEQ ID NO:1), 785 bp of 3' flanking border sequence (SEQ ID NO:2). PCR amplification based on the soybean Event pDAB8291.45.36.2 border sequences validated that the border regions were of soybean origin and that the junction regions are unique sequences for event pDAB8291.45.36.2. The junction regions could be used for event-specific identification of soybean event pDAB8291.45.36.2. The T-strand insertion site was characterized by cloning a genomic fragment corresponding to the region of the identified flanking border sequences from the genome of non-transgenic soybean. Comparison of soybean event pDAB8291.45.36.2 with the wild type genomic sequence revealed a 48 bp deletion from the original locus.

Overall, the characterization of the insert and border sequence of soybean event pDAB8291.45.36.2 indicated that an intact copy of the T-strand was present in the soybean genome.

TABLE 2

Primers and sequences used to analyze DNA in Soybean Event pDAB8291.45.36.2

| SEQ ID NO: | Primer Name | Size (bp) | Sequence (5' to 3') | Purpose |
|---|---|---|---|---|
| SEQ ID NO: 3 | 4536_WF1 | 27 | CGGTTTATGGGTGAACAATCTCACATA | confirmation of 5' border genomic DNA, used with ED_v2_C1 |
| SEQ ID NO: 4 | 4536_WF2 | 26 | GGGTGAACAATCTCACATATCAGTCG | confirmation of 5' border genomic DNA, used with ED_v2_C1 |
| SEQ ID NO: 5 | 4536_WF3 | 28 | TTTAAATGTGGGTCCATGTGTCTTACAA | confirmation of 5' border genomic DNA, used with ED_v2_C1 |
| SEQ ID NO: 6 | 4536_WF4 | 28 | AATTTAGCCAAGGAGGGGACTACCATAC | confirmation of 5' border genomic DNA, used with ED_v2_C1 |
| SEQ ID NO: 7 | 4536_WR1 | 28 | GCAGGCATATTTCCAGGAGATAAAGACT | confirmation of 3' border genomic DNA, used with PAT_11 |
| SEQ ID NO: 8 | 4536_WR2 | 28 | ATAAAGACTGTGCCCAAATTGACGA | confirmation of 3' border genomic DNA, used with PAT_11 |
| SEQ ID NO: 9 | 4536_WR3 | 25 | CGTCCAAAGCATTTATGGTTCAGTTATT | confirmation of 3' border genomic DNA, used with PAT_11 |
| SEQ ID NO: 10 | 4536_WR4 | 28 | GGACACATTTGGTAAGGAGGCTACA | confirmation of 3' border genomic DNA, used with PAT_11 |
| SEQ ID NO: 11 | ED_v2_C1 | 25 | AGTTTGCTGAGGTGCTTGAGATGAT | confirmation of 5' border genomic DNA, used with 4536_WF1, 4536_WF2, 4536_WF3, or 4536_WF4, |
| SEQ ID NO: 12 | PAT_11 | 24 | ACAGAGCCACAAACACCACAAGAG | confirmation of 3' border genomic DNA, used with 4536_WR1, 4536_WR2, 4536_WR3, or 4536_WR4, |

TABLE 3

PCR conditions for amplification of border regions and event-specific sequences in soybean event pDAB8291.45.36.2

| Target Sequence | Primer Set | PCR Mixture | Pre-denature (° C./min) | Denature (° C./sec.) | Anneal (° C./sec.) | Extension (° C./min:sec) | Final Extension (° C./min) |
|---|---|---|---|---|---|---|---|
| 5' border | 4536_WF1/ED_v2_C1 | D | 95/3 | 98/10 | 66/30 32 cycles | 68/4:00 | 72/10 |
| 5' border | 4536_WF3/ED_v2_C1 | D | 95/3 | 98/10 | 66/30 32 cycles | 68/4:00 | 72/10 |
| 3' border | 4536_WR1/PAT_11 | D | 95/3 | 98/10 | 66/30 32 cycles | 68/4:00 | 72/10 |
| 3' border | 4536_WR3/PAT_11 | D | 95/3 | 98/10 | 66/30 35 cycles | 68/4:00 | 72/10 |
| Across the insert locus | 4536_WF1/4536_WR1 | D | 95/3 | 98/10 | 66/30 32 cycles | 68/4:00 | 72/10 |

TABLE 3-continued

PCR conditions for amplification of border regions and event-specific sequences in soybean event pDAB8291.45.36.2

| Target Sequence | Primer Set | PCR Mixture | Pre-denature (° C./min) | Denature (° C./sec.) | Anneal (° C./sec.) | Extension (° C./min:sec) | Final Extension (° C./min) |
|---|---|---|---|---|---|---|---|
| Across the insert locus | 4536_WF4/4536_WR4 | D | 95/3 | 98/10 | 66/30 32 cycles | 68/4:00 | 72/10 |

TABLE 4

PCR mixture for amplification of border regions and event specific sequences in soybean event pDAB8291.45.36.2.

| PCR Mixture A | | PCR Mixture B | |
|---|---|---|---|
| Reagent | 1 x reaction (µL) | Reagent | 1 x reaction (µL) |
| H20 | 0.8 | H20 | 14.6 |
| AccPrime pfx SuperMix | 20 | 10X LA Taq buffer | 2 |
| — | — | MgCl2 (25 mM) | 0.6 |
| — | — | dNTP (2.5 uM) | 1.6 |
| 10 uM primer | 0.2 | 10 uM primer | 0.1 |
| gDNA digestion | 1 | gDNA digestion | 1 |
| — | — | LA Taq (5 U/ul) | 0.1 |
| rxn vol: | 22 | rxn vol: | 20 |

| PCR Mixture C | | PCR Mixture D | |
|---|---|---|---|
| Reagent | 1 x reaction (µL) | Reagent | 1 x reaction (µL) |
| H20 | 28 | H20 | 11.6 |
| 10X PCR buffer II (Mg-plus) | 5 | 10X PCR buffer II (Mg-plus) | 2 |
| MgCl$_2$[25 mM] | 1.5 | MgCl$_2$[25 mM] | 0.6 |
| dNTP[2.5 mM] | 8 | dNTP[2.5 mM] | 3.2 |
| Adaptor PCR primer (10 µM) | 1 | primer1 (10 µM) | 0.4 |
| GOI nested primer (10 µM) | 1 | primer2 (10 µM) | 0.4 |
| DNA binded Beads | 5 | DNA Template | 0.2 |
| LA Taq (5 U/ul) | 0.5 | LA Taq (5 U/ul) | 1.6 |
| rxn vol: | 50 | rxn vol: | 20 |

Example 3.1

Confirmation of Soybean Genomic Sequences

The 5' and 3' flanking borders were aligned to *Glycine max* whole genome shotgun sequence chromosome 03, indicating that the transgene of soybean event pDAB8291.45.36.2 was probably inserted in soybean genome chromosome 03. To confirm the insertion site of soybean event pDAB8291.45.36.2 transgene in the soybean genome, PCR was carried out with different pairs of primers (FIG. 2 and Table 3). Genomic DNA from soybean event pDAB8291.45.36.2 and other transgenic or non-transgenic soybean lines was used as templates. Thus, to confirm if the obtained 5' end border sequences are correct, 2mepsps specific primers, for example ED_v2_C1 (SEQ ID NO:11), and two primers designed according to the cloned 5' end border sequence, designated 4536_WF1 (SEQ ID NO:3) and 4536_WF4 (SEQ ID NO:6), were used for amplifying the DNA segment that spans the 2mepsps gene to 5' end border sequence. Similarly, for confirmation of the 3' end border sequence, a pat specific primer, for example PAT_11 (SEQ ID NO:12), and two primers designed according to the cloned 3' end border sequence and/or its alignment sequence on soybean genome chromosome 03, designated 4536_WR1 (SEQ ID NO:7) and 4536_WR4 (SEQ ID NO:10), were used for amplifying DNA segments that span the pat gene to 3' end border sequence. DNA fragments with predicted sizes were amplified only from the genomic DNA of soybean event pDAB8291.45.36.2 with each primer pair, one primer located on the flanking border of soybean event pDAB8291.45.36.2 and one transgene specific primer, but not from DNA samples from other transgenic soybean lines or non-transgenic control. The results indicate that the cloned 5' and 3' border sequences are the flanking border sequences of the T-strand insert in soybean event pDAB8291.45.36.2.

To further confirm the DNA insertion in the soybean genome, a PCR amplification spanning the two soybean border sequences was completed. Two primers, 4536_WF1 (SEQ ID NO:3) and 4536_WF4 (SEQ ID NO:6), were designed according to the 5' end border sequence and two primers, 4536-WR1 (SEQ ID NO:7) and 4536-WR4 (SEQ ID NO:10), were designed according to the 3' end border sequence. As expected, PCR amplification with the primer pair of 4536_WF1 (SEQ ID NO;3) and 4536_WR1 (SEQ ID NO:7) amplified an approximately 3.0 kb DNA fragment from the non-transgenic soybean controls and other soybean transgenic lines but not from the sample of soybean event pDAB8291.45.36.2. Similarly, PCR reactions completed with the primer pair of 4536_WF4 (SEQ ID NO:6) and 4536_WR4 (SEQ ID NO:10) produced an approximately 878 bp DNA fragment from genomic DNA of the non-transgenic soybean controls and other soybean transgenic lines except the sample of soybean event pDAB8291.45.36.2. These results demonstrated that the transgene of soybean event pDAB8291.45.36.2 was inserted into the site of soybean genome chromosome 03.

Example 3.2

Confirmation of Soybean Genomic Sequences

The 3 kb amplified DNA fragments, using the primer pair of 4536_WF1 and 4536_WR1, from non-transgenic soybean line Maverick were cloned and sequenced. The sequence was aligned with the identified 5' and 3' border sequences from soybean event pDAB8291.45.36.2. This demonstrated that the cloned DNA sequence contained the locus where the T-strand of pDAB8291 was integrated into soybean event pDAB8291.45.36.2. Alignment analysis also revealed a 48 bp deletion from the original locus (FIG. 3). Open reading frame (ORF) analysis using Vector NTI (Version 11, Invitrogen) revealed the T-strand in soybean event pDAB8291.45.36.2 was inserted into an ORF of 249 bp located in the soybean genomic region of the original locus that was cloned.

Example 4

Soybean Event pDAB8291.45.36.2 Characterization Via Southern Blot

Southern blot analysis was used to establish the integration pattern of soybean event pDAB8291.45.36.2. These experiments generated data which demonstrated the integration and integrity of the aad-12, pat, and 2mepsps v2 transgenes within the soybean genome. Soybean event pDAB8291.45.36.2 was characterized as a full length, simple integration event containing a single copy of the aad-12, pat and 2mepsps v2 PTU from plasmid pDAB8291.

Southern blot data suggested that a T-strand fragment inserted into the genome of soybean event pDAB8291.45.36.2. Detailed Southern blot analysis was conducted using a probe specific to the aad-12, pat and 2mepsps v2 insert, contained in the T-strand integration region of pDAB8291, and descriptive restriction enzymes that have cleavage sites located within the plasmid and produce hybridizing fragments internal to the plasmid or fragments that span the junction of the plasmid with soybean genomic DNA (border fragments). The molecular weights indicated from the Southern hybridization for the combination of the restriction enzyme and the probe were unique for the event, and established its identification patterns. These analyses also showed that the plasmid fragment had been inserted into soybean genomic DNA without rearrangements of the aad-12, pat and 2mepsps v2 PTU.

Example 4.1

Soybean Leaf Sample Collection and Genomic DNA (gDNA) Isolation

Genomic DNA was extracted from leaf tissue harvested from individual soybean plants containing soybean event pDAB8291.45.36.2. In addition, gDNA was isolated from a conventional soybean plant, Maverick, which contains the genetic background that is representative of the substance line, absent the aad-12 and 2mepsps v2 genes. Individual genomic DNA was extracted from lyophilized leaf tissue following the standard cetytrimethylammonium bromide CTAB method. Following extraction, the DNA was quantified spectrofluorometrically using Pico Green reagent (Invitrogen, Carlsbad, Calif.). The DNA was then visualized on an agarose gel to confirm values from the Pico Green analysis and to determine the DNA quality.

Example 4.2

DNA Digestion and Separation

For Southern blot molecular characterization of soybean event pDAB8291.45.36.2, ten micrograms (10 µg) of genomic DNA was digested. Genomic DNA from the soybean pDAB8291.45.36.2 and non-transgenic soybean line Maverick was digested by adding approximately five units of selected restriction enzyme per µg of DNA and the corresponding reaction buffer to each DNA sample. Each sample was incubated at approximately 37° C. overnight. The restriction enzymes BstZ17I, HinDIII, NcoI, NsiI, and PacI were used individually for the digests (New England Biolabs, Ipswich, Mass.). In addition, a positive hybridization control sample was prepared by combining plasmid DNA, pDAB8291 with genomic DNA from the non-transgenic soybean variety, Maverick. The plasmid DNA/genomic DNA cocktail was digested using the same procedures and restriction enzyme as the test samples. After the digestions were incubated overnight, NaCl was added to a final concentration of 0.1M and the digested DNA samples were precipitated with isopropanol. The precipitated DNA pellet was resuspended in 20 µl of 1× loading buffer (0.01% bromophenol blue, 10.0 mM EDTA, 5.0% glycerol, 1.0 mM Tris pH 7.5). The DNA samples and molecular size markers were then electrophoresed through 0.85% agarose gels with 0.4×TAE buffer (Fisher Scientific, Pittsburgh, Pa.) at 35 volts for approximately 18-22 hours to achieve fragment separation. The gels were stained with ethidium bromide (Invitrogen, Carlsbad, Calif.) and the DNA was visualized under ultraviolet (UV) light

Example 4.3

Southern Transfer and Membrane Treatment

Southern blot analysis was performed essentially as described by, Memelink, J.; Swords, K.; Harry J.; Hoge, C.; (1994) Southern, Northern, and Western Blot Analysis. Plant Mol. Biol. Manual F1:1-23. Briefly, following electrophoretic separation and visualization of the DNA fragments, the gels were depurinated with 0.25M HCl for approximately 20 minutes, and then exposed to a denaturing solution (0.4 M NaOH, 1.5 M NaCl) for approximately 30 minutes followed by neutralizing solution (1.5 M NaCl, 0.5 M Tris pH 7.5) for at least 30 minutes. Southern transfer was performed overnight onto nylon membranes using a wicking system with 10×SSC. After transfer the DNA was bound to the membrane by UV crosslinking following by briefly washing membrane with a 2×SSC solution. This process produced Southern blot membranes ready for hybridization.

Example 4.4

DNA Probe Labeling and Hybridization

The DNA fragments bound to the nylon membrane were detected using a labeled probe. Probes were generated by a PCR-based incorporation of a digoxigenin (DIG) labeled nucleotide, [DIG-11]-dUTP, into the DNA fragment amplified from plasmid pDAB8291 using primers specific to gene elements. Generation of DNA probes by PCR synthesis was carried out using a PCR DIG Probe Synthesis Kit (Roche Diagnostics, Indianapolis, Ind.) following the manufacturer's recommended procedures.

Labeled probes were analyzed by agarose gel electrophoresis to determine their quality and quantity. A desired amount of labeled probe was then used for hybridization to the target DNA on the nylon membranes for detection of the specific fragments using the procedures essentially as described for DIG Easy Hyb Solution (Roche Diagnostics, Indianapolis, Ind.). Briefly, nylon membrane blots containing fixed DNA were briefly washed with 2×SSC and pre-hybridized with 20-25 mL of pre-warmed DIG Easy Hyb solution in hybridization bottles at approximately 45-55° C. for about 2 hours in a hybridization oven. The pre-hybridization solution was then decanted and replaced with approximately 15 mL of pre-warmed DIG Easy Hyb solution containing a desired amount of specific probes denatured by boiling in a water bath for approximately five minutes. The hybridization step was then conducted at approximately 45-55° C. overnight in the hybridization oven.

At the end of the probe hybridization, DIG Easy Hyb solutions containing the probes were decanted into clean tubes and stored at approximately −20° C. These probes could be reused for twice according to the manufacturer's recommended procedure. The membrane blots were rinsed briefly and washed twice in clean plastic containers with low stringency wash buffer (2×SSC, 0.1% SDS) for approximately five minutes at room temperature, followed by washing twice with high stringency wash buffer (0.1×SSC, 0.1% SDS) for 15 minutes each at approximately 65° C. The membrane blots briefly washed with 1× Maleic acid buffer from the DIG Wash and Block Buffer Set (Roche Diagnostics, Indianapolis, Ind.) for approximately 5 minutes. This was followed by blocking in a 1× blocking buffer for 2 hours and an incubation with anti-DIG-AP (alkaline phosphatase) antibody (Roche Diagnostics, Indianapolis, Ind.) in 1× blocking buffer also for a minimum of 30 minutes. After 2-3 washes with 1× washing buffer, specific DNA probes remain bound to the membrane blots and DIG-labeled DNA standards were visualized using CDP-Star Chemiluminescent Nucleic Acid Detection System (Roche Diagnostics, Indianapolis, Ind.) following the manufacturer's recommendation. Blots were exposed to chemiluminescent film for one or more time points to detect hybridizing fragments and to visualize molecular size standards. Films were developed with an All-Pro 100 Plus film developer (Konica Minolta, Osaka, Japan) and images were scanned. The number and sizes of detected bands were documented for each probe (Table 5). DIG-labeled DNA Molecular Weight Marker II (DIG MWM II) and DIG-labeled DNA Molecular Weight Marker VII (DIG MWM VII), visible after DIG detection as described, were used to determine hybridizing fragment size on the Southern blots.

TABLE 5

Length of probes used in southern analysis of soybean event pDAB8291.45.36.2

| Probe Name | Genetic Element | Length (bp) |
|---|---|---|
| 2mEPSPS | 2mEPSPS v2 | 1162 |
| aad-12 | aad-12 | 671 |
| specR | Spectinomycin resistance gene | 750 |
| OriRep | Ori Rep | 852 |
| trfA | Replication initiation protein trfA | 1119 |

Example 4.5

Southern Blot Results

Expected and observed fragment sizes with a particular digest and probe, based on the known restriction enzyme sites of the aad-12 and 2mepsps PTU, are given in Table 6. Expected fragment sizes are based on the plasmid map of pDAB8291 and observed fragment sizes are approximate results from these analyses and are based on the indicated sizes of the DIG-labeled DNA Molecular Weight Marker II and Mark VII fragments.

Two types of fragments were identified from these digests and hybridizations: internal fragments where known enzyme sites flank the probe region and are completely contained within the insertion region of the aad-12 and 2mepsps PTU, and border fragments where a known enzyme site is located at one end of the probe region and a second site is expected in the soybean genome. Border fragment sizes vary by event because, in most cases, DNA fragment integration sites are unique for each event. The border fragments provide a means to locate a restriction enzyme site relative to the integrated DNA and to evaluate the number of DNA insertions. Southern blot analyses completed on multiple generations of soybean containing event pDAB8291.45.36.2 produced data which suggested that a low copy, intact aad-12 and 2mepsps PTU from plasmid pDAB8291 was inserted into the soybean genome of soybean event pDAB8291.45.36.2.

TABLE 6

Predicted and Observed Hybridizing Fragments in Southern Blot Analysis

| DNA Probe | Restriction Enzymes | Samples | Expected Fragment Sizes (bp)[1] | Observed Fragment Size (bp)[2] |
|---|---|---|---|---|
| aad-12 | BstZ17I | pDAB8291 | 4994 | ~5000 |
|  |  | Maverick | none | none |
|  |  | Soybean Event pDAB8291.45.36.2 | 4994 | ~5000 |
|  | Hind III | pDAB8291 | 4731 | ~4800 |
|  |  | Maverick | none | none |
|  |  | Soybean Event pDAB8291.45.36.2 | >4078 | ~4800 |
|  | Nco I | pDAB8291 | 7429 | ~7500 |
|  |  | Maverick | none | none |
|  |  | Soybean Event pDAB8291.45.36.2 | >3690 | ~5900 |
|  | Nsi I | pDAB8291 | 4974 | ~5000 |
|  |  | Maverick | none | none |
|  |  | Soybean Event pDAB8291.45.36.2 | 4974 | ~5000 |
|  | Pac I | pDAB8291 | 6780 | ~6800 |
|  |  | Maverick | none | none |
|  |  | Soybean Event pDAB8291.45.36.2 | 6780 | ~6800 |
| EPDM | BstZ17I | pDAB8291 | 11036 | ~11000 |
|  |  | Maverick | none | none |
|  |  | Soybean Event pDAB8291.45.36.2 | >4870 | ~11000 |
|  | Nco I | pDAB8291 | 5215 | ~5200 |
|  |  | Maverick | none | none |
|  |  | Soybean Event pDAB8291.45.36.2 | >3772 | ~4000 |
|  | Nsi I | pDAB8291 | 11056 | ~11000 |
|  |  | Maverick | none | none |
|  |  | Soybean Event pDAB8291.45.36.2 | >5207 | ~6000 |
|  | Pac I | pDAB8291 | 6780 | ~6800 |
|  |  | Maverick | none | none |
|  |  | Soybean Event pDAB8291.45.36.2 | 6780 | ~6800 |
| specR | Hind III | pDAB8291 | 9334 | ~9300 |
|  |  | Maverick | none | none |
|  |  | Soybean Event pDAB8291.45.36.2 | none | none |
| OriRep + trfA | Pac I | pDAB8291 | 9210 | ~9210 |
|  |  | Maverick | none | none |
|  |  | Soybean Event pDAB8291.45.36.2 | none | none |

The restriction enzymes NcoI and HinD III bind and cleave unique restriction sites in plasmid pDAB8291. Subsequently, these enzymes were selected to characterize the aad-12 gene insert in soybean event pDAB8291.45.36.2 Border fragments of greater than 4,078 bp or greater than 3,690 bp were predicted to hybridize with the probe following HinD III and NcoI digestion respectively (Table 6). Single aad-12 hybridization bands of approximately 4,800 bp and approximately 5,900 bp were observed when HinDIII and NcoI were used, respectively. The hybridization of the probe to bands of this size suggests the presence of a single site of insertion for the aad-12 gene in the soybean genome of soybean event pDAB8291.45.36.2. Restriction enzymes BstZ17I, NsiI and PacI was selected to release a fragment which contains the aad-12 plant transcription unit (PTU; promoter/gene/terminator) (Table 6). The predicted approximately 5,000, approximately 5,000, and approximately 6,800 bp fragments were observed with the probe following BstZ17I, NsiI and PacI digestions, respectively. Results obtained with the enzyme digestion of the pDAB8291.45.36.2 sample followed by probe hybridization indicated that an intact aad-12 PTU from plasmid pDAB8291 was inserted into the soybean genome of soybean event pDAB8291.45.36.2. In addition, the molecular weight sizes of the hybridization bands produced for the HinDIII, NcoI, NsiI, and BstZ17I restriction fragments indicate that the aad-12 PTU also contained the linked pat PTU.

The restriction enzymes BstZ17I, NcoI and NsiI bind and cleave restriction sites in plasmid pDAB8291. Subsequently, these enzymes were selected to characterize the 2mepsps gene insert in soybean event pDAB8291.45.36.2 Border fragments of greater than 4,870 bp. greater than 3,772, or greater than 5,207 bp were predicted to hybridize with the probe following the BstZ17I, NcoI and NsiI digests, respectively (Table 6). Single 2mepsps hybridization bands of approximately 11,000 bp, approximately 4,000 bp and approximately 6,000 bp were observed when BstZ17I, NcoI and NsiI were used, respectively. The hybridization of the probe to bands of this size suggests the presence of a single site of insertion for the 2mepsps gene in the soybean genome of soybean event pDAB8291.45.36.2. Restriction enzyme PacI was selected to release a fragment which contains the 2mepsps plant transcription unit (PTU; promoter/gene/terminator) (Table 6). The predicted approximately 6,800 bp fragments was observed with the probe following the PacI digestions. Results obtained with the enzyme digestion of the pDAB8291.45.36.2 sample followed by probe hybridization indicated that an intact 2mepsps PTU from plasmid pDAB8291 was inserted into the soybean genome of soybean event pDAB8291.45.36.2.

Example 4.6

Absence of Backbone Sequences

Southern blot analysis was also conducted to verify the absence of the spectinomycin resistance gene, Ori Rep element and replication initiation protein trfA (trfA element) in soybean event pDAB8291.45.36.2. No specific hybridization to spectinomycin resistance, Ori Rep element or trfA element is expected when appropriate positive (pDAB8291 plus Maverick) and negative (Maverick) controls are included for Southern analysis. Following Hind III digestion and hybridization with specR specific probe, one expected size band of approximately 9,300 bp was observed in the positive control sample (pDAB8291 plus maverick) but absent from samples of the negative control and soybean event pDAB8291.45.36.2. Similarly, one expected size band of approximately 9,200 bp was detected in the positive control sample (pDAB8291 plus maverick) but absent from the samples of the negative control and soybean event pDAB8291.45.36.2 after Pac I digestion and hybridization with mixture of OriRep specific probe and trfA specific probe. These data indicate the absence of spectinomycin resistance gene, Ori Rep element and replication initiation protein trfA in soybean event pDAB8291.45.36.2.

Example 5

Argronomic, Yield and Herbicide Tolerance Evaluation

The agronomic characteristics and herbicide tolerance of soybean Event pDAB8291.45.36.2 were studied in yield trials at multiple geographical locales during a single growing season. No agronomically meaningful unintended differences were observed between soybean Event pDAB8291.45.36.2 and the Maverick control plants. The results of the study demonstrated that soybean Event pDAB8291.45.36.2 was agronomically equivalent to the Maverick control plants. In addition, soybean Event pDAB8291.45.36.2 provided robust herbicide tolerance when sprayed with a tankmix of glyphosate and 2,4-D.

The following agronomic characteristics were measured and recorded for all test entries at each location.

1.) Emergence: Calculated by dividing Stand count by number of seeds planted in a one meter section and multiplying by 100.
2.) Seedling Vigor at V1: Vigor is an overall estimate of the health of the plot. Results were rated on a scale of 0-100% with 0% representing a plot with all dead plants and 100% representing plots that look very healthy.
3.) Rated overall visual crop injury, chlorosis and necrosis at 1 day, 7 days, and 14 days after V3 chemical application. Observations were made for any signs of epinasty which is typical of 2,4-D injury. Epinasty is exhibited as twisting or drooping of leaves and stems. All crop injuries used a 0 to 100% scale, where 0% indicates no injury and 100% indicates complete plant death.
4.) Flowering date: This measurement records the date when 50% of the plants in the plot begin to flower. The number of days from planting to when 50% of the plants in each plot were flowering was recorded.
5.) Stand count at R2 or R1: Is a visual estimate of the average vigor of plants in each plot, determined by counting the number of plants in a representative one meter section of one row per plot, and taking note at the R2 or R1 growth stage.
6.) Rated overall visual crop injury, chlorosis and necrosis at 1 day, 7 days, and 14 days after R2 chemical application. Observations were made for any signs of epinasty which is typical of 2,4-D injury. Epinasty is exhibited as twisting or drooping of leaves and stems. All crop injuries used a 0 to 100% scale where 0% indicates no injury and 100% indicates complete plant death.
7.) Disease incidence at R6 growth stage: Is a visual estimate of disease incidence used to record the severity of disease in the plot. Rated on a scale of 0-100%. Where 0% indicates no disease present and 100% indicates all plants in plot had disease.
8.) Insect damage at R6 growth stage: Is a visual estimate of insect damage used to record the severity of insect damage in the plot. Recorded the percentage of plant tissue in the plot damaged by insects using a 0-100% scale. Where 0% indicates no insect damage present and 100% indicates all plants in plot had insect damage.
9.) Plant height at senescence: The average height of the plants in each plot was recorded. Plants were measured from the soil surface to the tip after the leaves had fallen. Measurements were recorded in centimeters. If the plot was lodged, a representative group of plants were stood-up to obtain a measurement.

10.) Days to maturity. Recorded date when 95% of the pods in a plot reached physiological maturity and the plants were a dry down color. The numbers of days to elapse since planting were calculated.

11.) Lodging: Recorded a visual estimate of lodging severity at harvest time. Recorded on a 0 to 100% scale with 0% indicates no lodging and 100% indicates all plants in a plot flat on the ground.

12.) Shattering: Recorded a visual estimate of pod shattering at harvest time. Recorded as an estimate of percentage of pods shattered per plot. 0-100% scale with 0% indicating no shattering and 100% indicating all pods shattered.

13.) Yield: Recorded the weight of grain harvested from each plot. Harvested the entire 2 row plot and recorded seed weight and moisture. Calculations for bu/acre were made by adjusting to 13% moisture.

14.) 100 seed weight: For each plot 100 seeds were counted out and the weight was recorded in grams.

Herbicide tolerance of soybean Event pDAB8291.45.36.2 was assessed following the application of a tankmix of 2,4-D and glyphosate at 2,185 g ae/ha mixed with 2% weight per weight ammonium sulfate (AMS). The herbicides were sprayed as a V3/R2 sequential herbicide treatment. This herbicide treatment was completed by spraying soybean plants at the V3 growth stage of development followed by a second sequential application at the R2 growth stage of development. The V3 growth stage is characterized when the unifoliolate and first three trifoliolate leaves are fully developed. The R2 growth stage is characterized by a single open flower at one of the two uppermost nodes on the main stem with a fully developed leaf.

These trials were set up using a randomized complete block design with four replications for every treatment. Each plot was 2 rows wide and rows were spaced 30 inches apart. Plots were planted to a total length of 12.5 ft with a 2.5 to 3.0 foot alley between plots. Maverick control plants were expected to die from herbicide applications so they were grown in a separate plot; away from the transgenic soybean plant rows.

The results of soybean Event pDAB8291.45.36.2 sprayed with the 2,4-D and glyphosate herbicide tank mix as compared to unsprayed soybean Event pDAB8291.45.36.2 are summarized. Table 7 presents the means from an analysis comparing Soybean Event pDAB8291.45.36.2 sprayed with a tankmix of 2,4-D and glyphosate to unsprayed Soybean Event pDAB8291.45.36.2. The herbicide application did not damage Soybean Event pDAB8291.45.36.2, these plants were performed equivalently to unsprayed Soybean Event pDAB8291.45.36.2 plants for the reported agronomic characteristics listed in Table 7. With the exception of some early transient injury 1 and 7 daa (days after application) at the V3 stage of development and at 1, 7 and 14 daa at the R2 stage of development, Soybean Event pDAB8291.45.36.2 showed robust tolerance to the 2,4-D and glyphosate tank mix. In contrast, none of the Maverick plants were surviving after being sprayed with the herbicides.

TABLE 7

Comparison of Soybean Event pDAB8291.45.36.2 sprayed and unsprayed with a tank mix of 2,4-D glyphosate. Soybean Event pDAB8291.45.36.2

| Trait: Agronomic Characteristics | Sprayed | Non-sprayed |
| --- | --- | --- |
| Emergence (%) | 85.4 | 83.0 |
| Seedling Vigor at V1 (%) | 89.7 | 89.7 |
| Rated overall visual crop injury after V3 herbicide application; Injury 1 daa (%) | 1.4 | 0.1 |
| Rated overall visual crop injury after V3 herbicide application; Injury 7 daa (%) | 1.3 | 0.0 |
| Rated overall visual crop injury after V3 herbicide application; 14 daa (%) | 0.0 | 0.0 |
| Days to flower (days from planting) | 39.4 | 39.4 |
| Stand count at R2 | 23.7 | 23.7 |
| Rated overall visual crop injury after R2 herbicide application; Injury 1 daa (%) | 3.1 | 0.4 |
| Rated overall visual crop injury after R2 herbicide application; Injury 7 daa (%) | 2.8 | 0.0 |
| Rated overall visual crop injury after R2 herbicide application; Injury 14 daa (%) | 1.7 | 0.2 |
| Disease incidence (%) | 1.5 | 1.4 |
| Insect damage (%) | 7.9 | 7.4 |
| Height (cm) | 106.0 | 107.7 |
| Maturity (days from planting) | 114.1 | 114.4 |
| Lodging (%) | 16.6 | 13.9 |
| Shattering (%) | 0.1 | 0.1 |
| Yield (bu/acre) | 44.7 | 45.1 |
| 100 seed weight (g) | 11.6 | 11.4 |

Agronomic equivalence of Soybean Event pDAB8291.45.36.2 and the control line, Maverick, was assessed. These trials were set up using a block design with two replications. Each plot was 2 rows wide and rows were spaced 30 inches apart. Plots were planted to a total length of 12.5 ft with a 2.5 to 3.0 foot alley between plots.

Table 8 presents the means from the analysis comparing the agronomic equivalence of Soybean Event pDAB8291.45.36.2 with the control line, Maverick. The agronomic data is indicative that Soybean Event pDAB8291.45.36.2 performs equivalently to Maverick plants, and does not result in agronomically meaningful unintended differences.

TABLE 8

Comparison of Soybean event pDAB8291.45.36.2 to Maverick control lines in yield trials.

| | Maverick | | pDAB8291.45.36.2 | |
| --- | --- | --- | --- | --- |
| Emergence (%) | 86.2 | A | 83.2 | A |
| Vigor V1 (1 poor-9 good) | 91.0 | A | 91.2 | A |
| Days to flower (days from planting) | 41.2 | A | 41.1 | A |
| Stand count at R1 | 22.7 | A | 23.3 | A |
| Disease incidence (%) | 1.8 | A | 1.8 | A |
| Insect damage (%) | 7.8 | A | 8.0 | A |
| Height (cm) | 110.3 | A | 110.1 | A |
| Maturity (days from planting) | 119.7 | A | 119.6 | A |
| Lodging (%) | 16.1 | A | 17.8 | A |
| Shattering | 0.2 | A | 0.2 | A |
| Yield (bu/acre) | 45.7 | A | 45.3 | A |
| 100 seed weight | 13.2 | A | 12.1 | B |

For each trait values not followed by the same letter are different according to Student's T-distribution statistical analysis.

Example 6

Event Specific Taqman Assay

Two event specific TAQMAN assays were developed to detect the presence of soybean event pDAB8291.45.36.2 and to determine zygosity status of plants in breeding populations. Soybean event pDAB8291.45.36.2 contains the T-strand of the binary vector pDAB8291 (FIG. 1). For specific detection of soybean event pDAB8291.45.36.2, specific Taqman primers and probes were designed according to the DNA sequences located in the 5' (SEQ ID NO:14) or 3' (SEQ ID NO:15) insert-to-plant junction (FIG. 4). One event specific assay for soybean event pDAB8291.45.36.2 was designed to specifically detect a 72 bp DNA fragment (SEQ ID NO:16) that spans the 5' integration junction using two primers and a target-specific MGB probe synthesized by Applied Biosystems (ABI) containing the FAM reporter at its 5' end. Another event specific assay for soybean event pDAB8291.45.36.2 was designed to specifically target a 142 bp DNA fragment (SEQ ID NO:17) that spans the 3' integration junction using two specific primers and a target-specific MGB probe synthesized by ABI containing the FAM reporter at its 5' end. Specificity of this Taqman detection method for soybean event pDAB8291.45.36.2 was tested against 11 different EPDM and aad-12 molecular stack soybean events and a control non-transgenic soybean variety (Maverick) in duplex format with the soybean specific endogenous reference gene, GMFL01-25-J19 (*Glycine max* cDNA, GenBank: AK286292.1).

soybean leaf discs, 8 per sample, were used for gDNA extraction. The gDNA was quantified with the Pico Green method according to vendor's instructions (Molecular Probes, Eugene, Oreg.). Samples were diluted with DNase-free water resulting in a concentration of 10 ng/μL for the purpose of this study.

Example 6.2

Taqman Assay and Results

Specific Taqman primers and probes were designed for a soybean event pDAB8291.45.36.2 specific Taqman assay. These reagents can be used with the conditions listed below to detect the transgene within soybean event pDAB8291.45.36.2. Table 9 lists the primer and probe sequences that were developed specifically for the detection of soybean event pDAB8291.45.36.2.

TABLE 9

Taqman PCR Primers and Probes.

| Event Target Reaction | | | |
|---|---|---|---|
| SEQ ID NO:Name | Name | Description | Sequence |
| SEQ ID NO: 18 | 4536_5'F | Event specific forward Primer | ACATGTTTTGCTGTCGACGTTAA |
| SEQ ID NO: 19 | 4536_5'R | Event specific reverse Primer | TTTCAAACTATTCGGGCCTAACTT |
| SEQ ID NO: 20 | 4536_5'P | Event specific probe used with 4536_5'F and 4536_5'R | 5' FAM-AAGAGTCAGCATCATC-MGB |
| SEQ ID NO: 21 | 4536_3'F | Event specific forward Primer | CGTCCGCAATGTGTTATTAAGTTG |
| SEQ ID NO: 22 | 4536_3'R | Event specific reverse Primer | CAGAAGGTTGGACTTTTGCATATG |
| SEQ ID NO: 23 | 4536_3'P | Event specific probe used with 4536_3'F and 4536_3'R | 5'FAM/CAATTGTTGAGGTTGCC-MGB |

| Reference System Reaction | | | |
|---|---|---|---|
| SEQ ID NO:Name | Name | Description | 5' to 3' sequence |
| SEQ ID NO: 24 | GMS116 F | Forward Primer | GTAATATGGGCTCAGAGGAATGGT |
| SEQ ID NO: 25 | GMS116 R | Reverse Primer | ATGGAGAAGAACATTGGAATTGC |
| SEQ ID NO: 26 | GMS116 Probe | Probe | 5'HEX/CCATGGCCCGGTACCATCTGGTC/3BHQ_1/3' |

Example 6.1 gDNA Isolation gDNA samples of 11 different soybean events and non-transgenic soybean varieties were tested in this study. Genomic DNA was extracted using modified Qiagen MagAttract plant DNA kit (Qiagen, Valencia, Calif.). Fresh The multiplex PCR conditions for amplification are as follows: 1× Roche PCR Buffer, 0.4 μM event specific forward primer, 0.4 μM event specific reverse primer, 0.4 μM Primer GMS116 F, 0.4 μM Primer GMS116 R, 0.2 μM Event specific probe, 0.2 μM GMS116 Probe, 0.1% PVP, 20 ng gDNA in a total reaction of 10 μl. The cocktail was amplified using the following conditions: i) 95° C. for 10 min., ii) 95° C. for 10 sec, iii) 60° C. for 30 sec, iv) 72° C. for 1 sec v) repeat step ii-iv for 35 cycles, v) 40° C. hold. The Real time PCR was carried out on the Roche LightCycler 480. Data analysis was based on measurement of the crossing point (Cp value) determined by LightCycler 480 software, which is the PCR cycle number when the rate of change in fluorescence reaches its maximum.

The Taqman detection method for soybean event pDAB8291.45.36.2 was tested against 11 different 2mEPSPS and aad-12 molecular stack soybean events and non-transgenic soybean varieties in duplex format with soybean specific endogenous reference gene, GMFL01-25-J19 (GenBank: AK286292.1). The assays specifically detected the soybean event DAB8291.45.36.2 and did not produce or amplify any false-positive results from the controls (i.e. the 11 different 2mEPSPS and aad-12 molecular stack soybean events and non-transgenic soybean varieties). The event specific primers and probes can be used for the detection of the soybean event pDAB8291.45.36.2 and these conditions and reagents are applicable for zygosity assays.

Example 7

Expected Sequence of Soybean Event pDAB8291.45.36.2

SEQ ID NO:27 provides the expected sequence of soybean Event pDAB8291.45.36.2. This sequence contains the 5' genomic flanking sequence, the expected T-strand insert of pDAB8291 and 3' genomic flanking sequences. With respect to SEQ ID NO:27, residues 1-781 are 3' genomic flanking sequence, residues 782-11,103 are the pDAB8291 T-strand insert, and residues 11,104-14,191 are 5' flanking sequence. The junction sequence or transition with respect to the 3' end of the insert thus occurs at residues 781-782 of SEQ ID NO:27. The junction sequence or transition with respect to the 5' end of the insert thus occurs at residues 11,103-11,104 of SEQ ID NO:27.

It should be noted that SEQ ID NO:27 is the expected representation of soybean Event pDAB8291.45.36.2 and was assembled from an alignment of SEQ ID NO:1, SEQ ID NO:2, and the T-strand of pDAB8291. The actual sequence of the T-strand insert of soybean Event pDAB8291.45.36.2 may slightly deviate from SEQ ID NO:27. During the transformation process of introducing an T-stand insert into the genome of plant cells, it is not uncommon for some deletions or other alterations of the insert to occur. Moreover, errors in PCR amplification can occur which might result in minor sequencing errors. For example, flanking sequences listed herein were determined by generating amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject invention. Thus, the relevant segment of the plasmid sequence provided herein might comprise some minor variations. Thus, a plant comprising a polynucleotide having some range of identity with the subject insert sequence is within the scope of the subject invention. Identity to the sequence of SEQ ID NO:27 can be a polynucleotide sequence having at least 90%, 91%, 92%, 93%, 94%, 95%, 96%, 97%, 98%, 99% sequence identity with a sequence exemplified or described herein. The sequence of the flanking sequences plus insert sequence can be confirmed with reference to the deposited seed. Thus, some differences between SEQ ID NO:27 and the actual T-strand insert of soybean Event pDAB8291.45.36.2 may be identified.

The invention claimed is:

1. A transgenic soybean plant cell comprising a genome, said genome comprising SEQ ID NO: 27, wherein said SEQ ID NO: 27 comprises a first junction sequence represented by SEQ ID NO:16 and a second junction sequence represented by SEQ ID NO:17.

2. A soybean seed comprising a genome comprising Event pDAB8291.45.36.2 wherein said soybean seed is present in representative seed deposited with American Type Culture Collection (ATCC) under Accession No. PTA-11335.

3. A soybean seed comprising the transgenic soybean plant cell of claim 1, said seed comprising said polynucleotide segment.

4. A soybean plant produced by growing the seed of claim 2, said plant comprising said Event pDAB8291.45.36.2.

5. A progeny plant of the soybean plant of claim 4, said progeny plant comprising said Event pDAB8291.45.36.2.

6. A transgenic soybean plant comprising a plurality of the transgenic soybean plant cells of claim 1.

7. The transgenic soybean plant of claim 6, said plurality of transgenic soybean plant cells further comprising an insect resistance gene.

8. The transgenic soybean plant of claim 6 wherein the plant is resistant to at least one herbicide selected from the group consisting of a phenoxyacetic acid herbicide, a phenoxybutanoic acid herbicide, a pyridyloxyalkanoic acid herbicide, a glyphosate herbicide, and a glufosinate herbicide.

9. A part of the soybean plant of claim 4 wherein said part is selected from the group consisting of pollen, an ovule, a flower, a shoot, a root, and a leaf, said part comprising said Event pDAB8291.45.36.2.

10. A soybean plant cell comprising a genome comprising Event pDAB8291.45.36.2 as present in representative seed deposited with American Type Culture Collection (ATCC) under Accession No. PTA-11335.

11. An isolated polynucleotide wherein said polynucleotide comprises a nucleotide sequence selected from the group consisting of SEQ ID NOS: 13, 14-17, and 27.

12. A method of controlling weeds in a field, said method comprising applying a herbicide selected from the group consisting of a phenoxyacetic acid, a phenoxybutanoic acid, a pyridyloxyalkanoic acid, a glyphosate, and a glufosinate to the field, and planting a seed of claim 3 in the field within 14 days of applying the herbicide.

13. The transgenic soybean plant of claim 6, wherein the plant is from *Glycine max*.

14. A probe that is at least 95% identical to a full length sequence selected from the group consisting of SEQ ID NO: 14, SEQ ID NO: 15, and the complements thereof.

* * * * *

UNITED STATES PATENT AND TRADEMARK OFFICE
CERTIFICATE OF CORRECTION

PATENT NO. : 9,540,656 B2
APPLICATION NO. : 13/991309
DATED : January 10, 2017
INVENTOR(S) : Cui et al.

It is certified that error appears in the above-identified patent and that said Letters Patent is hereby corrected as shown below:

On the Title Page

Item (73), please insert:
-- M.S. Technologies, LLC, Adel, IA (US) -- immediate after "Dow AgroSciences LLC, Indianapolis, IN (US)."

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*